United States Patent [19]

Fujii et al.

[11] Patent Number: 5,037,976

[45] Date of Patent: * Aug. 6, 1991

[54] 2-OXA-ISOCEPHEM COMPOUNDS

[75] Inventors: Setsuro Fujii, Kyoto; Hiroshi Ishikawa; Koichi Yasumura, both of Otsu; Koichiro Jitsukawa, Ashiya; Sachio Toyama, Otsu; Hidetsugu Tsubouchi, Otsu; Kimio Sudo, Otsu; Kouichi Tsuji, Otsu, all of Japan

[73] Assignee: Otsuka Pharmaceutical Co., Ltd., Tokyo, Japan

[*] Notice: The portion of the term of this patent subsequent to Feb. 6, 2007 has been disclaimed.

[21] Appl. No.: 430,539

[22] Filed: Nov. 1, 1989

Related U.S. Application Data

[63] Continuation of Ser. No. 165,942, Mar. 9, 1988, Pat. No. 4,898,859.

[30] Foreign Application Priority Data

Mar. 9, 1987 [JP] Japan ................. 62-53870
Jul. 14, 1987 [JP] Japan ................. 62-175045
Sep. 3, 1987 [JP] Japan ................. 62-221043
Jan. 28, 1988 [JP] Japan ................. 63-18350

[51] Int. Cl.5 ............................ C07D 498/04
[52] U.S. Cl. .............................. 540/300
[58] Field of Search .......................... 540/300

[56] References Cited

U.S. PATENT DOCUMENTS 4,831,026 5/1989 Fujii et al. ............... 514/210
4,898,859 2/1990 Fujii et al. ............... 514/210

Primary Examiner—Richard L. Raymond
Attorney, Agent, or Firm—Sughrue, Mion, Zinn, Macpeak & Seas

[57] ABSTRACT

A 2-oxa-isocephem compound of the formula (1):

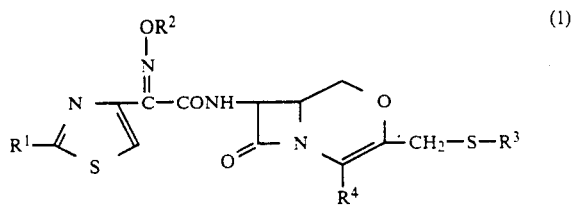

wherein $R^1$, $R^2$, $R^3$ and $R^4$ are as defined, pharmaceutically acceptable salts thereof, composition containing the same and processes for preparing the same are disclosed. The compound is useful as an antimicrobial agent.

12 Claims, No Drawings

2-OXA-ISOCEPHEM COMPOUNDS

This is a continuation of application Ser. No. 07/165,942 filed Mar. 9, 1988, now U.S. Pat. No. 4,898,859.

FIELD OF THE INVENTION

This invention relates to new 2-oxa-isocephem compounds and pharmaceutically acceptable salts thereof which are useful as antimicrobial compounds, processes for preparing the same, and pharmaceutical compositions containing the 2-oxa-isocephem compounds or salts thereof.

BACKGROUND OF THE INVENTION

Various 2-oxa-isocephem compounds are known which have antimicrobial activity as described in U.S. Pat. No. 4476124 and European Patent Application Publication No. A1-215435.

However, the 2-oxa-isocephem compounds of this invention are structurally different from the conventional 2-oxa-isocephem compounds.

SUMMARY OF THE INVENTION

One object of this invention is to provide 2-oxa-isocephem compounds having antimicrobial activity.

Another object of this invention is to provide a pharmaceutical composition containing the 2-oxa-isocephem compound in an antimicrobially effective amount.

A further object of this invention is to provide a process for preparing the 2-oxa-isocephem compounds and pharmaceutically acceptable salts thereof.

As a result of extensive research this invention has been accomplished which, in one aspect, provides a 2-oxa-isocephem compound of the following formula (1) and pharmaceutically acceptable salts thereof:

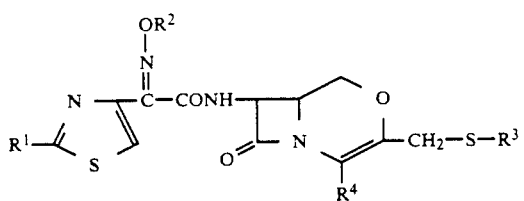

wherein $R^1$ is an amino group, a lower alkanoylamino group, a halogen-substituted lower alkanoylamino group, a phenyl-substituted lower alkylamino group having 1 to 3 phenyl groups, a phenyl-lower alkoxycarbonylamino group or a lower alkoxycarbonylamino group; $R^2$ is a lower alkyl group, a cycloalkyl group, a cyano-lower alkyl group, a carboxy-lower alkyl group or a carbamoyl-lower alkyl group; $R^3$ is a pyridyl group or a pyridinio group, in which the pyridinio group is substituted with a lower alkyl group, a cycloalkyl-lower alkyl group, a lower alkoxy-lower alkyl group, a lower alkanoyl-lower alkyl group, a benzoyl-lower alkyl group, a halogen-substituted lower alkyl group, a lower alkyl group substituted with a halogen-substituted lower alkanoyl group, a carboxycarbonyl-lower alkyl group, a lower alkyl group substituted with a lower alkoxyimino group, or a group of the formula:

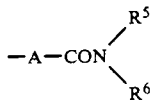

in which A is a lower alkylene group, $R^5$ is a hydrogen atom or a lower alkyl group, $R^6$ is a lower alkyl group or a hydroxy group, and $R^5$ and $R^6$ together with the adjacent nitrogen atom may form a saturated 5- or 6-membered heterocyclic group which may contain further an oxygen atom, a nitrogen atom and/or a sulfur atom, and further said heterocyclic group may be substituted with a hydroxy group or a lower alkyl group; and $R^4$ is a carboxy group, a carboxylate group or an esterified carboxy group, provided that $R^2$ is a carbamoyl-lower alkyl group, when $R^3$ is a pyridyl group, or a pyridinio group substituted with a lower alkyl group.

In another aspect, this invention provides an antimicrobial composition containing the compound of the formula (1) or a pharmaceutically acceptable salt thereof in an antimicrobially effective amount.

In a further aspect, this invention provides a process for preparing the compounds of the formula (1) and pharmaceutically acceptable salts thereof.

In a still further aspect, this invention provides a process for preparing azetidinone compounds which are useful as intermediates for the synthesis of 2-oxa-isocephem compounds.

The above compound of the formula (1) according to the present invention has high antimicrobial activity against a broad spectrum of gram-positive and gram-negative bacteria, displaying particularly high activity against gram-positive bacterias such as *Staphylococcus aureus* (FDA-209-P), *Streptococcus pneumoniae* and *Corynebacterium diphtheriae*.

The compound according to the present invention is further characterized by good absorption, long duration of effect, low toxicity and excellent effects on resistant strains and clinically isolated strains of bacteria. Moerover, the compound is highly stable and has a satisfactory pharmacokinetic profile. Thus, the compound shows a high renal excretion and a good transfer into the bile. It is well distributed in various organs including the lungs. The difference between minimal inhibitory concentration and minimal bactericidal concentration is small. Furthermore, the compound has few side effects such as immunosuppression and allergy.

Therefore, the compound according to the present invention is also useful as a therapeutic agent for the diseases caused by various pathogenic bacteria in man, animals and fish or as an external microbicide or disinfectant for medical devices, instruments and so on.

DETAILED DESCRIPTION OF THE INVENTION

The groups given in terms of symbols in the above general formula (1) are respectively described in more detail in the following.

Examples of the lower alkanoylamino group include alkanoylamino groups having 1 to 6 carbon atoms, such as formylamino, acetylamino, propionylamino, butyrylamino, isobutyrylamino, pentanoylamino, hexanoylamino and the like.

Examples of the halogen-substituted lower alkanoylamino group include alkanoylamino groups having 2 to 6 carbon atoms and substituted by 1 to 3 halogen atoms, such as monochloroacetylamino, monofluoroacetylamino, monobromoacetylamino, monoiodoacetylamino, dichloroacetylamino, trichloroacetylamino, tribromoacetylamino, 3-chloropropionylamino, 2,3-dichloropropionylamino, 3,3,3-trichloropropionylamino, 4-chlorobutyrylamino, 5-chloropentanoylamino, 6-chlorohexanoylamino, 3-fluoropropionylamino, 4-fluorobutyrylamino and the like.

Examples of the phenyl-lower alkylamino group having 1 to 3 phenyl groups include phenylalkylamino groups containing 1 to 3 phenyl groups and having 1 to 6 carbon atoms in the alkyl moiety thereof, such as benzylamino, α-phenethylamino, β-phenethylamino, 3-phenylpropylamino, benzhydrylamino, tritylamino and the like.

Examples of the phenyl-lower alkoxycarbonylamino group include phenylalkoxycarbonylamino groups having 1 to 6 carbon atoms in the alkoxy moiety thereof, such as 1-phenylethoxycarbonylamino, 2-phenylethoxycarbonylamino, 3-phenylpropoxycarbonylamino, 4-phenylbutoxycarbonylamino, 5-phenylpentyloxycarbonylamino, 6-phenylhexyloxycarbonylamino and the like.

Examples of the lower alkoxycarbonylamino group include alkoxycarbonylamino groups having 1 to 6 carbon atoms in the alkoxy moiety thereof, such as methoxycarbonylamino, ethoxycarbonylamino, propoxycarbonylamino, isopropoxycarbonylamino, butoxycarbonylamino, tertiary-butoxycarbonylamino, pentyloxycarbonylamino, hexyloxycarbonylamino and the like.

Examples of the lower alkyl group include alkyl groups having 1 to 6 carbon atoms, such as methyl, ethyl, propyl, isopropyl, butyl, isobutyl, tertiary-butyl, pentyl, hexyl and the like.

Examples of the cycloalkyl group include cycloalkyl groups having 3 to 8 carbon atoms, such as cyclopropyl, cyclobutyl, cyclopentyl, cyclohexyl, cycloheptyl, cyclooctyl and the like.

Examples of the cyano-lower alkyl group include cyano-bearing alkyl groups of 1 to 6 carbon atoms such as cyanomethyl, 1-cyanoethyl, 2-cyanoethyl, 2-cyanopropyl, 3-cyanopropyl, 2-cyano-1-methylethyl, 4-cyanobutyl, 5-cyanopentyl, 6-cyanohexyl and the like.

Examples of the carboxy-lower alkyl group include carboxyalkyl groups having 1 to 6 carbon atoms in the alkyl moiety thereof, such as carboxymethyl, 1-carboxyethyl, 2-carboxyethyl, 2-carboxypropyl, 3-carboxypropyl, 2-carboxy-1-methylethyl, 4-carboxybutyl, 5-carboxypentyl, 6-carboxyhexyl and the like.

Examples of the carbamoyl-lower alkyl group include carbamoyl-bearing alkyl groups of 1 to 6 carbon atoms, such as carbamoylmethyl, 1-carbamoylethyl, 2-carbamoylethyl, 2-carbamoylpropyl, 3-carbamoylpropyl, 2-carbamoyl-1-methylethyl, 4-carbamoylbutyl, 5-carbamoylpentyl, 6-carbamoylhexyl and the like.

Examples of the cycloalkyl-lower alkyl group include cycloalkyl-alkyl groups having 1 to 6 carbon atoms in the alkyl moiety thereof and having 3 to 8 carbon atoms in the cycloalkyl moiety thereof, such as cyclohexylmethyl, 2-cyclohexylethtyl, 3-cyclohexylpropyl, 4-cyclohexylbutyl, 5-cyclohexylpentyl, 6-cyclohexylhexyl, cyclopropylmethyl, 2-cyclobutylethyl, cyclopentylmethyl, 2-cycloheptylethyl, cyclooctylmethyl and the like.

Examples of the lower alkoxy-lower alkyl group include alkoxyalkyl groups having 1 to 6 carbon atoms in the alkoxy moiety thereof and having 1 to 6 carbon atoms in the alkyl moiety thereof, such as methoxymethyl, 3-methoxypropyl, 4-ethoxybutyl, 6-propoxyhexyl, 5-isopropoxypentyl, 1,1-dimethyl-2-ethoxyethyl, 3-t-butoxymethyl, 2-pentyloxyethyl, 6-hexyloxyhexyl and the like.

Examples of the lower alkanoyl-lower alkyl group include alkanoylalkyl groups having 1 to 6 carbon atoms in the alkanoyl moiety thereof and having 1 to 6 carbon atoms in the alkyl moiety thereof, such as formylmethyl, acetonyl, 3-acetylpropyl, 4-acetylbutyl, 6-propionylhexyl, 5-isobutyrylpentyl, 1,1-dimethyl-2-pentanoylethyl, hexanoylmethyl, 6-hexanoylhexyl and the like.

Examples of the benzoyl-lower alkyl group include benzoylalkyl groups having 1 to 6 carbon atoms in the alkyl moiety thereof, such as benzoylmethyl, 2-benzoylethyl, 3-benzoylpropyl, 2-benzoylbutyl, 1-benzoyl-2-methylbutyl, 5-benzoylpentyl, 6-benzoylhexyl and the like.

Examples of the halogen-substituted lower alkyl group include halogen-substituted alkyl groups containing 1 to 3 halogen atoms and having 1 to 6 carbon atoms in the alkyl moiety thereof, such as chloromethyl, bromomethyl, iodomethyl, fluoromethyl, dichloromethyl, dibromomethyl, difluoromethyl, trichloromethyl, tribromomethyl, trifluoromethyl, 2-chloroethyl, 2-bromoethyl, 2-fluoroethyl, 1,2-dichloroethyl, 2,2-difluoroethyl, 1-chloro-2-fluoroethyl, 2,2,2-trifluoroethyl, 2,2,2-trichloroethyl, 3-fluoropropyl, 3,3,3-trichloropropyl, 4-chlorobutyl, 5-chloropentyl, 6-chlorohexyl, 3-chloro-2-methylpropyl and the like.

Examples of the halogen-substituted lower alkanoyl groups include halogen-substituted alkanoyl groups containing 1 to 3 halogen atoms and having 2 to 6 carbon atoms in the alkanoyl moiety thereof, such as 2-chloroacetyl, 2-bromoacetyl, 2-iodoaceyyl, 2-fluoroacetyl, 2,2-dichloroacetyl, 2,2-difluoroacetyl, 2,2,2-trifluoroacetyl, 2,2,2-trichloroacetyl, 3-chloropropionyl, 3-fluoropropionyl, 3,3,3-trichloropropionyl, 4-chlorobutyryl, 4-bromobutyryl, 5-chloropentanoyl, 6-chlorohexanoyl, 3-chloro-2-methylpropionyl and the like.

Accordingly, examples of the alkyl group substituted with these halogen-substituted lower alkanoyl group include alkyl groups substituted with halogen-substituted alkanoyl group containing the above-mentioned halogen substituted alkanoyl group and having 1 to 6 carbon atoms in the alkyl moiety thereof, such as 2-chloroacetylmethyl, 2-bromoacetylmethyl, 2-fluoroacetylmethyl, 2,2-dichloroacetylmethyl, 2,2-difluoroacetylmethyl, 2,2,2-trifluoroacetylmethyl, 2,2,2-trichloroacetylmethyl, 3-fluoropropionylmethyl, 4-chlorobutyrylmethyl, 5-chloropentanoylmethyl, 6-chlorohexanoylmethyl, 1-(2-chloroacetyl)ethyl, 2-(2-chloroacetyl)ethyl, 1-(2-fluoroacetyl)ethyl, 2-(2-fluoroacetyl)ethyl, 2-(2,2,2-trichloroacetyl)ethyl, 2-(2-fluoropropionyl)ethyl, 2-(3-chloro-2-methylpropionyl)ethyl, 2-(6-chlorohexanoyl)ethyl, 3-(2-chloroacetyl)propyl, 2-(2-chloroacetyl)propyl, 3-(2-fluoroacetyl)propyl, 3-(3-fluoropropionyl)propyl, 3-(6-chlorohexanoyl)propyl, 3-(2-fluoroacetyl)butyl, 4-(2-fluoroacetyl)butyl, 4-(6-chlorohexanoyl)butyl, 5-(2-chloroacetyl)pentyl, 5-(2,2,2-trifluoroacetyl)pentyl, 5-(3-fluoropropionyl)pentyl, 5-(6-chlorohexanoyl)pentyl, 6-(2-fluoroacetyl)hexyl, 6-(5-bromopentanoyl)hexyl, 6-(6-chlorohexanoyl)hexyl and the like.

Examples of the carboxycarbonyl-lower alkyl group include carboxycarbonyl-bearing alkyl groups of 1 to 6 carbon atoms, such as carboxycarbonylmethyl, 1-carboxycarbonylethyl, 2-carboxycarbonylethyl, 2-carboxycarbonyl-1-methylethyl, 1-carboxycarbonylpropyl, 3-carboxycarbonylpropyl, 3-carboxycabonyl-2-methylpropyl, 2-carboxycarbonylbutyl, 4-carboxycarbonylbutyl, 5-carboxycarbonylpentyl, 3-carboxycarbonylhexyl, 6-carboxycarbonylhexyl and the like.

Examples of the lower alkoxyimino moiety of the lower alkyl group substituted with a lower alkoxyimino group include alkoxyimino groups having 1 to 6 carbon atoms in the alkoxy moiety thereof, such as methoxyimino, ethoxyimino, propoxyimino, isopropoxyimino, butoxyimino, pentyloxyimino, hexyloxyimino and the like.

Accordingly, examples of the lower alkyl group substituted with the above-mentioned alkoxyimino group include alkyl groups containing lower alkoxyimino and having 1 to 6 carbon atoms in the alkyl moiety thereof, such as methoxyiminomethyl, ethoxyiminomethyl, propoxyiminomethyl, butoxyiminomethyl, pentyloxyiminomethyl, hexyloxyiminomethyl, 1-methoxyiminoethyl, 2-methoxyiminoethyl, 1-ethoxyiminoethyl, 2-ethoxyiminoethyl, 2-propoxyiminoethyl, 2-propoxyiminoethyl, 2-hexyloxyiminoethyl, 1-methoxyiminopropyl, 2-methoxyiminopropyl, 3-methoxyiminopropyl, 3-ethoxyiminopropyl, 1-methoxyiminobutyl, 4-ethoxyiminobutyl, 1-methoxyiminopentyl, 5-methoxyiminopentyl, 5-ethoxyiminopentyl, 1-methoxyiminohexyl, 6-methoxyiminohexyl, 6-ethoxyiminohexyl, 6-hexyloxyiminohexyl and the like.

Examples of the lower alkylene group include alkylene groups having 1 to 6 carbon atoms, such as methylene methylmethylene, ethylene, dimethylmethylene, trimethylene, 1-methyl trimethylene, 2-methyltrimethylene, 2,2-dimethyltrimethylene, tetramethylene, pentamethylene, hexamethylene and the like.

Examples of the saturated 5- or 6-membered heterocyclic group formed by $R^5$ and $R^6$ together with the adjacent nitrogen atom and which may contain further an oxygen atom, a nitrogen atom and/or a sulfur atom may be 1-piperazinyl, piperidino, 1-pyrrolidinyl, 1-imidazolidinyl, morpholino, thiomorpholino, 2-isoxazolidinyl, 3-thiazolidinyl and the like.

The ester residue of the esterified carboxy group is exemplified by conventional ester residues, for example, alkyl groups of 1 to 6 carbon atoms such as methyl, ethyl, propyl, isopropyl, butyl, isobutyl, tertiary-butyl, pentyl, hexyl, etc.; (mono- or di-)phenyl-lower alkyl groups containing 1 to 6 carbon atoms in the alkyl moiety thereof such as benzyl, benzhydryl, α-phenethyl, β-phenethyl, α,β-diphenylethyl, 3-phenylpropyl, 4-phenylbutyl, 5-phenylpentyl, 6-phenylhexyl, etc.; alkenyl groups of 2 to 6 carbon atoms such as vinyl, allyl, crotyl, 2-pentenyl, 2-hexenyl, etc.; cycloalkyl groups of 3 to 8 carbon atoms such as cyclopropyl, cyclobutyl, cyclopentyl, cyclohexyl, cycloheptyl, cyclooctyl, etc.; and cycloalkyl(lower)alkyl groups containing 3 to 8 carbon atoms in the cycloalkyl moiety and 1 to 6 carbon atoms in the alkyl moiety thereof such as cyclohexylmethyl, 2-cyclohexylethyl, 3-cyclohexylpropyl, 4-cyclohexylbutyl, 5-cyclohexylpentyl, 6-cyclohexylhexyl, cyclopropylmethyl, 2-cyclobutylethyl, cyclopentylmethyl, 2-cycloheptylethyl, cyclooctylmethyl, etc.

Further, the phenyl moiety of the (mono- or di-)phenyl-lower alkyl group as one of the above-mentioned ester residues may optionally have 1 to 3 substituents selected from the group comprising halogen atoms, such as chlorine, bromine, fluorine and iodine atoms; alkyl groups of 1 to 6 carbon atoms such as methyl, ethyl, propyl, isopropyl, butyl, isobutyl, tertiary-butyl, pentyl, hexyl, etc.; alkoxy groups of 1 to 6 carbon atoms such as methoxy, ethoxy, propoxy, isopropoxy, butoxy, tertiary-butoxy, pentyloxy, hexyloxy, etc.; nitro group; carboxy group; cyano group; alkoxycarbonyl groups containing 1 to 6 carbon atoms in the alkoxy moiety thereof such as methoxycarbonyl, ethoxycarbonyl, propoxycarbonyl, isopropoxycarbonyl, butoxycarbonyl, tertiary-butoxycarbonyl, pentyloxycarbonyl, hexyloxycarbonyl, etc.; hydroxy group; and lower alkanoyloxy groups containing 1 to 6 carbon atoms in the alkanoyl moiety thereof such as acetyloxy, propionyloxy, butyryloxy, isobutyryloxy, pentanoyloxy, hexanoyloxy, etc.; or a lower alkylenedioxy group of 1 to 4 carbon atoms such as methylenedioxy, ethylenedioxy, trimethylenedioxy, tetramethylenedioxy, etc.

The lower alkyl group as one of the above-mentioned ester residues may optionally be substituted by 1 to 3 halogen atoms mentioned above, a hydroxy group, a mercapt group, the above-mentioned lower alkoxy group, the above-mentioned lower alkanoyloxy group, a carboxy group, a cyano group, a nitro group, an amino group, the above-mentioned lower alkyl group, a (mono- or di-)lower alkylamino group such as methylamino, dimethylamino, ethylamino, diethylamino, propylamino, butylamino, etc, the above-mentioned lower alkanoylamino group or a lower alkylthio group sush as methylthio, ethylthio, propylthio, butylthio, etc.

In the compound of the invention, the compound having the pyridinio group for $R^3$ can be obtained by reacting the compound having the pyridyl group for $R^3$ with, for example, a lower alkyl halide, a cycloalkyl-lower alkyl halide, a lower alkoxy-lower alkyl halide, a lower alkanoyl-lower alkyl halide, a benzoyl-lower alkyl halide, a halogen-substituted lower alkyl halide, a lower alkyl halide substituted with halogen-substituted lower alkanoyl group, a carboxycarbonyl-lower alkyl halide, a lower alkyl halide substituted with lower alkoxyimino group, or a compound of the formula:

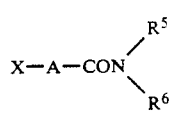

wherein A, $R^5$ and $R^6$ have the same meanings as difined above, and X is a halogen atom.

Examples of the halide moiety of the above-mentioned halide compounds include chloride, bromide, iodide and the like.

Representative examples of the compounds of the present invention which has the general formula given below are shown in the following table.

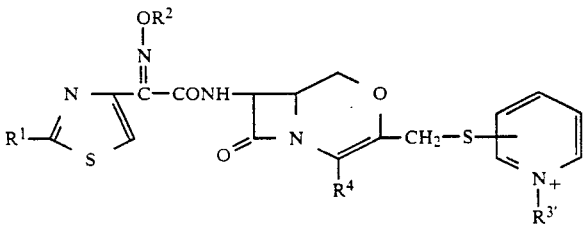
| | $R^1$ | $R^2$ | $R^{3'}$ | $R^4$ | Remarks |
|---|---|---|---|---|---|
| 1 | —NH₂ | —CH₃ | 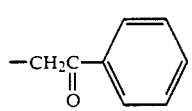 | —COO⁻ | |
| 2 | —NH₂ | —CH₃ | 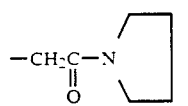 | —COO⁻ | |
| 3 | —NH₂ | —CH₃ | —CH₂CCH₃ ‖ O | —COO⁻ | |
| 4 | —NH₂ | 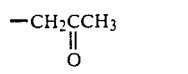 |  | —COO⁻ | |
| 5 | —NH₂ | 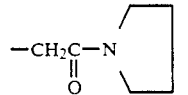 |  | —COO⁻ | |
| 6 | —NH₂ | —CH₂CNH₂ ‖ O | —CH₃ | —COO⁻ | |
| 7 | —NH₂ | —CH₃ | 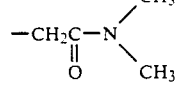 | —COO⁻ | |
| 8 | —NH₂ |  | —CH₂CC₂H₅ ‖ O | —COO⁻ | |
| 9 | —NH₂ | 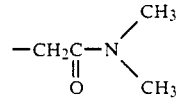 |  | —COO⁻ | |
| 10 | —NH₂ | 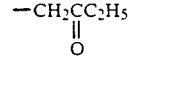 |  | —COO⁻ | |
| 11 | —NH₂ | —CH₃ | 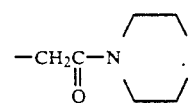 | —COO⁻ | |
| 12 | —NH₂ |  | —CH₂—Cl | —COO⁻ | |

-continued

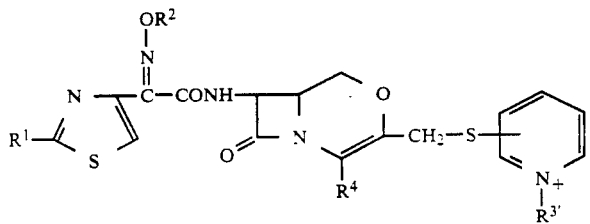

| | $R^1$ | $R^2$ | $R^{3'}$ | $R^4$ | Remarks |
|---|---|---|---|---|---|
| 13 | $-NHC(C_6H_5)_3$ | cyclopentyl | $-CH_2-Cl$ | $-COCH(C_6H_5)_2$ (O=) | iodide |
| 14 | $-NHC(C_6H_5)_3$ | cyclopentyl | $-CH_2$-cyclopropyl | $-COCH(C_6H_5)_2$ (O=) | bromide |
| 15 | $-NH_2$ | cyclopentyl | $-CH_2$-cyclopropyl | $-COO^-$ | |
| 16 | $-NHC(C_6H_5)_3$ | cyclopentyl | $-CH_2CH_2F$ | $-COCH(C_6H_5)_2$ (O=) | methanesulfonate |
| 17 | $-NH_2$ | cyclopentyl | $-CH_2CH_2F$ | $-COO^-$ | |
| 18 | $-NH_2$ | cyclohexyl | $-CH_2CH_2F$ | $-COO^-$ | |
| 19 | $-NHC(C_6H_5)_3$ | $-CH_3$ | $-CH_2CH_2F$ | $-COCH(C_6H_5)_2$ (O=) | methanesulfonate |
| 20 | $-NH_2$ | $-CH_3$ | $-CH_2CH_2F$ | $-COO^-$ | |
| 21 | $-NH_2$ | $-CH_2CN$ | $-CH_2C(=O)$-pyrrolidinyl | $-COO^-$ | |
| 22 | $-NH_2$ | $-CH_2CN$ | $-CH_2C(=O)N(CH_3)_2$ | $-COO^-$ | |
| 23 | $-NH_2$ | $-CH_2CN$ | $-CH_2C(=O)$-morpholinyl | $-COO^-$ | |
| 24 | $-NH_2$ | $-CH_2CN$ | $-CH_2CCH_3$ (O=) | $-COO^-$ | |
| 25 | $-NH_2$ | $-CH_3$ | $-CH_2C(=O)COOH$ | $-COO^-$ | |

-continued

[Structure: thiazole ring with R¹ substituent, =N-OR² oxime, CONH linked to β-lactam fused with oxazine ring bearing R⁴, CH₂-S-pyridinium with N⁺-R³']

| | R¹ | R² | R³' | R⁴ | Remarks |
|---|---|---|---|---|---|
| 26 | $-NH_2$ | $-CH_3$ | $-CH_2-\underset{\underset{O-CH_3}{\|\!\!N}}{C}-CH_3$ | $-COO^-$ | |
| 27 | $-NH_2$ | $-CH_3$ | $-CH_2-\underset{O}{\overset{\|}{C}}-CH_2F$ | $-COO^-$ | |
| 28 | $-NH_2$ | $-CH_3$ | $-CH_2OCH_3$ | $-COO^-$ | |
| 29 | $-NH_2$ | $-CH_3$ | $-CH_2\underset{O}{\overset{\|}{C}}-N\!\!\begin{pmatrix}\text{morpholine-S}\end{pmatrix}$ | $-COO^-$ | |
| 30 | $-NH_2$ | $-CH_3$ | $-CH_2\underset{O}{\overset{\|}{C}}-N\!\!\begin{pmatrix}\text{piperidine-OH}\end{pmatrix}$ | $-COO^-$ | |
| 31 | $-NH_2$ | $-CH_3$ | $-CH_2\underset{O}{\overset{\|}{C}}NHC_2H_5$ | $-COO^-$ | |
| 32 | $-NH_2$ | $-CH_3$ | $-CH_2\underset{O}{\overset{\|}{C}}-N\!\!\begin{pmatrix}\text{piperidine-CH}_3\end{pmatrix}$ | $-COO^-$ | |
| 33 | $-NH_2$ | $-CH_2COOH$ | $-CH_2\underset{O}{\overset{\|}{C}}-N\!\!\begin{pmatrix}\text{pyrrolidine}\end{pmatrix}$ | $-COO^-$ | |
| 34 | $-NH_2$ | $-CH_2CONH_2$ | — | $-\underset{O}{\overset{\|}{C}}OCH(C_6H_5)_2$ | |
| 35 | $-NHC(C_6H_5)_3$ | $-CH_2CONH_2$ | — | $-\underset{O}{\overset{\|}{C}}OCH(C_6H_5)_2$ | |
| 36 | $-NHCO-CH_2Cl$ | $-CH_3$ | $-CH_2\underset{O}{\overset{\|}{C}}-N\!\!\begin{pmatrix}\text{pyrrolidine}\end{pmatrix}$ | $-\underset{O}{\overset{\|}{C}}OCH(C_6H_5)_2$ | bromide |
| 37 | $-NH-CHO$ | $-CH_3$ | $-CH_2\underset{O}{\overset{\|}{C}}-N\!\!\begin{pmatrix}\text{pyrrolidine}\end{pmatrix}$ | $-\underset{O}{\overset{\|}{C}}OCH(C_6H_5)_2$ | bromide |
| 38 | $-NHCOO-CH_2C_6H_5$ | $-CH_3$ | $-CH_2\underset{O}{\overset{\|}{C}}-N\!\!\begin{pmatrix}\text{pyrrolidine}\end{pmatrix}$ | $-\underset{O}{\overset{\|}{C}}OCH(C_6H_5)_2$ | bromide |
| 39 | $-NHCOO-C(CH_3)_3$ | $-CH_3$ | $-CH_2\underset{O}{\overset{\|}{C}}-N\!\!\begin{pmatrix}\text{pyrrolidine}\end{pmatrix}$ | $-\underset{O}{\overset{\|}{C}}OCH(C_6H_5)_2$ | bromide |

-continued

| | R¹ | R² | R³' | R⁴ | Remarks |
|---|---|---|---|---|---|
| 40 | —NH₂ | 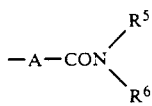 | —CH₂C(=O)—CH₃ | —COO⁻ | |

The compounds of the present invention can be produced by various processes, and the processes represented by the reaction scheme-1 to reaction scheme-6 may be mentioned by way of example.

Reaction scheme-1

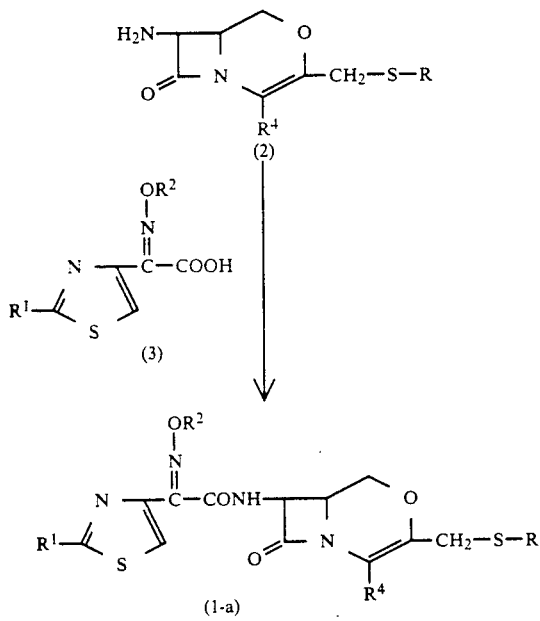

wherein $R^1$, $R^2$ and $R^4$ have the same meanings as defined above; and R is a pyridyl group or a pyridinio group, in which the pyridinio group is substituted with a lower alkyl group, a cycloalkyl-lower alkyl group, a lower alkoxy-lower alkyl group, a lower alkanoyl-lower alkyl group, a benzoyl-lower alkyl group, a halogen-substituted lower alkyl group, a lower alkyl group substituted with a halogen-substituted lower alkanoyl group, a carboxycarbonyl-lower alkyl group, a lower alkyl group substituted with a lower alkoxyimino group, or a group of the formula:

$$-A-CON\begin{matrix}R^5\\R^6\end{matrix}$$

in which A, $R^5$ and $R^6$ have the same meanings as defined above.

Referring to the above reaction scheme-1, the compound of the formula (1-a) can be produced by reacting the amine compound of the formula (2) with the carboxylic acid compound of the formula (3) or an activated compound at the carboxy group thereof by a conventional amide bond-forming reaction. This amide bond-forming reaction can be carried out by any of the methods known in the art, e.g.

a) The method involving the use of a condensing agent, wherein the carboxylic acid compound (3) is reacted with the amine compound (2) in the presence of a condensing agent.

b) The mixed acid anhydride method, wherein the carboxylic acid compound (3) is reacted with an alkyl halocarboxylate to give a mixed acid anhydride, which is then reacted with the amine compound (2).

c) The active ester method, wherein the carboxylic acid compound (3) is esterified into an active ester such as p-nitrophenyl ester, N-hydroxysuccinimide ester, 1-hydroxybenzotriazole ester or the like, which is then reacted with the amine compound (2).

d) The method in which the carboxylic acid compound (3) is treated with a dehydrating agent such as acetic anhydride to give a carboxylic acid anhydride, which is then reacted with the amine compound (2).

e) The method in which a lower alcohol ester of the carboxylic acid compound (3) is reacted with the amine compound (2) at elevated temperature and pressure.

f) The method in which the carboxylic acid compound (3) is converted to an acid halide, i.e. a carboxylic acid halide, which is then reacted with the amine compound (2).

An example of the amide bond-forming reaction is specifically described below.

The compound of the formula (1-a) according to the present invention can be obtained by reacting the amine compound of the formula (2) with the carboxylic acid compound of the formula (3) in the presence of a condensing agent, either in the absence of a solvent or in the presence of an inert solvent.

The condensing agent that can be employed in this reaction includes, for example, thionyl chloride, phosphorus oxychloride, phosphorus pentachloride, Vilsmeier reagent, for example, (chloromethylene)dimethylammonium chloride produced by reaction of demethylformamide with thionyl chloride, phosgen or phosphorous oxychloride, dicyclohexylcarbodiimide (DCC), 2,2'-pyridinyl disulfide-triphenylphosphine, and so on.

As examples of the solvent, there may be mentioned any solvent which does not adversely influence the reaction, for example, ethers such as diethyl ether, tetrahydrofuran, dioxane, etc., halogenated hydrocarbons such as dichloromethane, dichloroethane, chloroform, carbon tetrachloride, etc., aromatic hydrocarbons such as benzene, toluene, xylene, etc., amines such as pyridine, piperidine, triethylamine, etc., aliphatic hydrocarbons such as hexane, heptane, etc., alcohols such as methanol, ethanol, propanol, etc., aprotic polar solvents such as dimethylformamide (DMF), hexamethylphosphoric triamide (HMPA), dimethyl sulfoxide (DMSO), etc., carbon disulfide, and so on.

The above reaction is preferably carried out in the presence of a basic compound. As examples of such basic compound, there may be mentioned trialkylamines such as triethylamine, tributylamine, etc., such other organic bases as pyridine, picoline, 1,5-diazabicycl[4,3,0]nonene-5, 1,4-diazabicyclo[2,2,2]octane, 1,8-diazabicyclo[5,4,0]undecene-7, etc., monotrimethysilylacetamide, and inorganic bases such as alkali metal hydroxides, e.g. sodium hydroxide, potassium hydroxide, etc., alkali metal carbonates, e.g. sodium carbonte, potassium carbonate, alkali metal hydrogen carbonates, e.g. sodium hydrogen cabonate, potassium hydrogen carbonate, and so on.

In the above reaction, the carboxylic acid compound of the formula (3) and the amine compound of the formula (2) are present in a molar ratio of 1:1 to 10:1 and preferably 1:1 to 3:1. The basic compound and the amine compound of the formula (2) are present in a molar ratio of 1:1 to 40:1 and preferably 5:1 to 20:1.

The above reaction is conducted at about −20° C. to about 100° C., preferably about −20° C. to about 50° C., for about 30 minutes to about 24 hours, preferably about 30 minutes to about 10 hours.

The above procedure gives the compound of the formula (1-a) according to the present invention.

Referring to the above reaction between the amine compound of the formula (2) and the carboxylic acid compound of the formula (3), when the group $R^4$ is a carboxy group or a carboxylate group, there may be obtained, in certain cases, a compound such that the carboxy group or the carboxylate group of the product compound of the formula (1-a) is condensed with the carboxy group or the carboxylate group of the amine compound of the formula (2). In such cases, the compound of the formula (1-a) can be produced by hydrolyzing the condensation product compound in the presence of an acid catalyst such as an inorganic or organic acid, e.g. hydrochloric acid, hydrobromic acid, trifluoroacetic acid and the like.

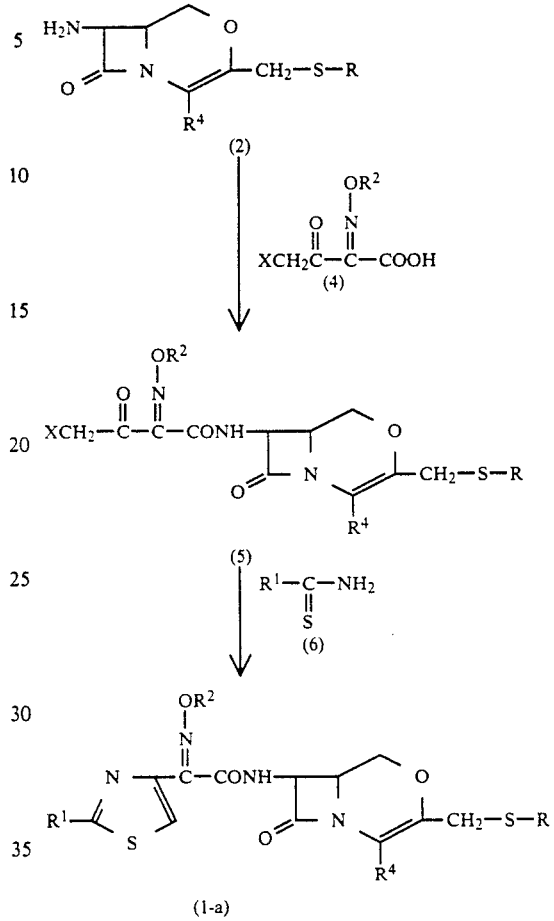

Reaction scheme-2 wherein $R^1$, $R^2$, $R^4$ and R have the same meanings as defined above; and X is a halogen atom.

Referring to the above reaction formula, the compound of the formula (5) can be obtained by reacting the amine compound of the formula (2) with the carboxylic acid compound of the formula (4). In the compound of the formula (4), examples of the halogen atom represented by X include chlorine, bromine, iodine and fluorine. This reaction can be conducted in the same manner as the amide bond-forming reaction between the amine compound of the formula (2) and the carboxylic acid compound of the formula (3) in accordance with the reaction scheme-1.

The compound of the formula (1-a) according to the present invention can be obtained by reacting the compound of the formula (5) obtained above with the thioacetamide compound of the formula (6) in the presence of a suitable solvent or in the absence of a solvent.

Many different types of solvents can be used in this reaction, and the same solvent as used according to the above-mentioned reaction scheme-1 can be employed.

In this reaction, the thioacetamide compound of the formula (6) and the compound of the formula (5) are present in a molar ratio of 1:1 to 10:1 and preferably 1:1 to 5:1. This reaction is conducted at −10° C. to 100° C., preferably −10° C. to 50° C., and completed generally in 1 to 50 hours, preferably in 1 to 10 hours.

Reaction scheme-3

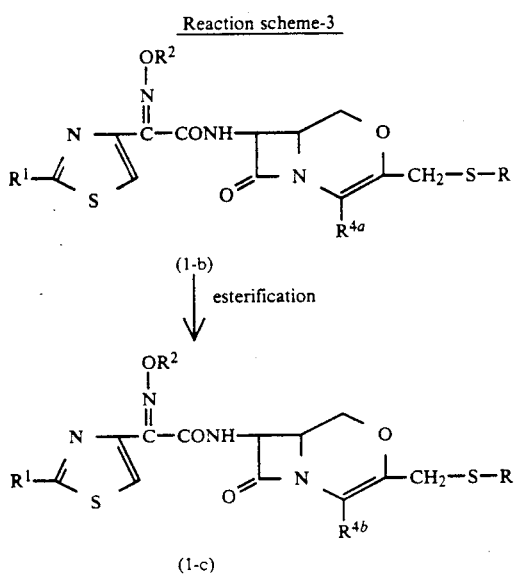

wherein $R^1$, $R^2$ and R have the same meanings as defined above; $R^{4a}$ is a carboxy group or a carboxylate group; and $R^{4b}$ is an esterified carboxy group. The ester compound of the formula (1-c) can be obtained by subjecting the compound of the formula (1-b) to a conventional esterification reaction.

By way of example, the above-mentioned esterification reaction is conducted in the presence of a catalyst, which may be one of the common esterification catalysts. Examples of such catalyst are inorganic acids such as hydrogen chloride, concentrated sulfuric acid, phosphoric acid, polyphosphoric acid, boron trifluoride, perchloric acid, etc., organic acids such as trifluoroacetic acid, trichloromethanesulfonic acid, naphthalenesulfonic acid, p-toluenesulfonic acid, benzenesulfonic acid, ethanesulfonic acid, etc.; acid anhydrides such as trichloromethanesulfonic anhydride, trifluoromethanesulfonic anhydride, etc., thionyl chloride, dimethylacetal, and so on. Cation exchange resins (acid form) can also be employed.

The above-mentioned esterification reaction can be conducted in the absence of a solvent or in the presence of a suitable solvent. The solvent to be used may be any of the solvents used in esterification reactions in general, being thus exemplified by aromatic hydrocarbons such as benzene, toluene, xylene, etc., halogenated hydrocarbons such as dichloromethane, dichloroethane, chloroform, carbon tetrachloride, etc., and ethers such as diethyl ether, tetrahydrofuran, dioxane, etc., and so on.

The catalyst and the compound of the formula (1-b) are present in a molar ratio of 1:1 to 100:1 and preferably 10:1 to 30:1. The reaction temperature is $-20°$ C. to 200° C. and preferably 0° to 150° C.

The compound of the formula (1-c) can also be produced by the following methods.

For example:

1) Condensation with salt elimination

This method comprises reacting an alkali (e.g. sodium, potassium) salt of the compound of the formula (1-b) with a halide compound corresponding to the ester residue of the esterified carboxy group for $R^{4b}$ and this reaction can be conducted in any type of solvent that does not interfere with the reaction, e.g. ethers such as dimethyl ether, diethyl ether, tetrahydrofuran, dioxane, etc., alcohols such as methanol, ethanol, etc., and aprotic polar solvents such as dimethylformamide (DMF), dimethyl sulfoxide (DMSO), hexamethylphosphoric triamide (HMPA), etc., and so on. The halide compound and the alkali metal salt of the compound (1-b) are present in a molar ratio of 1:1 at least and preferably 1:1 to about 3:1. This reaction is conducted at $-10°$ C. to 100° C. and preferably 0° C. to room temperature for about 1 to 12 hours.

2) Diazotization

This method comprises reacting the compound of the formula (1-b) with a diazo compound corresponding to the ester residue of the esterified carboxy group for $R^{4b}$, for example, diazomethane, phenyldiazomethane, diphenyldiazomethane, etc., in the presence of an inert solvent. As the inert solvent, there may be mentioned halogenated hydrocarbons such as dichloromethane, dichloroethane, chloroform, carbon tetrachloride, etc., ethers such as dimethyl ether, diethyl ether, tetrahydrofuran, dioxane, etc., nitro compounds such as nitromethane, nitrobenzene, etc., alcohols such as methanol, ethanol, etc., acetic acid esters such as methyl acetate, ethyl acetate, etc., alphatic hydrocarbons such as hexane, heptane, octane, etc., aprotic polar solvents such as dimethylformamide (DMF), dimethyl sulfoxide (DMSO), hexamethylphosphoric triamide (HMPA), etc., carbon disulfide, and so on.

The diazo compound should advisably be used in an amount of at least 1 mole, preferably about 1 to 3 moles, per mole of the compound of formula (1). The reaction proceeds smoothly at $-10°$ C. to room temperature and generally is completed in about 10 minutes to about 6 hours.

Reaction scheme-4

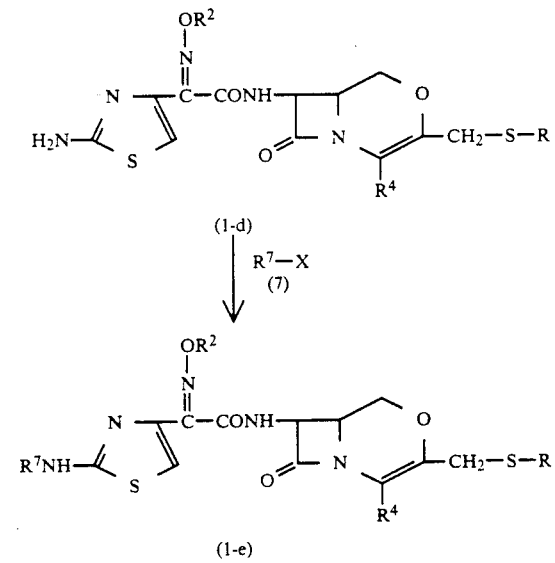

wherein $R^2$, $R^4$, R and X have the same meanings as defined above; and $R^7$ is a lower alkanoyl group, a halogen-substituted lower alkanoyl group, a phenyl-substituted lower alkyl group having 1 to 3 phenyl groups, a phenyl-lower alkoxycarbonyl group or a lower alkoxycarbonyl group.

The compound of the formula (1-e) can be obtained by reacting the compound of the formula (1-d) with the compound of the formula (7).

This reaction is carried out by reacting the compound of the formula (1-d) with the compound of the formula (7) in the presence of a basic compound and in the absence or presence of an inert solvent. It can be carried out in substantially the same manner as in the above-mentioned amide bond formation reaction according to reaction scheme-1. Therefore, the reaction mode and reaction conditions (e.g. basic compound, solvent, reaction temperature, reaction time, etc.) for this reaction may be the same as those as explained in the reaction scheme-1 mentioned before.

Reaction scheme-5

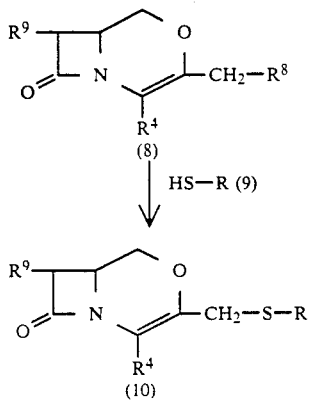

wherein $R^4$ and R have the same meanings as defined above $R^8$ is a halogen atom, a lower alkanesulfonyloxy group which may be substituted with a halogen atom, or an arylsulfonyloxy group which may be substituted with a lower alkyl group, a halogen atom or a nitro group; and $R^9$ is an azido group, an amino group, a protected amino group or a group of the formula:

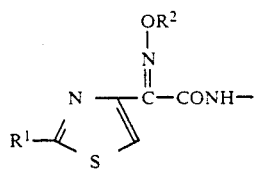

in which $R^1$ and $R^2$ have the same meanings as defined above.

The pyridine ring-containing thiomethyl groups can be introduced into the isocephem skeleton of the compound of the formula (8) at the 3-position thereof by a variety of methods. The above reaction scheme-5 exemplifies one method suited for that purpose.

Thus, reacting the compound of the formula (8) with the thiol compound of the formula (9) in a suitable inert solvent in the presence of a basic compound yields the compound of the formula (10) which comprises a portion of the compound of the present invention.

Referring to $R^8$ in the compound of the formula (8), the halogen atom means chlorine, bromine, iodine or fluorine, for instance, and the lower alkanesulfonyloxy group which may be substituted with a halogen atom may, for example, be methanesulfonyloxy, ethanesulfonyloxy, propanesulfonyloxy, trifluoromethanesulfonyloxy, etc., and the arylsulfonyloxy group which may be substituted with a lower alkyl group, a halogen atom or a nitro group may, for example, be benzenesulfonyloxy, toluenesulfonyloxy, p-chlorobenzenesulfonyloxy, p-nitrobenzenesulfonyloxy, etc.

Examples of the protected amino group for $R^9$ in the compound of the formula (8) include the above-mentioned lower alkanoylamino, halogen-substituted lower alkanoyl amino, halogen-substituted lower alkanoylamino, phenyl-substituted lower alkylamino having 1 to 3 phenyl groups, phenyl-lower alkoxycarbonylamino and lower alkoxycarbonylamino groups, phenyl-lower alkanoylamino groups having 2 to 6 carbon atoms in the alkanoyl moiety thereof such as phenylacetamido, 3-phenylpropionamido, 4-phenylbutyrylamido, etc., phthalimidos which may be substituted with a nitro group such as phthalimido, 4-nitrophthalimido, etc., and the like.

The basic compound used in the above reaction is exemplified by organic basic compounds such as tertiary amines, e.g. triethylamine, pyridine, etc., and inorganic basic compounds such as sodium carbonate, potassium carbonate and so on.

As the inert solvent, the solvents that may be used in the reaction according to the reaction scheme-1 given hereinbefore can be used.

The compound of the formula (9) and the compound of the formula (8) are present in a molar ratio of 1:1 at least and preferably 1:1 to 2:1. The basic compound and the compound of the formula (9) are present in a molar ratio of 1:1 at least and preferably 1:1 to 2:1. The reaction temperature is $-10°$ C. to 100° C. and preferably 0° to 50° C. Thus, the above reaction yields the compound of the formula (10).

When, in the compound according to the present invention and starting compounds, at least one of $R^1$ and $R^4$ represents a lower alkanoylamino group, a halogen-substituted lower alkanoylamino group, a phenyl-substituted lower alkylamino group having 1 to 3 phenyl group, a phenyl-lower alkoxycarbonylamino group or a lower alkoxycarbonylamino group, and an esterified carboxy group, respectively, the compound can be subjected to the deprotecting reaction shown below to give a compound with the elimination of 1 or more protective groups.

Reaction scheme-6

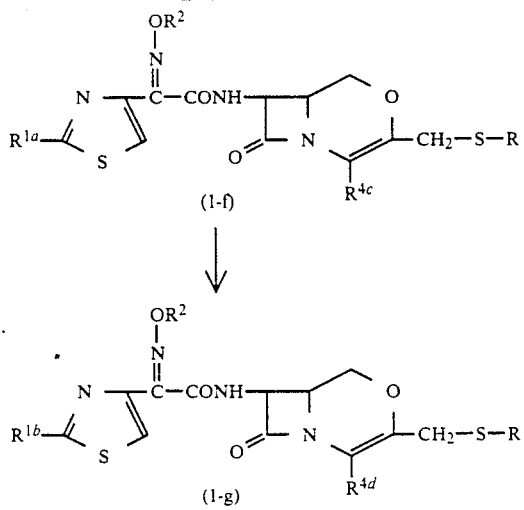

wherein $R^2$ and R have the same meanings as defined above; $R^{1a}$ and $R^{4c}$ have the same meanings as $R^1$ and $R^4$, respectively; provided that at least one of $R^{1a}$ and $R^{4c}$ represents a lower alkanoylamino group, a halogen-substituted lower alkanoylamino group, a phenyl-substituted lower alkylamino group having 1 to 3 phenyl groups, a phenyl-lower alkoxycarbonylamino group or a lower alkoxycarbonylamino group, and an esterified carboxy group, respectively, and $R^{1b}$ and $R^{4d}$ have the same meanings as $R^1$ and $R^4$, respectively; provided that at least one of $R^{1b}$ and $R^{4d}$ represents an amino group, and a carboxy group or a carboxylate group, respectively.

Referring to the above reaction scheme, the reation by which the compound of the formula (1-g) is produced from the compound of the formula (1-f) can be conducted by the method of reacting the compound of the formula (1-f) with an acidic compound or a basic compound, by subjecting the compound of the formula (1-f) to catalytic reduction, and so on, either in the absence of a solvent or in the presence of an inert solvent.

As examples of the inert solvent used in the above reaction, there may be mentioned halogenated hydrocarbons such as dichloromethane, dichloroethane, chloroform, carbon tetrachloride, etc., ethers such as dimethyl ether, diethyl ether, tetrahydrofuran, dioxane, anisole, etc.; nitro compounds such as nitromethane, nitrobenzene, etc.; alcohols such as methanol, ethanol, etc.; acetic acid esters such as ethyl acetate, methyl acetate, etc.; aliphatic hydrocarbons such as hexane, heptane, octane, etc.; aromatic hydrocarbons such as benzene, toluene, xylene, etc.; amines such as pyridine, piperidine, etc.; aprotic polar solvents such as dimethylformamide (DMF), hexamethylphosphoric triamide (HMPA), dimethyl sulfoxide (DMSO), etc.; carbon disulfide, water; and mixtures of water and the above-mentioned organic solvents.

As examples of the acid compound, there may be mentioned Lewis acids such as anhydrous aluminum chloride, stannic chloride, titanium tetrachloride, boron trichloride, boron trifluoride-ethyl ether complex, zinc chloride, etc., inorganic acids such as hydrochloric acid, nitric acid, sulfuric acid, etc., organic acids such as trichloroacetic acid, trifluoroacetic acid, methanesulfonic acid, acetic acid, etc., and acid-form ion exchange resins. The basic compound mentioned above is exemplified by organic bases such as trialkylamines, e.g. triethylamine, tributylamine, etc., pyridine, picoline, 1,5-diazabicyclo[4,3,0]nonene-5, 1,4-diazabicyclo[2,2,2]octane, 1,8-diazabicyclo[5,4,0]undecene-7, etc., and inorganic bases such as alkali metal hydroxides, e.g. sodium hydroxide, potassium hydroxide, etc., alkali metal carbonates, e.g. sodium carbonate, potassium carbonate, etc., and alkali metal hydrogen carbonates, e.g. sodium hydrogen carbonate, potassium hydrogen carbonate, and so on.

When the above reaction is carried out by the catalytic reduction method, the catalyst may be, for example, a platinum catalyst (e.g. platinum oxide, platinum black, platinum wire, platinum plate, platinum sponge, colloidal platinum, etc.), a palladium catalyst (e.g. palladium black, palladium chloride, palladium oxide, palladium-on-carbon, palladium-on-barium sulfate, palladium-on-barium carbonate, palladium sponge, etc.), a nickel catalyst (e.g. reduced nickel, nickel oxide, Raney nickel, etc.), a cobalt catalyst (e.g. reduced cobalt, Raney cobalt, etc.), an iron catalyst (e.g. reduced iron, Raney iron, etc.), or a copper catalyst (e.g. reduced copper, Raney copper, etc.), and so on.

When the acid compound or the basic compound is used in the above reaction, the acid or basic compound and the compound of the formula (1-f) are present in a molar ratio of 1:1 to 100:1 and preferably 1:1 to 20:1. This reaction is conducted at $-20°$ C. to $80°$ C., preferably $-10°$ C. to $50°$ C., and completed generally in 30 minutes to 48 hours, preferably in about 1 to 24 hours.

When the catalytic reduction method is used, the catalyst and the compound of the formula (1-f) are present in a molar ratio of 0.1:1 to 10:1 and preferably 0.1:1 to 1:1. This reaction is conducted at $0°$ to $200°$ C. and preferably $0°$ to $100°$ C., and completed in about 30 minutes to 48 hours and preferably in about 30 minutes to 6 hours.

The reaction according to the above reaction scheme-6 may be more specifically illustrated by way of the following reaction scheme-6a and 6b.

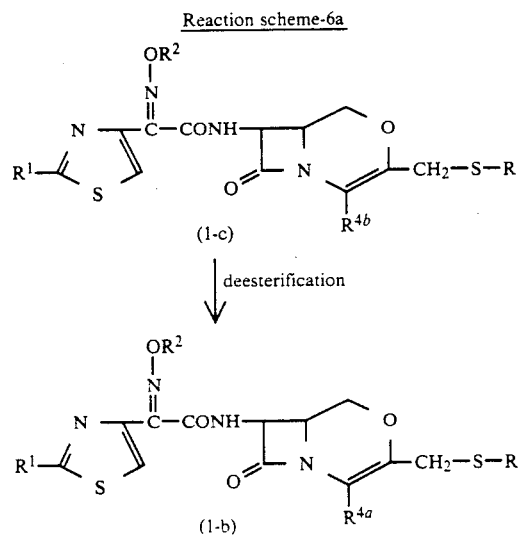

wherein $R^1$, $R^2$, R, $R^{4a}$ and $R^{4b}$ have the same meanings as defined above.

The carboxylic acid derivative of the formula (1-b) can be produced by subjecting the compound of the formula (1-c), i.e. an ester derivative in 4-position of the isocephem ring, to deesterification.

This deesterification reaction is conducted either without a solvent or in a suitable solvent, in the presence of a hydrolysis catalyst. The inert solvent and hydrolysis catalyst that are used in this reaction may be exemplified by the inert solvents and acid and basic compounds as explained in the reaction scheme-6.

This deesterification reaction can be carried out by the catalytic reduction method when the ester residue $R^{4b}$ is a residue that can be easily cleaved thereby, for example, a benzyl group, etc. The catalyst used in this catalytic reduction is exemplified by the catalysts as explained in the reaction scheme-6.

When an acid or a base is used in the above reaction, the acid or base and the compound of the formula (1-c) are present in a molar ratio of 1:1 to 100:1 and preferably 1:1 to 20:1. This reaction is conducted at $-20°$ C. to $80°$ C., preferably at $-10°$ C. to $50°$ C., and can be carried to completion in 30 minutes to 48 hours, preferably in 1 to 24 hours.

When the catalytic reduction method is employed, the catalytic reduction catalyst and the compound of the formula (1-c) are present in a molar ratio of 0.1:1 to 10:1 and preferably 0.1:1 to 1:1. This reaction is conducted at $0°$ to $200°$ C., preferably $0°$ to $100°$ C. and may be carried to completion in 30 minutes to 48 hours, preferably about 30 minutes to about 6 hours.

Reaction scheme-6b

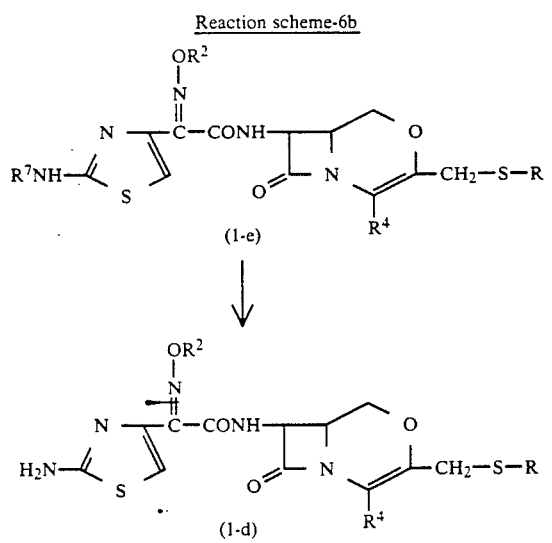

wherein $R^2$, $R^4$, R and $R^7$ have the same meanings as defined above.

The compound of the formula (1-d), wherein the substituent in 2-position of the thiazolyl group is an amino group, can be produced by subjecting the compound of the formula (1-e), wherein the substituent in 2-position of the thiazolyl group is a substituted amino group, to a reaction which is substantially similar to the deesterification reaction according to the aforementioned reaction scheme-6a. Thus, for example, an acid compound or a basic compound may be permitted to act on the starting compound or the starting compound is subjected to catalytic reduction, either in the absence of a solvent or in the presence of a suitable solvent.

Many different types of solvents can be used in this reaction and the solvents exemplified in the reaction scheme-6 can be employed for the purposes of this reaction.

The acid compound mentioned just above may be selected from among the acid compounds exemplified in the reaction scheme-6 but preferably be an inorganic acid such as hydrochloric acid, hydrobromic acid, sulfuric acid, nitric acid, etc., an organic acid such as trifluoroacetic acid, acetic acid, formic acid, etc., or an ion exchange resin of the acid-form. Of these acid compounds, those which are liquid can be utilized as the reaction solvent as well.

As examples of the basic compounds, there may be mentioned organic bases such as trialkylamines, e.g. triethylamine, tributylamine, etc., pyridine, picoline, 1,5-diazabicyclo[4,3,0]nonene-5, 1,4-diazabicyclo[2,2,2]octane, 1,8-diazabicyclo[5,4,0]undecene-7, etc., inorganic bases such as alkali metal hydroxides, e.g. sodium hydroxide, potassium hydroxide, etc., alkali metal carbonates, e.g. sodium carbonate, potassium carbonate, etc., and alkali metal hydrogen carbonates, e.g. sodium hydrogen carbonate, potassium hydrogen carbonate, etc., and urea compounds such as thiourea and urea.

When water is added to the reaction system, its proportion relative to the acid or basic compound is preferably in the range of 10 to 80 v/v percent and it is advantageous to add a further amount, 10 to 20 volumes, of water at completion of the reaction.

The acid or basic compound and the compound of the formula (1-e) are present in a molar ratio of 1:1 to 100:1 and preferably 2:1 to 10:1. The reaction temperature is $-20°$ C. to 80° C. and preferably $-10°$ C. to 50° C. The reaction time is about 1 to 24 hours.

When the reaction according to the reaction scheme-6b is carried out by the catalytic reduction method, the conditions (for example, the type and amount of catalytic reduction catalyst, solvent, reaction temperature and time, etc.) may be the same as those of catalytic reduction mentioned hereinbefore in the reaction scheme-6a.

The above procedure yields the amine compound of the formula (1-d).

In the compound of the formula (1), the compound having the pyridinio group for $R^3$ can be obtained by reacting the corresponding compound with, for example, a lower alkyl halide, a cycloalkyl-lower alkyl halide, a lower alkoxy-lower alkyl halide, a lower alkanoyl-lower alkyl halide, a benzoyl-lower alkyl halide, a halogen-substituted lower alkyl halide, a lower alkyl halide substituted with halogen-substituted lower alkanoyl group, a carboxycarbonyl-lower alkyl halide, a lower alkyl halide substituted with lower alkoxyimino group, or a compound of the formula:

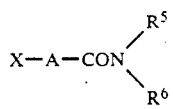

wherein A, $R^5$, $R^6$ and X have the same meanings as defined above, in the presence of an inert solvent. Examples of the halide moiety of the above-mentioned halide compounds include chloride, bromide, iodide and the like. Examples of the inert solvent to be used in the reaction include halogenated hydrocarbons such as dichloromethane, dichloroethane, chloroform, carbon tetrachloride, etc., aromatic hydrocarbons such as benzene, toluene, xylene, etc., and ethers such as diethyl ether, tetrahydrofuran, dioxane, etc. The reaction is carried out at room temperature to about 100° C., preferably at about 50° to about 80° C. and is completed in about 2 to about 8 hours. The above-mentioned halide compound is preferably used in an amount of about 1 to 1.5 moles per mole of the corresponding compound.

After the reaction, the halogen ion may be eliminated to give an inner salt by purification by column chromatography using Diaion HP-20 (manufactured by Mitsubishi Chemical Industries), Amberlite XAD-2 (manufactured by Rohm and Haas), etc.

Referring to the reaction schemes 1 to 6 mentioned above, the starting compounds of the formula (2) and formula (8) include novel compounds and can be produced by the following reaction processes.

Reaction scheme-7

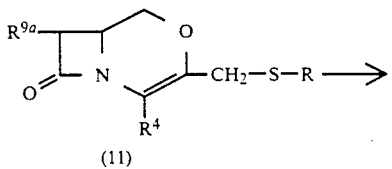

-continued
Reaction scheme-7

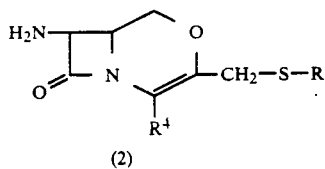

(2)

wherein $R^4$ and $R$ have the same meanings as defined above; and $R^{9a}$ is an azido group or a protected amino group.

According to this reaction scheme-7, the compound of the formula (11) is subjected to reduction, hydrolysis or hydrazinolysis according to the nature of substituent $R^{9a}$ to give the compound of the formula (2) which includes novel compounds.

Referring to the above reaction, when the group $R^{9a}$ is an azido group, the amine compound of the formula (2) is produced by permitting a reducing agent to act on the compound of the formula (11) in the absence of a solvent or in the presence of a suitable inert solvent.

The solvent to be used in this reaction is exemplified by halogenated hydrocarbons such as dichloromethane, dichloroethane, chloroform, carbon tetrachloride, etc., aromatic hydrocarbons such as benzene, toluene, xylene, etc., ethers such as diethyl ether, tetrahydrofuran, dioxane, etc., and amines such as triethylamine, pyridine, etc.

The reducing agent may, for example, be hydrogen sulfide. When hydrogen sulfide, for instance, is employed, it is preferable to add an amine such as triethylamine, pyridine or the like.

The reducing agent and the compound of the formula (11) are present in a molar ratio of 1:1 to 100:1 and preferably 3:1 to 50:1. This reaction is conducted generally at $-30°$ C. to $50°$ C. and preferably at $-10°$ C. to $10°$ C., and completed in about 30 minutes to 10 hours.

When the group $R^{9a}$ is a protected amino group such as a lower alkanoylamino group, a halogen-substituted lower alkanoylamino group, a phenyl-substituted lower alkylamino group having 1 to 3 phenyl groups, a phenyl-lower alkoxycarbonylamino group, a lower alkoxycarbonyl amino group and a phenyl-lower alkanoylamino group, the amine compound of the formula (2) can be produced by subjecting the compound of the formula (11) to hydrolysis in the absence of a solvent or in the presence of an inert solvent.

This reaction can be carried out substantially in the same manner as the reaction according to the reaction scheme-6b. Thus, the reaction procedure and conditions (for example, the hydrolysis catalyst, solvent, reaction temperature, reaction time, etc.) for this reaction may be the same as those as explained in the reaction scheme-6b mentioned before.

When the group $R^{9a}$ is a phthalimido group which may be substituted with a nitro group, the amine compound of the formula (2) can be produced by subjecting the compound of the formula (11) to hydrazinolysis, i.e. reaction with hydrazine or a hydrazine derivative, in the absence of a solvent or in the presence of an inert solvent.

The inert solvent to be used in this reaction include halogenated hydrocarbons such as dichloromethane, dichloroethane, chloroform, carbon tetrachloride, etc., and alcohols such as methanol, ethanol, etc. The hydrazine derivative is exemplified by lower alkyl-substituted hydrazine such as methylhydrazine, ethylhydrazine, etc., and aryl-substituted hydrazine such as phenylhydrazine, etc.

The hydrazine or hydrazine derivative and the compound of the formula (11) are present in a molar ratio of 1:1 at least and preferably 1:1 to 2:1. This reaction is conducted generally at $0°$ to $100°$ C. and preferably at $0°$ to $80°$ C., and completed in about 1 to about 40 hours.

When, in the compound of the formula (2) obtained by the above reaction, the group $R^4$ is an esterified carboxy group, the compound can be deesterified in substantially the same manner as the deesterification reaction according to the reaction scheme-6a to give a compound wherein $R^4$ is a carboxy group or a carboxylate group. When the group $R^4$ is a carboxy group or a carboxylate group, the compound of the formula (2) can be esterified in substantially the same manner as the esterification reaction according to the reaction scheme-3 given hereinbefore to give a compound wherein $R^4$ is an esterified carboxy group.

Reaction scheme-8

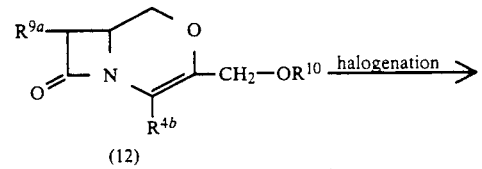

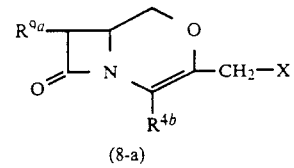

wherein $R^{4b}$, $R^{9a}$, and X have the same meanings as defined above; and $R^{10}$ is a hydrogen atom or a lower alkanoyl group.

The reaction is a halogenation reaction which substitutes the alcoholic hydroxy group or lower alkanoyloxy group of the compound of the formula (12) with a halogen atom and can be conducted under the various halogenating conditions commonly adopted.

By way of illustration, when the group $R^{10}$ is a hydrogen atom, the compound of the formula (12) can be reacted with a thionyl halide such as thionyl chloride, thionyl bromide, thionyl iodide or the like in the presence or absence of a solvent to give the compound of the formula (8-a). As the solvent, any solvent that does not interfere with the reaction can employed. For example, halogenated hydrocarbons such as dichloromethane, dichloroethane, chloroform, carbon tetrachloride, etc., ethers such as dimethyl ether, diethyl ether, tetrahydrofuran, dioxane, etc., nitro compounds such as nitromethane, nitrobenzene, etc., acetic acid esters such as ethyl acetate, methyl acetate, etc., aliphatic hydrocarbons such as hexane, heptane, octane, etc., aprotic polar solvents such as dimethylformamide (DMF), dimethyl sulfoxide (DMSO), hexamethylphosphoric triamide (HMPA), etc., and carbon disulfide may be mentioned. The thionyl halide and the compound of the formula (12) are present in molar ratio of 1:1 at least and preferably 1:1 to 2:1. This reaction is conducted at $-10°$ C. to room temperature and preferably under ice-cooling, and completed in about 5 minutes to about 1 hour.

In conducting this reaction, a basic compound such as pyridine, dimethylaniline, triethylamine or the like is preferably added as an acid acceptor to the reaction system.

When the group $R^{10}$ is a lower alkanoyl group, the compound of the formula (12) can be reacted with a tri(lower alkyl)silyl halide in the absence of a solvent or in the presence of an inert solvent to give the compound of the formula (8-a).

The inert solvent to be used in this reaction is the same as exemplified above. Examples of the tri(lower alkyl)silyl halide include trimethylsilyl chloride and triethylsilyl chloride, for instance.

The tri(lower alkyl)silyl halide and the compound of the formula (12) are present in a molar ratio of 1:1 at least and preferably 1:1 to 2:1. This reaction is conducted at −20° C. to 50° C., preferably at room temperature, and is completed in about 30 minutes to about 5 hours.

Among the compounds of the formula (1) according to the invention, optically active compounds can be produced from optically active starting materials in accordance with the reaction schemes 1 to 6 mentioned before, and the product compounds have steric configurations corresponding to those of the starting compounds.

The following is an exemplary process for the production of an optically active starting compound. The steric configuration illustrated by the following reaction scheme is only an example and when a cis- or trans-isomer is used, for instance, there can be obtained a product compound having the corresponding configuration.

Reaction scheme-9

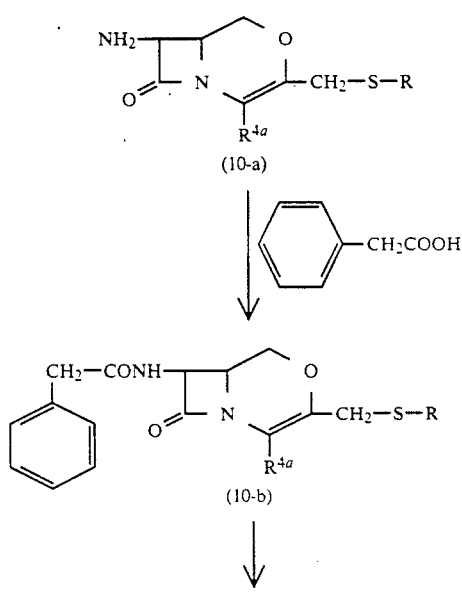

-continued
Reaction scheme-9

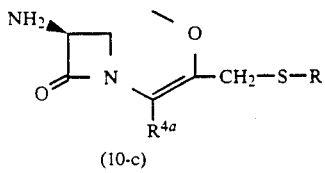

wherein $R^{4a}$ and R have the same meanings as defined above.

Referring to the above reaction scheme, the reaction by which the compound of the formula (10-b) is produced from the compound of the formula (10-a) is carried out by reacting the compound of the formula (10-a) with phenylacetic acid or a reactive derivative at the carboxy group thereof. This reaction can be conducted in substantially the same manner as the reaction according to the aforementioned reaction scheme-1. Therefore, the acylation conditions (for example, the reactive derivative, solvent, reaction temperature, reaction time, etc.) for this reaction may be the same as those as exemplified in the reaction scheme-1.

The reaction by which the compound of the formula (10-c) is produced from the compound of the formula (10-b) is such that the phenylacetamido group in the 7-position of the compound of the formula (10-b) is selectively hydrolyzed by means of an enzyme to give &he compound of the formula (10-c).

This reaction is conducted in water or an aqueous solvent in the presence of an enzyme. The enzyme used in this reaction may be any enzyme that will selectively hydrolyze the amido group, being thus exemplified by penicillin G amidase, etc.

The proportion of the enzyme relative to the compound of the formula (10-b) is generally about 0.5 to 2 gram equivalents. As the reaction system is rendered acidic by the by-product acid with the progress of the reaction, a basic compound is preferably added to the reaction system so as to maintain the system at the optimal pH for the enzyme. The basic compound is exemplified by, for example, aqueous ammonia, alkali metal hydroxides such as sodium hydroxide, potassium hydroxide, etc., alkali metal carbonates or alkali metal hydrogen carbonates such as sodium carbonate, potassium carbonate, sodium hydrogen carbonate, etc. This reaction is preferably conducted at the optimal temperature for the enzyme used, and is carried to completion in 1 to 10 hours and preferably in about 1 to about 5 hours.

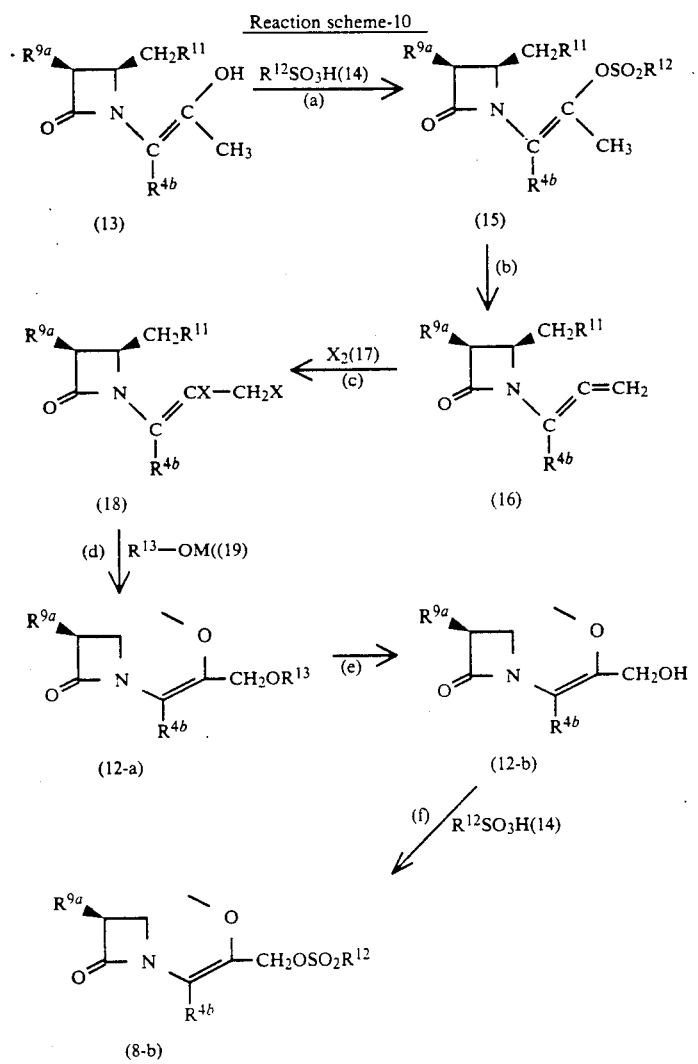

Reaction scheme-10 wherein $R^{4b}$, $R^{9a}$ and X have the same meanings as defined above; $R^{11}$ is a halogen atom, a lower alkanesulfonyloxy group which may be substituted with a halogen atom or an arylsulfonyloxy group which may be substituted with a lower alkyl group, a halogen atom or a nitro group; $R^{12}$ is a lower alkyl group which may optionally be substituted with halogen or an aryl group which may optionally be substituted with lower alkyl, halogen and/or nitro; $R^{13}$ is a lower alkanoyl group; and M is an alkali metal.

Referring to the above reaction scheme, the reaction (a) by which the compound of the formula (15) is produced from the compound of the formula (13) is carried out by reacting the compound of the formula (13) with a sulfonic acid of the formula (14) or a reactive derivative at the sulfo group thereof in the presence of an inert solvent or in the absence of a solvent.

The inert solvent is exemplified by halogenated hydrocarbons such as dichloromethane, dichloroethane, chloroform, carbon tetrachloride, etc., ethers such as dimethyl ether, diethyl ether, etc., and aliphatic hydrocarbons such as hexane, heptane, octane, etc.

In the compound of the formula (13), suitable examples of the group for $R^{11}$ include the aforesaid halogen atom, lower alkanesulfonyloxy group which may be substituted with halogen atom, and arylsulfonyloxy group which may be substituted with lower alkyl, halogen atom or nitro group, as exemplified for the group $R^8$.

The sulfonic acid compound represented by the formula (14) is exemplified by lower alkanesulfonic acids such as methanesulfonic acid, ethanesulfonic acid, propanesulfonic acid, etc., halogen-substituted lower alkanesulfonic acids such as trifluoromethanesulfonic acid, 2-trifluoroethanesulfonic acid, etc., and arylsulfonic acids which may optionally be substituted with lower alkyl, halogen and/or nitro, such as benzenesulfonic acid, toluenesulfonic acid, p-chlorobenzenesulfonic acid, p-nitrobenzenesulfonic acid, etc. The reactive derivative at the sulfo group of the sulfonic acid is exemplified by sulfonic acid halides such as sulfonyl chloride, sulfonyl bromide, etc., and sulfonic anhydride.

The sulfonic acid or the reactive derivative at the sulfo group thereof and the compound of the formula (13) are present in a molar ratio of 1:1 at least and preferably 1:1 to 1.5:1. This reaction is conducted at $-50°$ C. to ice-cooling conditions and completed in about 1 to about 50 minutes. This reaction can be carried out in the presence of an acid acceptor such as pyridine, triethylamine, etc., but it is preferable to add the acid acceptor at completion of the above reaction and continue the reaction further for about 30 minutes to 3 hours, preferably for about 1 hour. The acid acceptor and the reactive derivative of the sulfonic acid are present in a molar ratio of 1:1 at least and preferably 1:1 to about 1.5:1.

The reaction (b) by which the compound of the formula (16) is produced from the compound of the formula (15) obtained above is carried out by reacting the compound of the formula (15) with a basic compound such as triethylamine, pyridine, piperidine or the like in the presence of an inert solvent or in the absence of a solvent. The inert solvent to be used may be one that is used in the above reaction step(a). The basic compound and the compound of the formula (15) are present in a molar ratio of 1:1 at least and preferably 1:1 to about 1.5:1. This reaction is carried out under ice-cooling to room temperature conditions and carried to completion in about 10 minutes to about 2 hours, preferably in about 1 hour.

This reaction (c) by which the compound of the formula (18) is produced from the compound of the formula (16) is such that a halogen molecule represented by the formula (17) is added to the compound of the formula (16). The halogen molecule and the compound of the formula (16) are present in a molar ratio of 1:1 at least and preferably 1:1 to 1.2:1. The halogen molecule is preferably iodine molecule. This reaction is conducted under ice-cooling to room temperature conditions and carried to completion in about 1 to about 5 hours, preferably in about 3 hours.

The reaction (d) by which the compound of the formula (12-a) is produced from the compound of the formula (18) is carried out by reacting the compound of the formula (18) with a lower alkanoic acid alkali metal salt of the formula (19) such as sodium formate, potassium formate, sodium acetate, potassium acetate, sodium propionate or the like, in a mixture of water and an organic solvent exemplified in the above reaction step (a).

The proportion of water in the mixed solvent is about 0.1 to about 1 vol % based on the organic solvent. The lower alkanoic acid alkali metal salt of the formula (19) and the compound of the formula (18) are present in a molar ratio of 1:1 to 6:1 and preferably 4:1 to 5:1. This reaction is conducted at room temperature and completed in about 6 to about 24 hours.

The reaction (e) by which the compound of the formula (12-b) is produced from the compound of the formula (12-a) is carried out by reacting the compound of the formula (12-a) with a mineral acid such as hydrochloric acid, nitric acid, sulfuric acid or the like, in the presence of an inert solvent or in the absence of a solvent. The inert solvent to be used in the reaction is exemplified by water, ketones such as acetone, diethyl ketone, acetophenone, etc., ethers such as diethyl ether, tetrahydrofuran, dioxane, etc., halogenated hydrocarbons such as dichloromethane, dichloroethane, chloroform, carbon tetrachloride, etc., aromatic hydrocarbons such as benzene, toluene, xylene, etc., amines such as pyridine, piperidine, triethylamine, etc., aliphatic hydrocarbons such as hexane, heptane, etc., alcohols such as methanol, ethanol, propanol, etc., aprotic polar solvents such as dimethylformamide (DMF), dimethyl sulfoxide (DMSO), hexamethylphosphoric triamide (HMPA), etc., and carbon disulfide. The mineral acid and the compound of the formula (12-a) are present in a molar ratio of about 3:1. This reaction is conducted at room temperature and completed in about 1 to about 10 hours.

The reaction (f) by which the compound of the formula (8-b) is produced from the compound of the formula (12-b) is carried out by reacting the compound of the formula (12-b) with the sulfonic acid of the formula (14) or a reactive derivative at the sulfo group thereof in the presence of a basic compound such as pyridine, triethylamine or the like. This reaction can be conducted in the same manner as the aforesaid reaction step (a).

The use of the compound of the formula (13) in which the 3- and 4-positions of the azetidinone ring are (R, R), (R, S) and (S, R) give the compounds of the formula (8-b) having the corresponding steric configurations.

The compound of the formula (13) can be produced by the following reaction processes.

Reaction scheme-11

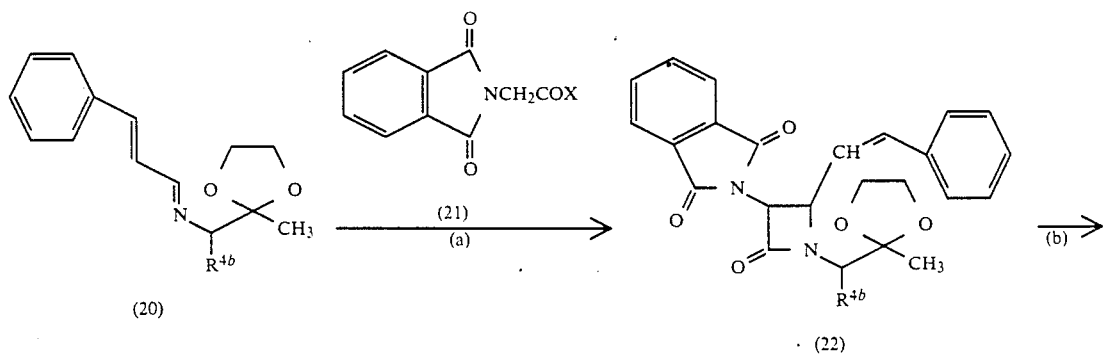

5,037,976
-continued
Reaction scheme-11
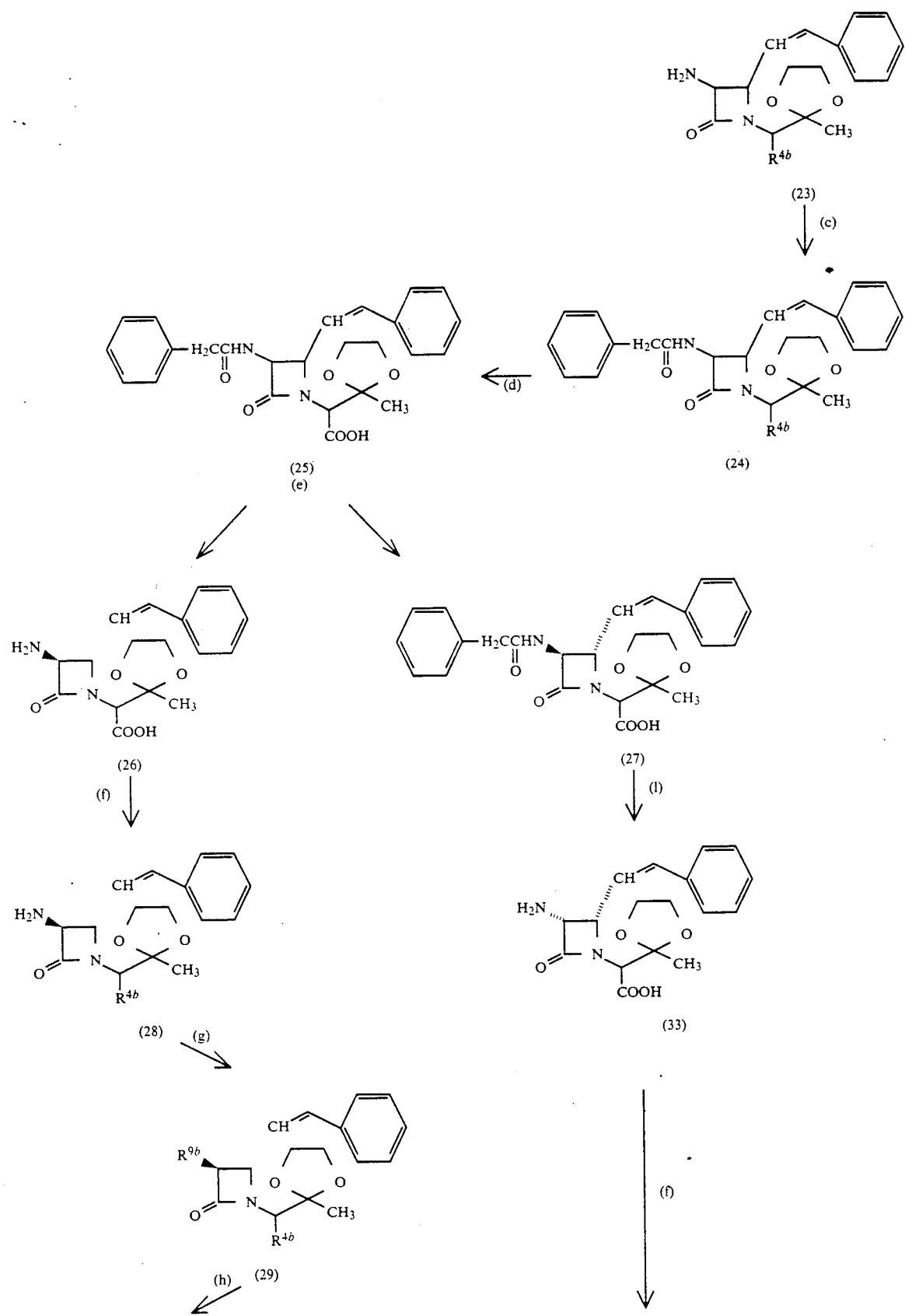

-continued
Reaction scheme-11

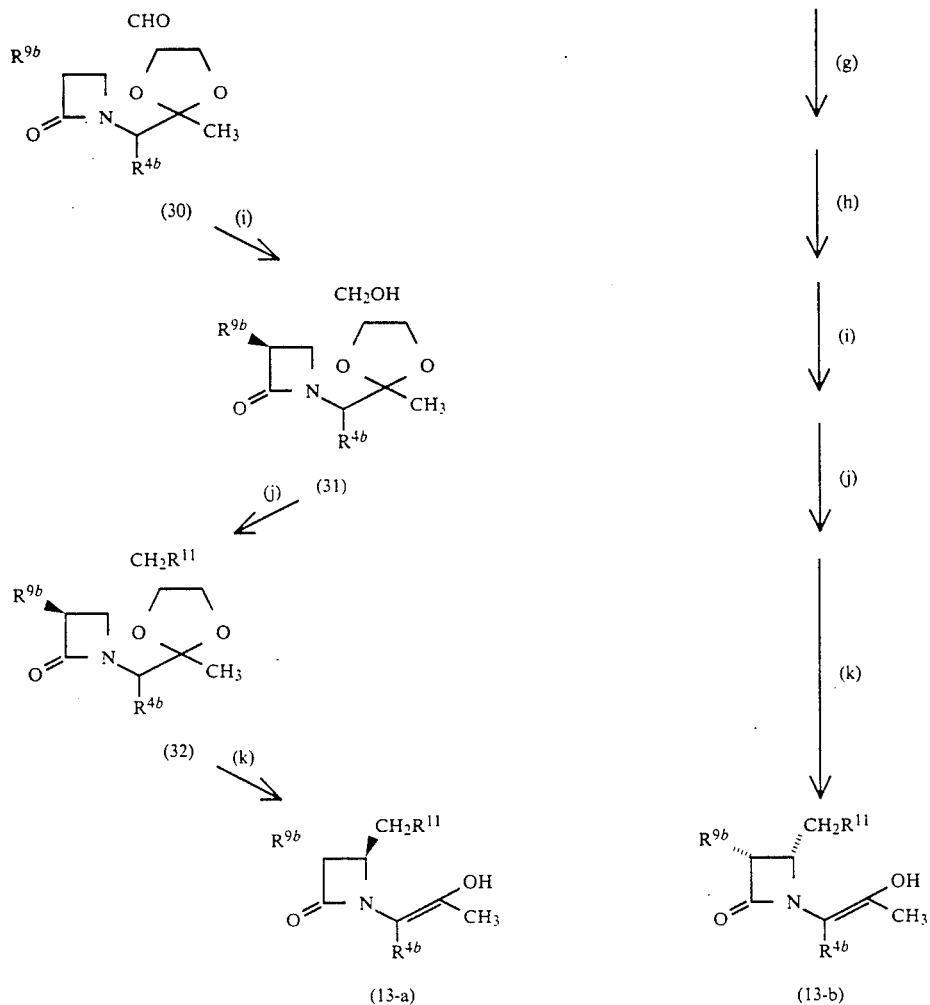

wherein $R^{4b}$, $R^{11}$ and X have the same meanings as defined above; and $R^9$ is a protected amino group.

Referring to the above reaction scheme, the reaction (a) by which the compound of the formula (22) is produced from the compound of the formula (20) is carried out by reacting the compound of the formula (20) with the compound of the formula (21) in the absence or presence of a basic compound. Examples of the basic compound to be used include inorganic bases such as alkali metal hydroxide, e.g. sodium hydroxide, potassium hydroxide, etc., and alkali metal carbonates or alkali metal hydrogen carbonates, e.g. sodium carbonate, potassium carbonate, sodium hydrogen carbonate, etc., and organic bases such as triethylamine, pyridine, N,N-dimethylaniline, etc. The reaction is usually conducted in an organic solvent. Examples of the solvent to be used include aromatic hydrocarbons such as benzene, toluene, xylene, etc., ethers such as diethyl ether, tetrahydrofuran, etc., and halogenated hydrocarbons such as methylene chloride, dichloroethane, chloroform, etc. The compound of the formula (21) and the compound of the formula (20) are present in a molar ratio of 1:1 at least and preferably 1:1 to about 2:1. This reaction is conducted at about −50° C. to room temperature, preferably at about −30° C. to about 0° C., for about 1 to about 10 hours, preferably about 30 minutes to about 6 hours.

The reaction (b) by which the compound of the formula (23) is produced from the compound of the formula (22) is carried out by reacting the compound of the formula (22) with hydrazine or a derivative thereof. This reaction can be carried out in substantially the same manner as the hydrazinolysis according to the reaction scheme-7 mentioned before. Therefore, reaction conditions (for example, the reactants, solvent, reaction temperature and time, etc.) for this reaction may be the same as those as exemplified in the above-mentioned reaction scheme-7.

The reaction (c) by which the compound of the formula (24) is produced from the compound of the formula (23) is carried out by reacting the compound of the formula (23) with phenylacetic acid or a reactive derivative at the carboxy group thereof. This reaction is carried out in substantially the same manner as the reaction according to the reaction scheme-1 mentioned before. Therefore, reaction procedures (for example, the method using a condensing agent, the mixed acid anhydride method, the active ester method, etc.) and reaction conditions (for example, the basic compound, solvent, reaction temperature, reaction time, etc.) for this reaction may be the same as those as exemplified in the reaction scheme-1 mentioned before.

The reaction (d) by which the compound of the formula (25) is produced from the compound of the formula (24) is carried out by subjecting the compound of the formula (24) to deesterification in the presence of a basic compound and an inert solvent.

Examples of the inert solvent to be used in the above reaction include water, alcohols such as methanol, ethanol, propanol, isopropanol, etc., and ethers such as diethyl ether, dioxane, tetrahydrofuran, etc. Examples of the basic compound include alkali metal hydroxides such as sodium hydroxide, potassium hydroxide, etc., alkali metal carbonates such as sodium carbonate, potassium carbonate, etc., and alkali metal alkoxides such as sodium methoxide, sodium ethoxide potassium ethoxide, etc. This reaction is conducted at about 0° C. to 100° C., preferably about 0° C. to room temperature, and completed in about 1 to about 10 hours.

The reaction (e) which yields the compound of the formula (26) and the compound of the formula (27) from the compound of the formula (25) is carried out by permitting an enzyme capable of cleaving an amido linkage to act upon the compound of the formula (25). This reaction is carried out in substantially the same manner as the reaction of converting the compound of the formula (10-b) to the compound of the formula (10-c) in accordance with the above-mentioned reaction scheme-9. Therefore, reaction conditions (for example, the enzyme to be used, solvent, pH of reaction system, reaction temperature, reaction time, etc.) for this reaction may be the same as those as exemplified in the reaction scheme-9 mentioned before. After this reaction, the compound from which the amido linkage has been cleaved enzymatically and the compound whose amido linkage remains intact are separated from each other to give the compound of the formula (26) and the compound of the formula (27), respectively.

The reaction (f) by which the compound of the formula (28) is produced from the compound of the formula (26) is carried out by esterifying the compound of the formula (26). This reaction is conducted in substantially the same manner as the esterification according to the above-mentioned reaction scheme-3. Therefore, reaction conditions (for example, the acid catalyst, solvent, reaction temperature, reaction time, etc.) for this reaction may be the same as those as exemplified in the reaction scheme-3 mentioned before.

The reaction (g) by which the compound of the formula (29) is produced from the compound of the formula (28) is carried out by reacting the compound of the formula (28) with phenylacetic acid or a reactive derivative at the carboxy group thereof, with phthalic acid or a reactive derivative thereof, or with the compound of the formula (7).

The reaction between the compound of the formula (28) and phenylacetic acid or a reactive derivative at the carboxy group thereof is conducted in substantially the same manner as the reaction according to the aforementioned reaction scheme-1. Therefore, reaction procedures (for example, the method using a condensing agent, the mixed acid anhydride method, the active ester method, etc.) and reaction conditions (for example, the basic compound, solvent, reaction temperature, reaction time, etc.) for this reaction may be the same as those as exemplified in the reaction scheme-1 mentioned before.

The reaction between the compound of the formula (28) and phthalic acid or a reactive derivative thereof is generally conducted in a solvent. The reactive derivative of phthalic acid is exemplified by phthalic anhydride, N-(esterified carboxy)phthalimides such as N-methoxycarbonylphthalimide, N-ethoxycarbonylphthalimide, N-phenoxycarbonylphthalimide, etc., and 2-(esterified carboxy)benzoyl halides such as 2-methoxycarbonylbenzoyl chloride, 2-ethoxycarbonylbenzoyl chloride, 2-phenoxycarbonylbenzoyl chloride, etc.

When phthalic acid is used in the above reaction, the reaction can be conducted in substantially the same manner as the reaction according to the aforementioned reaction scheme-1. Therefore, reaction procedures (for example, the method using a condensing agent, the mixed acid anhydride method, the active ester method, etc.) and reaction conditions (for example, the solvent, reaction temperature, reaction time, etc.) for this reaction may be the same as those as exemplified in the reaction scheme-1 mentioned before.

When phthalic anhydride is used, the reaction is conducted in an inert solvent. Examples of the inert solvent include halogenated hydrocarbons such as dichloromethane, dichloroethane, chloroform, carbon tetrachloride, etc., ethers such as dimethyl ether, diethyl ether, dioxane, tetrahydrofuran, etc., aromatic hydrocarbons such as benzene, toluene, xylene, etc., and aliphatic hydrocarbons such as hexane, heptane, octane, etc. In this reaction, the phthalic anhydride and the compound of the formula (28) are present in a molar ratio of 1:1 at least and preferably 1:1 to 2:1. The reaction is conducted at room temperature to 100° C., preferably at about 40° to about 80° C.

When the N-(esterified carboxy)phthalimide is employed, the reaction is conducted in an inert solvent in the presence of a basic compound.

Examples of the inert solvent to be used in this reaction include water, alcohols such as methanol, ethanol, propanol, etc., and ethers such as dimethyl ether, diethyl ether, dioxane, tetrahydrofuran, etc. Examples of the basic compound include inorganic bases such as alkali metal hydroxides, e.g. sodium hydroxide, potassium hydroxide, etc., and alkali metal carbonates or alkali metal hydrogen carbonates such as sodium carbonate, potassium carbonate, sodium hydrogen carbonate, etc., and organic bases such as triethylamine, pyridine, N,N-dimethylaniline, etc.

The N-(esterified carboxy)phthalimide and the compound of the formula (28) are present in a molar ratio of 1:1 at least and preferably 1:1 to 2:1. The basic compound and the compound of the formula (28) are present in a molar ratio of 1:1 to 10:1. This reaction is conducted at 0° to 50° C., preferably at room temperature, and completed in about 1 to about 5 hours.

When the 2-(esterified carboxy)benzoyl halide is employed, the reaction is conducted in an inert solvent in the presence of a basic compound.

Examples of the inert solvent to be used in this reaction include halogenated hydrocarbons such as dichloromethane, dichloroethane, chloroform, carbon tetrachloride, etc., ethers such as dimethyl ether, diethyl ether, dioxane, tetrahydrofuran, etc., aromatic hydrocarbons such as benzene, toluene, xylene, etc., and aliphatic hydrocarbons such as hexane, heptane, octane, etc. Examples of the basic compound include inorganic bases such as alkali metal hydroxides, e.g. sodium hydroxide, potassium hydroxide, etc., and alkali metal carbonates and alkali metal hydrogen carbonates such as sodium carbonate, potassium carbonate, sodium hydrogen carbonate, etc., and organic bases such as triethylamine, pyridine, N,N-dimethylaniline, etc.

The 2-(esterified carboxy)benzoyl halide and the compound of formula (28) are present in a molar ratio of 1:1 at least and preferably 1:1 to 2:1. This reaction is conducted at 0° C. to room temperature and completed in about 1 to about 5 hours.

The reaction between the compound of the formula (28) and the compound of the formula (7) is conducted in substantially the same manner as the reaction according to the aforementioned reaction scheme-4. Therefore, reaction mode and conditions (for example, basic compound, solvent, reaction temperature, reaction time, etc.) for this reaction may be the same as those as exemplified in the reaction scheme-4 mentioned before.

The order of the reactions (f) and (g) may be reversed. Thus, it is possible to first subject the compound of the formula (26) to this reaction and, then, carry out the aforesaid esterification to give a compound of the formula (29).

The reaction (h) by which the compound of the formula (30) is produced from the compound of the formula (29) is carried out by oxidizing the compound of the formula (29) with ozone in the presence of an inert solvent. Examples of the inert solvent include halogenated hydrocarbons such as methylene chloride, dichloroethane, chloroform, etc., and alcohols such as methanol, ethanol, etc. The amount of ozone to be used is at least equimolar amount, generally an excess, relative to the compound of the formula (29). The reaction is conducted at −100° C. to 0° C. and preferably at −50° C. to −30° C. While the reaction time varies with the feeding rate Of ozone, reaction temperature, etc., the reaction is generally continued until an excess of ozone is detected in the reaction system (for example, the blue color of ozone is detected). After the reaction, an inert gas such as nitrogen gas is optionally introduced to remove the excess ozone and an after-treatment with a reducing agent is preferably carried out. Examples of the reducing agent include dimethyl sulfide, sodium borohydride, sodium sulfite and so on. This after-treatment is generally carried out under cooling to at room temperature.

The reaction (i) by which the compound of the formula (31) is produced from the compound of the formula (30) is a reaction that reduces the aldehyde group of the compound of the formula (30) to a hydroxy group, and any of the known procedures for reducing an aldehyde group to a hydroxy group can be utilized. By way of example, this reaction is carried out by reacting the compound of the formula (30) with a reducing agent in the presence of a solvent Examples of the solvent to be used in this reaction include ethers such as diethyl ether, tetrahydrofuran, dioxane, etc., and alcohols such as methanol, ethanol, etc. Examples of the reducing agent include borohydride compounds (e.g. sodium borohydride, lithium borohydride, sodium cyanoborohydride, tetramethylammonium borohydride, diborane, etc.), and aluminum hydride compounds (e.g. lithium aluminum hydride, sodium aluminum hydride, aluminum hydride, lithium trimethoxyaluminum hydride, lithium tri-t-butoxyaluminum hydride, etc.). This reaction is conducted at −60° C. to room temperature, preferably at −30° C. to −10° C. and carried to completion in about 1 to about 10 hours, preferably in about 1 to about 5 hours.

The reaction (j) by which the compound of the formula (32) is produced from the compound of the formula (31) is carried out by reacting the compound of the formula (31) with a halogenating agent, or with a sulfonic acid corresponding to $R^{11}$ or a reactive derivative at the sulfo group thereof, in the presence of a solvent. Examples of the solvent to be used in this reaction include aromatic hydrocarbons such as benzene, toluene, etc., ethers such as diethyl ether, tetrahydrofuran, etc., halogenated hydrocarbons such as methylene chloride, chloroform, dichloroethane, etc., aprotic polar solvents such as dimethylformamide, dimethyl sulfoxide, hexamethylphosphoric triamide, etc., and acetonitrile.

The aforesaid sulfonic acid and the reactive derivative at the sulfo group thereof are exemplified by the sulfonic acid compounds and reactive derivatives mentioned hereinbefore in the reaction scheme-10 step (a). The sulfonic acid or its reactive derivative and the compound of the formula (31) are present in a molar ratio of 1:1 at least and preferably 1:1 to about 1.5:1. This reaction is preferably carried out in the presence of a base. The base is exemplified by the organic or inorganic basic compounds mentioned in the reaction step (a) described above, although the use of an organic base is preferred. This reaction is conducted generally at −10° C. to 100° C., preferably at 0° to room temperature, and carried to completion in about 1 to about 20 hours, preferably in about 1 to about 10 hours.

The halogenation reaction of the compound of the formula (31) can be conducted in substantially the same manner as the halogenation reaction of the hydroxy group according to the aforementioned reaction scheme-8. Therefore, reaction procedures and conditions (for example, halogenating agent, solvent, reaction temperature, reaction time, etc.) for this reaction may be the same as those as exemplified in the reaction scheme-8 mentioned before.

The reaction (k) by which the compound of the formula (13-a) is produced from the compound of the formula (32) is carried out by reacting the compound of the formula (32) with an acid compound in the presence or absence of a solvent. Examples of the acid to be used include mineral acids such as hydrochloric acid, sulfuric acid, nitric acid, etc., organic acids such as acetic acid, trifluoroacetic acid, p-toluenesulfonic acid, methanesulfonic acid, etc., Lewis acids such as aluminum chloride, titanium tetrachloride, tin tetrachloride, zinc chloride, etc., and compounds containing phenolic hydroxy groups such as phenol, cresol, etc. The amount of the acid compound to be used is generally an excess relative to the compound of the formula (32). The solvent that can be used is exemplified by organic acids such as acetic acid, etc., alcohols such as methanol, ethanol, etc., aprotic polar solvents such as dimethylformamide, dimethyl sulfoxide, hexamethylphosphoric triamide, etc., and acetonitrile. When the above acid compound is a liquid, it can be utilized as the reaction solvent as well. This reaction is conducted at about −20° C. to about 80° C., preferably at about 0° C. to room temperature, and is carried to completion in about 1 to about 10 hours, preferably in about 1 to about 5 hours.

The reaction (l) by which the compound of the formula (33) is produced from the compound of the formula (27) is carried out by subjecting the compound of the formula (27) to a reaction causing elimination of the phenylacetyl group. This reaction can be conducted in substantially the same manner as the reaction according to the aforementioned reaction scheme-6b. Therefore, reaction procedures and conditions (for example, the acid compound, solvent, reaction temperature, reaction time, etc.) for this reaction may be the same as those as exemplified in the reaction scheme-6b mentioned before.

The reaction by which the compound of the formula (13-b) is produced from the compound of the formula (33) is carried out by subjecting the compound of the formula (33) to the aforementioned reactions (f), (g), (h), (i), (j) and (k), subsequently, and reference may be made to the description of reaction precedures and conditions given hereinbefore in connection with the respective reaction steps.

In addition, the invention provides a novel process for preparing azetidinone compounds of the following formulas which are useful as intermediates for the synthesis of 2-oxa-isocephem compounds.

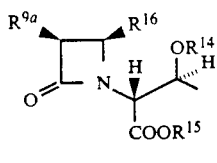
(34-a)

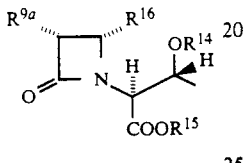
(34-b)

wherein $R^{9a}$ has the same meaning as defined above; $R^{14}$ is a hydrogen atom or a hydroxy-protective group; $R^{15}$ is a hydrogen atom or a carboxy-protective group; and $R^{16}$ is a group of the formula:

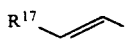

or a group of the formula:

$R^{17}$—COOCH$_2$— in the above formula, $R^{17}$ is a lower alkyl group or a aryl group which may be substituted with a halogen atom, a lower alkyl group, a nitro group or a halogen-substituted lower alkyl group.

The compounds of the formulas (34-a) and (34-b) include known compounds described in, for example, Canadian J. of Chemistry, 56, 1335, (1978) and novel compounds.

However, the processes for preparing azetidinone compounds already known in the prior arts have a defect that the yields are low because of requiring so many reaction steps or that azetidinone compounds having a cis-configuration at the 3- and 4-positions thereof cannot be obtained selectively.

In view of the problems, an intensive study undertaken by the inventors has resulted in the development of a novel process for preparing selectively azetidinone compounds having a cis-configuration at the 3- and 4-position thereof in a high yield in less steps.

The process can be shown in the following reaction scheme-12.

Reaction scheme-12

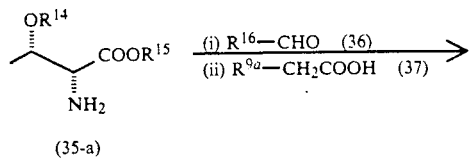
(35-a)

-continued
Reaction scheme-12

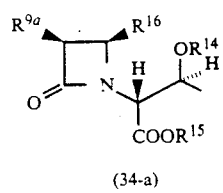
(34-a)

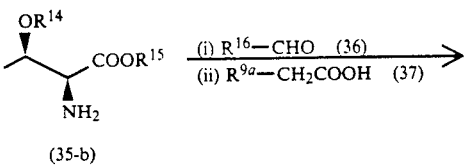
(35-b)

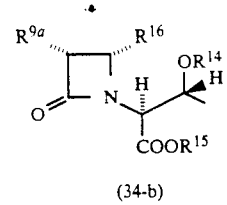
(34-b)

wherein $R^{9a}$, $R^{14}$, $R^{15}$ and $R^{16}$ have the same meanings as defined above.

The groups give in terms of symbols in the above formulas (34-a), (34-b), (35-a), (35-b), (36) and (37) are respectively described in more detail in the following.

Examples of the lower alkyl group include alkyl groups having 1 to 6 carbon atoms, such as methyl, ethyl, propyl, butyl, isobutyl, tert-butyl, pentyl, hexyl and the like.

Examples of the halogen atom include chlorine, bromine, fluorine and iodine.

Examples of the halogen-substituted lower alkyl group include halogen-substituted alkyl groups containing 1 to 3 halogen atoms and 1 to 6 carbon atoms in the alkyl moiety, such as chloromethyl, bromomethyl, iodomethyl, fluoromethyl, dichloromethyl, dibromomethyl, difluoromethyl, trichloromethyl, tribromomethyl, trifluoromethyl, 2-chloroethyl, 2-bromoethyl, 2-fluoroethyl, 1,2-dichloroethyl, 2,2-difluoroethyl, 1-chloro-2-fluoroethyl, 2,2,2-trifluoroethyl, 2,2,2-trichloroethy, 3-fluoropropyl, 3,3,3-trichloropropyl, 4-chlorobutyl, 5-chloropentyl, 6-chlorohexyl, 3-chloro-2-methylpropyl and the like.

Examples of the hydroxy-protective group include phenyl-lower alkyl groups containing 1 to 6 carbon atoms in the alkyl moiety and 1 to 3 phenyl groups optionally having a substituent selected from the group consisting of a lower alkoxy group having 1 to 6 carbon atoms, a nitro group, a halogen atom and a cyano group, such as benzyl, α-phenethyl, β-phenethyl, 3-phenylpropyl, benzhydryl, trityl, 4-methoxybenzyl, 4-nitrobenzyl, 2-nitrobenzyl, 4-chlorobenzyl, 4-cyanobenzyl and the like; lower alkanoyl groups having 1 to 6 carbon atoms such as formyl, acetyl, propionyl, butyryl, isobutyryl, pentanoyl, pivaloyl, hexanoyl and the like; halogen-substituted lower alkanoyl groups containing 1 to 3 halogen atoms and 2 to 6 carbon atoms in the alkanoyl moiety, such as monochloroacetyl, monofluoroacetyl, monobromoacetyl, monoiodoacetyl, dichloroacetyl, trichloroacetyl, tribromoacetyl, 3-chloropropionyl, 2,3-dichlopropionyl, 3,3,3-trichloropropionyl, 4-chlorobutyryl, 5-chloropentanoyl, 6-chlorohexanoyl, 3-fluoropropionyl, 4-fluorobutyryl and the like; phenyl-lower alkoxycarbonyl groups having 1 to 6 arbon atoms in the alkoxy moiety, such as 1-phenylethoxycarbonyl, 2-phenylethoxycarbonyl, 3-phenylpropoxycarbonyl, 4-phenylbutoxycarbonyl, 5-phenylpentyloxycarbonyl, 6-phenylhexyloxycarbonyl and the like; lower alkoxycarbonyl groups having 1 to 6 carbon atoms in the alkoxy moiety, such as methoxycarbonyl, ethoxycarbonyl, propoxycarbonyl, isopropoxycarbonyl, butoxycarbonyl, tert-butoxycarbonyl, pentyloxycarbonyl, hexyloxycarbonyl and the like; lower alkenyloxycarbonyl groups having 2 to 6 carbon atoms in the alkenyloxy moiety, such as vinyloxycarbonyl, allyloxycarbonyl and the like; phenyl-lower alkanoyl groups having 1 to 6 carbon atoms in the alkanoyl moiety and a phenyl group optionally having on the phenyl group, 1 to 3 substituents selected from the group consisting of a nitro group, a lower alkyl group having 1 to 6 carbon atoms and a halogen atoms, such as benzoyl, phenylacetyl, 3-phenylpropionyl, 4-phenylbutyryl, 5-phenylpentanoyl, 6-phenylhexanoyl, 3-phenyl-2-methylpropionyl, 4-nitrophenylacetyl, 4-methylphenylacetyl, 4-chlorophenylacetyl, 3-nitrophenylacetyl, 3,4-dimethylphenylacetyl, 2-methylphenylacetyl and the like; lower alkyl groups having 1 to 6 carbon atoms, such as methyl, ethyl, propyl, butyl, tert-butyl, pentyl, hexyl and the like; lower alkoxy-lower alkyl groups containing an alkoxy moiety of 1 to 6 carbon atoms and an alkyl moiety of 1 to 6 carbon atoms, such as methoxymethyl, ethoxymethyl, butoxymethyl, 2-methoxyethyl, 2-ethoxyethyl, 1-methyl-1-methoxyethyl, 1-isopropoxyethyl and the like; tetrahydropyranyl groups optionally having a lower alkyl group of 1 to 6 carbon atoms or a halogen atom, such as tetrahydropyranyl, 4-methyltetrahydropyranyl, 4-bromotetrahydropyranyl and the like; and organic silyl groups such as trimethylsilyl, triethylsilyl, isopropyldimethylsilyl, triphenylsilyl, tribenzylsilyl and the like.

Examples of the carboxy-protective group include lower alkyl groups having 1 to 6 carbon atoms such as methyl, ethyl, propyl, isopropyl, butyl, isobutyl, tert-butyl, pentyl, hexyl and the like; and mono- or diphenyl-lower alkyl groups having 1 to 6 carbon atoms in the alkyl moiety, such as benzyl, benzhydryl, α-phenethyl, β-phenethyl, α,β-diphenylethyl, 3-phenylpropyl, 4-phenylbutyl, 5-phenylpentyl, 6-phenylhexyl and the like.

The phenyl moiety in the said mono- or diphenyl-lower alkyl group may be optionally substituted by a substituent such as halogen atom (e.g. chlorine atom, bromine atom, fluorine atom, iodine atom, etc.), lower alkyl group having 1 to 6 carbon atoms (e.g. methyl, ethyl, propyl, isopropyl, butyl, isobutyl, tert-butyl, pentyl, hexyl, etc.), lower alkoxy group having 1 to 6 carbon atoms (e.g. methoxy, ethoxy, propoxy, isopropoxy, butoxy, tert-butoxy, pentyloxy, hexyloxy, etc.) or nitro group.

Examples of the aryl group which may be substituted with a halogen atom, a lower alkyl group, a nitro group or a halogen-substituted lower alkyl group include aryl groups optionally substituted with a halogen atom, an alkyl group having 1 to 6 carbon atoms, a nitro group or a halogen-substituted alkyl group having 1 to 6 carbon atoms, such as 4-chlorophenyl, 3-chlorophenyl, 2-chlorophenyl, 2,4-dichlorophenyl, 3,5-dichlorophenyl, 3,4,5-trichlorophenyl, 4-bromophenyl, 3-bromophenyl, 2-bromophenyl, 3,5-dibromophenyl, 4-fluorophenyl, 3-fluorophenyl, 2-fluorophenyl, 4-iodophenyl, 3-iodophenyl, 2-iodophenyl, 2-chloro-1-naphthyl, 5-chloro-1-naphthyl, 1-chloro-2-naphthyl, 4-bromo-1-naphthyl, 8-fluoro-1-naphthyl, 4-tolyl, 3-tolyl, 2-tolyl, 2,4-dimethylphenyl, 2,6-dimethylphenyl, 3,4,5-trimethylphenyl, 2,4,6-trimethylphenyl, 4-ethylphenyl, 3-ethylphenyl, 2-ethylphenyl, 2,4-diethylphenyl, 4-propylphenyl, 3-propylphenyl, 4-isopropylphenyl, 4-butylphenyl, 4-pentylphenyl, 4-hexylphenyl, 2-methyl-1-naphthyl, 4-methyl-1-naphthyl, 8-methyl-1-naphthyl, 1-methyl-2-naphthyl, 4-ethyl-2-naphthyl, 4-nitrophenyl, 3-nitrophenyl, 2-nitrophenyl, 3,4-dinitrophenyl, 2-nitro-1-naphthyl, 8-nitro-2-naphthyl, 4-chloromethylphenyl, 3-chloromethylphenyl, 2-chloromethylphenyl, 3,4-di(chloromethyl)phenyl, 4-bromomethylphenyl, 3-bromomethylphenyl, 2-bromomethylphenyl, 4-iodomethylphenyl, 3-iodomethylphenyl, 2-iodomethylphenyl, 4-fluoromethylphenyl, 3-fluoromethylphenyl, 2-fluoromethylphenyl, 4-dichloromethylphenyl, 4-dibromomethylphenyl, 4-difluoromethylphenyl, 4-trichloromethylphenyl, 4-trifluoromethylphenyl, 4-(2-chloroethyl)phenyl, 4-(1,2-dichloroethyl)phenyl, 4-(2-fluoroethyl)phenyl, 4-(2,2-difluoroethyl)phenyl, 4-(2,2,2-trifluoroethyl)phenyl, 4-(3-fluoropropyl)phenyl, 4-(3,3,3-trichloropropyl)phenyl, 4-(4-chlorobutyl)phenyl, 4-(5-chloropentyl)phenyl, 4-(6-chlorohexyl)phenyl, 4-(3-chloro-2-methylpropyl)phenyl, 4-chloromethyl-1-naphthyl, 8-fluoromethyl-1-naphthyl, 2-trifluoromethyl-1-naphthyl, 8-trifluoromethyl-1-naphthyl and the like.

Examples of the protected amino group include lower alkanoylamino groups having 1 to 6 carbon atoms, such as formylamino, acetylamino, propionylamino, butyrylamino, isobutyrylamino, pentanoylamino, hexanoylamino and the like; lower alkanoylamino groups having 2 to 6 carbon atoms and substituted with 1 to 3 halogen atoms, such as monochloroacetylamino, monofluoroacetylamino, monobromoacetylamino, monoiodoacetylamino, dichloroacetylamino, trichloroacetylamino, tribromoacetylamino, 3-chloropropionylamino, 2,3-dichloropropionylamino, 3,3,3-trichloropropionylamino, 4-chlorobutyrylamino, 5-chloropentanoylamino, 6-chlorohexanoylamino, 3-fluoropropionylamino, 4-fluorobutyrylamino and the like; phenyl-lower-alkylamino groups containing 1 to 6 carbon atoms in the alkyl moiety and 1 to 3 phenyl groups, such as benzylamino, α-phenethylamino, β-phenethylamino, 3-phenylpropylamino, benzhydrylamino, tritylamino and the like; phenyl-lower-alkoxycarbonylamino groups having 1 to 6 carbon atoms in the alkoxy moiety, such as 1-phenylethoxycarbonylamino, 2-phenylethoxycarbonylamino, 3-phenylpropoxycarbonylamino, 4-phenylbutoxycarbonylamino, 5-phenylpentyloxycarbonylamino, 6-phenylhexyloxycarbonylamino and the like; lower alkoxycarbonylamino groups having 1 to 6 carbon atoms in the alkoxy moiety, such as methoxycarbonylamino, ethoxycarbonylamino, propoxycarbonylamino, isopropoxycarbonylamino, butoxycarbonylamino, tert-butoxycarbonylamino, pentyloxycarbonylamino, hexyloxycarbonylamino and the like; and phthalimido groups optionally having a nitro group such as phthalimido, 4-nitrophthalimido and the like.

In the above reaction scheme-12, the reaction of the compound of the formula (35-a) or (35-b) and the compound of the formula (36) is carried out in the presence or absence of a solvent.

As examples of the solvent, there may be mentioned any solvent which does not adversely influence the reaction, for example, ethers such as diethyl ether, tetrahydrofuran, dioxane, etc., halogenated hydrocarbons such as dichloromethane, dichloroethane, chloroform, carbon tetrachloride, etc., aromatic hydrocarbons such as benzene, toluene, xylene, etc., amines such as pyridine, piperidine, triethylamine, etc., aliphatic hydrocarbons such as hexane, heptane, etc., alcohols such as methanol, ethanol, propanol, etc., aprotic polar solvents such as dimethylformamide (DMF), hexamethylphosphoric triamide (HMPA), dimethyl sulfoxide (DMSO), etc., carbon disulfide and the like.

The reaction may be preferably carried out in the presence of a dehydrating agent. Examples of the dehydrating agent include various customary dehydrating agents such as desiccants conventionally used for the dehydration of solvents (e.g. molecular sieve, etc.,), mineral acids such as hydrogen chloride, sulfuric acid, boron trifluoride, etc., organic acids such as p-toluenesulfonic acid, benzenesulfonic acid, etc., silylating agents such as tri(lower)alkylsilylacetamide (e.g. N,O-bis(trimethylsilyl)acetamide, etc.) and the like.

The amount of the compound of the formula (36) to be used is not limited particularly, but at least equimolar amount, preferably 1 to 2 mols of the compound of the formula (36) per mol of the compound of the formula (35-a) or (35-b) is used. The amount of the dehydrating agent to be used is also not limited in particular. However, when a desiccant is used, its amount is ordinarily excessive to the compound of the formula (35-a) or (35-b). When an acid is used, its amount is a catalytic amount to the compound of the formula (35-a) or (35-b).

The reaction is carried out generally at 0° C. to 80° C., preferably room temperature to about 60° C., and completed in about 1 to about 10 hours.

Thus-obtained compound can be used for the further reactions with or without isolation or purification.

The reaction of the resulting product with the compound of the formula (37) or its reactive derivative at the carboxy group is carried out in the presence or absence of a basic compound. Examples of the reactive derivative at the carboxy group of the compound of the formula (37) include acid halides such as chloride, bromide, etc.; acid azides; activated esters such as cyanomethyl ester, p-nitrophenyl ester, 2,4-dinitrophenyl ester, pentachlorophenyl ester, phenylthio ester, p-nitrophenylthio ester, etc., and the like.

Examples of the basic compound used in the present reaction include inorganic bases such as alkali metal hydroxides (e.g. sodium hydroxide, potassium hydroxide, etc.), alkali metal carbonate or hydrogencarbonates (e.g. sodium carbonate, potassium carbonate, sodium hydrogencarbonate, etc.), organic bases such as triethylamine, pyridine, N,N-dimethylaniline, etc., and the like. The reaction is carried out usually in an organic solvent. Examples of the solvent to be used include aromatic hydrocarbons such as benzene, toluene, etc., ether such as diethyl ether, tetrahydrofuran, etc., halogenated hydrocarbons such as dichloromethane, chloroform, etc., and the like, and the halogenated hydrocarbons are preferred.

The suitable amount of the compound of the formula (37) to be used is at least equimolar amount, preferably 1 to 1.5 mols of the compound of the formula (37) per mol of the compound obtained by the reaction of the compound of the formula (35-a) or (35-b) and the compound of the formula (36).

The reaction is carried out at $-70°$ C. to $0°$ C., preferably at about $-40°$ C. to about $-20°$ C., and completed in 1 to 10 hours, preferably about 1 to about 5 hours.

Thus, the compound of the formula (34-a) or (34-b) having a cis-configuration at the 3- and 4-positions of the azetidinone skeleton can be prepared stereoselectively in a high yield, especially the process of the invention gives the desired compound in a high optical purity (about 80% enantiomeric excess or above).

Preferable embodiment of the process of the invention will be explained below. The compound of the formula (35-a) or (35-b) in which is hydrogen atom is allowed to react with a silylating agent such as trimethylsilyl chloride, triethylsilyl chloride, isopropyldimethylsilyl chloride, triphenylsilyl chloride, tribenzylsilyl chloride, trimethylsilyl acetamide, N,O-bis(trimethylsilyl)acetamide and the like to give the compound of the formula (35-a) or (35-b) in which $R^{14}$ is an organic silyl group. The resultant compound is isolated or purified, if necessary, and subjected to the reaction with the compound of the formula (36) and then with the compound of the formula (37) or its reactive derivative at the carboxy group. According to the present method, the compound of the formula (34-a) or (34-b) can be prepared in a high yield with excellent stereoselectivity.

Moreover, the compound of the formula (34-a) or (34-b) in which $R^{14}$ is a hydroxy-protective group can be subjected to the deprotection, if necessary, whereby the compound of the formula (34-a) or (34-b) in which $R^{14}$ is a hydrogen atom is obtained. The deprotection to eliminate the hydroxy-protective group may be carried out in a conventional manner, depending upon the type of the protective group.

In the starting compound of the formula (35-a) or (35-b), the compound having a hydrogen atom for $R^{14}$ is a known compound, and the compound having a hydroxy-protective group for $R^{14}$ can be prepared from the compound having a hydrogen atom for $R^{14}$ in a conventional manner.

The azetidinone compounds of the formulas (34-a) and (34-b) prepared by the process of the invention are useful as synthetic intermediates for the synthesis of 2-oxaisocephem antimicrobial agent having a cis-configuration at the 6- and 7-positions thereof. For example, the compound of the following formula (13-c) which is a starting compound in the reaction scheme-10 can be prepared from the compound of the following formulas (34-c) and (34-d) according to the reaction scheme-13 as shown below.

Reaction scheme-13

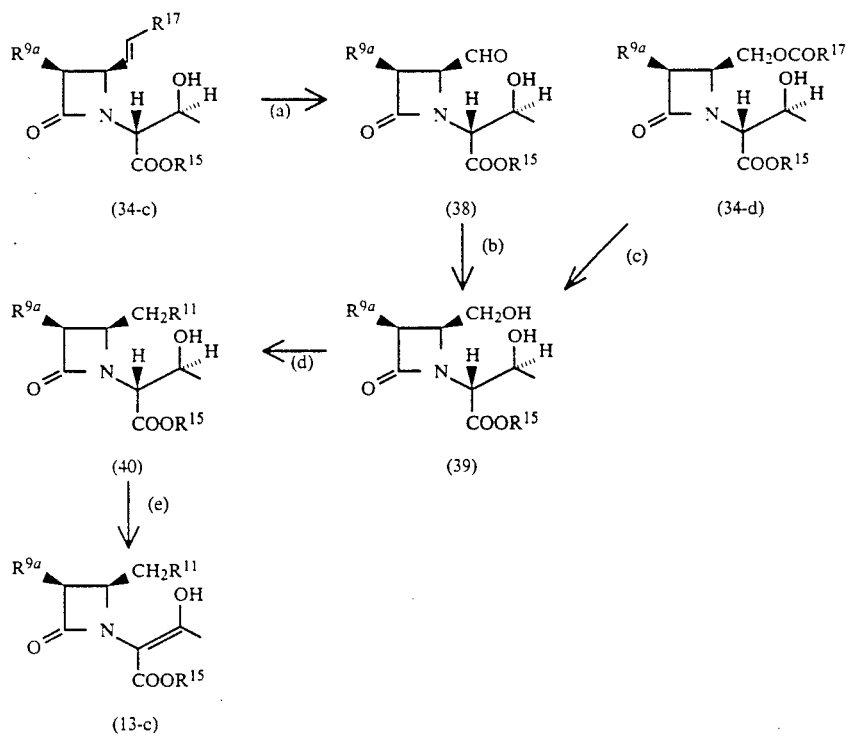

wherein $R^{9a}$, $R^{11}$, $R^{15}$ and $R^{17}$ have the same meanings as defined above.

In the above reaction scheme, the reaction (a) by which the compound of the formula (38) is produced from the compound of the formula (34-c) is carried out by oxidizing the compound of the formula (34-c) with ozone.

The reaction is conducted in substantially the same manner as the oxidation according to the aforesaid reaction scheme-11 step (h). Therefore, reaction procedures and reaction conditions (for example, solvent, the amount of ozone, reaction temperature, reaction time, etc.) for this reaction may be the same as those as exemplified in the reaction scheme-11 step (h).

The reaction (b) by which the compound of the formula (39) is produced from the compound of the formula (38) is a reaction that reduces the aldehyde group of the compound of the formula (38) to a hydroxy group. The reaction is conducted in substantially the same manner as the reduction according to the aforesaid reaction scheme-11 step (i). Therefore, reaction procedures and reaction conditions (for example, the reducing agent, solvent, reaction temperature, reaction time, etc.) for this reaction may be the same as those as exemplified in the reaction scheme-11 step (i).

The reaction (c) by which the compound of the formula (39) is produced from the compound of the formula (34-d) is carried out by subjecting the compound of the formula (34-d) to deesterification in the presence of a basic compound or an acid compound in a suitable inert solvent or without a solvent.

As examples of the inert solvent used in the above reaction, there may be mentioned halogenated hydrocarbons such as dichloromethane, dichloroethane, chloroform, carbon tetrachloride, etc., ethers such as demethyl ether, diethyl ether, tetrahydrofuran, dioxane, anisole, etc.; nitro compounds such as nitromethane, nitrobenzene, etc.; alcohols such as methanol, ethanol, etc.; acetic acid esters such as ethyl acetate, methyl acetate, etc.; aliphatic hydrocarbons such as hexane, heptane, octane, etc.; aromatic hydrocarbons such as benzene, toluene, xylene, etc.; amines such as pyridine, piperidine, etc.; aprotic polar solvents such as dimethylformamide (DMF), hexamethylphosphoric triamide (HMPA), dimethyl sulfoxide (DMSO), etc.; carbon disulfide, water; and mixtures of water and the above-mentioned organic solvents.

As examples of the acid compound, there may be mentioned Lewis acids such as anhydrous aluminum chloride, stannic chloride, titanium tetrachloride, boron trichloride, boron trifluoride-ethyl ether complex, zinc chloride, etc., inorganic acids such as hydrochloric acid, nitric acid, sulfuric acid, etc., organic acids such as trichloroacetic acid, trifluoroacetic acid, methanesulfonic acid, acetic acid, etc., and acid-form ion exchange resins. The basic compound mentioned above is exemplified by organic bases such as trialkylamines, e.g. triethylaine, tributylamine, etc., pyridine, picoline, 1,5-diazabicyclo[4,3,0]nonene-5, 1,4-diazabicyclo[2,2,2]octane, 1,8-diazabicyclo[5,4,0]undecene-7, etc., and inorganic bases such as alkali metal hydroxides, e.g. sodium hydroxide, potassium hydroxide, etc., alkali me&al carbonates, e.g. sodium carbonate, potassium carbonate, etc., and alkali metal hydrogen carbonates, e.g. sodium hydrogen carbonate, potassium hydrogen carbonate, and so on.

The suitable amount of the basic compound or the acid compound to be used is 1 to 100 mols, preferably 1 to 20 mols, of the basic compound or the acid compound per mol of the compound of the formula (34-d).

The reaction is carried out at $-20°$ C. to $80°$ C., preferably $-10°$ C. to $50°$ C., and completed in 30 minutes to 48 hours, preferably about 1 to about 24 hours.

The reaction (d) by which the compound of the formula (40) is produced from the compound of the formula (39) is a reaction that converts the hydroxymethyl group at the 4-position of the compound of the formula (39) to the group of the formula: $-CH_2-R^{11}$ (wherein $R^{11}$ is as defined above). The reaction is conducted in substantially the same manner as the reaction according to the aforesaid reaction scheme-11 step (j). Therefore, reaction procedures and reaction conditions (for example, the reagent, solvent, reaction temperature, reaction time, etc.) may be the same as those as exemplified in the reaction scheme-11 step (j).

The reaction (e) by which the compound of the formula (13-c) is produced from the compound of the formula (40) is carried out by subjecting the compound of the formula (40) to oxidation.

As examples of the oxidizing agent used in the above reaction, there may be mentioned any oxidizing agent used in the oxidation which converts a hydroxy group to an oxo group, for example, percarboxylic acids such as peracetic acid, perbenzoic acid, m-chloroperbenzoic acid, etc., chromic acids such as chromic acid, sodium dichromate, etc., manganese dioxide and the like. The reaction is usually carried out in a solvent. Any solvent which does not adversely influence the reaction can be used. Examples of the solvent include ketones such as acetone, methyl ethyl ketone, etc., alkanoic acids such as acetic acid, propionic acid, etc., halogenated hydrocarbons such as methylene chloride, 1,2-dichloroethane, chloroform, etc., water and a mixed solvent thereof.

The suitable amount of the oxidizing agent to be used is at least 1 equivalent, preferably 1 to 2 equivalents to the compound of the formula (40).

The reaction is usually carried out at $-70°$ C. to $60°$ C., preferably about $0°$ C. to room temperature, and completed generally in about 30 minutes to about 10 hours.

In the reaction scheme-13, when the compound of the formula (34-b) is used as a starting compound instead of the compound of the formula (34-c) or (34-d), the compound having (3R, 4R) configuration at the 3- and 4-positions of the azetidinone ring of the compound of the formula (13-c) can be obtained according to the reaction scheme-13 mentioned above.

Among the compounds of the formula (1) according to the present invention, compounds having basic groups can be easily converted to salts by permitting a pharmaceutically acceptable acid to act thereon, while compounds having acidic groups can be easily converted to salts by reacting them with a pharmaceutically acceptable basic compound. The acid is exemplified by inorganic acids such as hydrochloric acid, sulfuric acid, phosphoric acid, hydrobromic acid, etc., and organic acids such as oxalic acid, maleic acid, fumaric acid, malic acid, tartaric acid, citric acid, benzoic acid, acetic acid, p-toluenesulfonic acid, ethanesulfonic acid, etc. The basic compound is exemplified by metal hydroxides such as sodium hydroxide, potassium hydroxide, calcium hydroxide, etc., and alkali metal carbonates or alkali metal hydrogen carbonates such as sodium carbonate, sodium hydrogen carbonate, potassium hydrogen carbonate, etc.

The salts of the compound of the invention naturally include inner salts and quaternary ammonium salts as well.

The thus-produced compound of this invention can be isolated and purified without difficulty by conventional means of separation. Employable as the conventional means of separation are, for instance, solvent extraction, dilution, recrystallization, column chromatography and preparative thin layer chromatography.

The compound of the invention as represented by the formula (1) naturally includes optical isomers as well as syn and anti isomers. These isomers can be separated from each other by a conventional resolution method, for example, by using an optical resolution agent or an enzyme.

The compounds of this invention are useful as antimicrobial agents and used usually in the form of ordinary pharmaceutical preparations. Commonly used diluents or excipients such as fillers, extenders, binders, wetting agents, disintegrants, surfactants and lubricants are employed in the formulation of the preparation.

Various dosage forms of the therapeutic agents can be selected according to the purpose of the therapy. Typical dosage forms which can be used are tablets, pills, powders, liquid preparations, suspensions, emulsions, granules, capsules, suppositories, and injectable preparations (solutions, suspensions, etc.).

In molding a pharmaceutical composition into a tablet form, a wide range of carriers known in the art can be used. Examples of suitable carriers include excipients such as lactose, white sugar, sodium chloride, glucose, urea, starch, calcium carbonate, kaolin, crystalline cellulose and silicic acid, binders such as water, ethanol, propanol, simple syrup, glucose solution, starch solution, gelatin solution, carboxymethyl cellulose, shellac, methyl cellulose, potassium phosphate and polyvinyl pyrrolidone, disintegrants such as dired starch, sodium alginate, agar powder, laminaria powder, sodium hydrogen carbonate, calcium carbonate, polyoxyethylenesorbitan fatty acid esters, sodium laurylsulfate, stearic acid monoglyceride, starch, and lactose, disintegration inhibitors such as white sugar, stearic acid glyceryl ester, cacao butter and hydrogenated oils, absorption promotors such as quaternary ammonium bases and sodium laurylsulfate, humectants such as glycerol and starch, adsorbents such as starch, lactose, kaolin, bentonite and colloidal silicic acid, and lubricants such as purified talc, stearic acid salts, boric acid powder, polyethylene glycol.

The tablets, if desired, can be coated, and made into sugar-coated tablets, gelatin-coated tablets, enteric-coated tablets, film-coated tablets, or tablets comprising two or more layers.

In molding the pharmaceutical composition into pills, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, gelatin, and ethanol, and disintegrants such as laminaria and agar.

In molding the pharmaceutical composition into a suppository form, a wide variety of carriers known in the art can be used. Examples of suitable carriers include polyethylene glycol, cacao butter, higher alcohols, esters of higher alcohols, gelatin, and semisynthetic glycerides.

When the pharmaceutical composition is formulated into an injectable preparation, the resulting solution, emulsion and suspension are sterilized, and are isotonic with respect to the blood. In formulating the pharmaceutical composition into the form of a solution, emulsion or suspension, all diluents customarily used in the art can be used. Examples of suitable diluents are water, ethyl alcohol, propylene glycol, ethoxylated isostearyl alcohol, polyoxyethylene sorbitol, and polyoxyethylenesorbitan fatty acid esters. Sodium chloride, glucose or glycerol may be incorporated into a pharmaceutical composition, in an amount sufficient to prepare isotonic solutions. The pharmaceutical composition may further contain ordinary dissolving aids, buffers, painalleviating agents, and optionally coloring agents, preservatives, perfumes, flavors, sweeteners and other drugs.

In molding a pharmaceutical composition into an ointment form, a cream form and a gel form, a wide range of diluents known in the arts can be used. Examples of suitable diluents include white petrolatum, paraffin, glycerin, cellulose derivatives, polyethylene glycol, silicones, and bentonite.

The amount of the compound of the formula (1) and the pharmaceutically acceptable salts thereof of this invention as attractive ingredient to be incorporated into a pharmaceutical composition is not particularly limited, and can vary over a wide range. A suitable therapeutically effective amount of the compound of the formula (1) and the pharmaceutically acceptable salts thereof of this invention is usually about 1 to about 70% by weight, preferably 1 to 30% by weight, based on the entire composition.

The administration method of the pharmaceutical composition according to the invention is not particularly limited and can be adequately selected according to the form of the preparation, age and sex of the patient, and symptom of disease. For example, the tablets, pills, liquid preparations, suspensions, emulsions, granules, and capsules are orally administered. The injectable preparations are intravenously administered either alone or together with ordinary auxiliary agents such as glucose and amino acids. Furthermore, as required, the injectable preparations can be singly administered intramuscularly, intracutaneously, subcutaneously, or intraperitoneally. The suppository is administered intrarectally.

The dosage of the pharmaceutical composition is suitably selected according to the purpose of use, age and sex of the patient, and the symptoms of disease, etc. Usually, a preferred dosage of the compound of this invention is about 1 to 100 mg/kg, preferably 5 to 20 mg/kg weight per day, and the pharmaceutical composition may be administered 2 to 4 times per day.

Hereinafter, this invention will be described in greater detail with reference to Reference Examples, Examples and Pharmaceutical Examples.

EXAMPLES

Reference Example 1

(3S,4S)-N-(α-Benzyloxycarbonyl-β-trifluoromethanesulfonyloxy-α, β-propenyl)-3-azido-4-methanesulfonyloxymethyl-2-azetidinone (3S,4S)-N-(α-Benzyloxycarbonyl-β-hydroxy-α, β-propenyl)-3-azido-4-methanesulfonyloxymethyl-2-azetidinone (26.3 g, 64 mmol) was dissolved in dry methyele chloride (300 ml). The solution was cooled to −30° C. in a dry ice-acetone bath, followed by addition of trifluoromethanesulfonic anhydride (21.7 g, 77 mmol). A solution of triethylamine (12.5 ml, 90 mmol) in dry methylene chloride (110 ml) was added dropwise to the above-obtained solution over 40 minutes. After completion of the dropwise addition, the mixture was stirred at the same temperature for 20 minutes, and after addition of a 10-fold dilution of conc. hydrochloric acid, the mixture was washed twice with water and the organic layer was dried over anhydrous magnesium sulfate. The solvent was then distilled off under reduced pressure to give the title compound (31.3 g) as dark red oil.

$[\alpha]_D^{20}$ −52.9° (C=3.48, in chloroform)

NMR (CDCl$_3$) δ: 2.27 (3H, s), 2.86 (3H, s), 4.18–4.64 (3H, m), 4.95 (1H, d, J=5 Hz), 5.27 (2H, s), 7.38 (5H, s)

Reference Example 2

Benzyl (6S,7S)-7-azido-3-hydroxymethyl-Δ$^3$-O-2-isocephem-4-carboxylate

A) (3S,4S)-N-(α-benzyloxycarbonyl-β-trifluoromethanesulfonyloxy-α,β-propenyl)-3-azido-4-methanesulfonyloxymethyl-2-azetidinone (30.3 g, 56 mmol) was dissolved in methylene chloride (300 ml) and the solution was cooled to 0° C. To the solution was added dropwise a solution of triethylamine (9.37 ml, 67 mmol) in methylene chloride (94 ml). After completion of the dropwise addition, the mixture was stirred at room temperature for 40 minutes. Thereafter, a 0.1M methylene chloride solution of iodine (672 ml, 67 mmol) was added dropwise over 1.5 hours. After 1 hour of stirring, the reaction mixture was washed twice with water and dried over anhydrous magnesium sulfate, followed by removal of the solvent, whereby there was obtained crude (3S,4S)-N-(α-benzyloxycarbonyl-β,γ-diiodo-α, β-propenyl)-3-azido-4-methanesulfonyloxymethyl-2-azetidinone (42.0 g).

The thus-obtained crude product was directly subjected to the next reaction procedure without purification.

B) The crude iodide compound (42.0 g) obtained by the above procedure was dissolved in dimethylformamide (600 ml), followed by addition of water (0.6 ml). Thereafter, potassium formate (18.8 g. 224 mmol) was added under ice-cooling. The mixture was stirred at room temperature for 12 hours, poured into ice-water (1 l) and extracted five times with methylene chloride. The extract was washed four times with water and dried over anhydrous magnesium sulfate. The solvent was then removed to give crude benzyl (6S,7S)-7-azido-3-formyloxymethyl-Δ$^3$-O-2-isocephem-4-carboxylate (24.7 g) as brown oil.

C) The crude formate compound (24.7 g) obtained by the above procedure was dissolved in a mixture of acetone (200 ml) and water (100 ml) and, after addition of 12M hydrochloric acid (12 ml), the mixture was warmed to 28° C. and stirred at the same temperature for 6 hours. The reaction mixture was poured into water and extracted five times with methylene chloride and the extract was washed three times with water and dried over anhydrous magnesium sulfate. The solvent was then removed under reduced pressure to give crude benzyl (6S,7S)-7-azido-3-hydroxymethyl-Δ$^3$-O-2-isochem-4-carboxylate, which was purified by silica gel column chromatography [eluent: methylene chloride-methyl acetate (15:1)] to obtain the title compound (31.5 g) as orange oil.

$[\alpha]_D^{22}$ = −29° (C=0.62, in chloroform)

NMR (CDCl$_3$) δ: 3.60–3.90 (1H, m), 3.94 (1H, d, J=10 Hz), 4.27 (1H, d, J=14 Hz), 4.51 (1H, d, J=14 Hz), 4.61 (1H, dd, J=10 Hz, 3 Hz), 5.20 (1H, d, J=5 Hz), 5.29 (2H, s), 7.00–7.73 (5H, m)

Reference Example 3

Benzyl
(6S,7S)-7-azido-3-methanesulfonyloxymethyl-$\Delta^3$-O-2-isocephem-4-carboxylate Benzyl (6S,7S)-7-azido-3-hydroxymethy-$\Delta^3$-O-2-isocephem-4-carboxylate (3.15 g, 9.54 mmol) was dissolved in methylene chloride (100 ml) and the solution was cooled in an ice-methanol bath. To the solution was added triethylamine (2.13 ml, 15.6 mmol), followed by dropwise addition of methanesulfonyl chloride (0.96 ml, 12.40 mmol). After 40 minutes of stirring, the reaction mixture was washed twice with water and once with saturated aqueous sodium chloride. After drying over anhydrous sodium sulfate, the solvent was removed to give the title compound (4.82 g).

Reference Example 4

Benzhydryl
(6S,7S)-7-azido-3-(pyridin-4-ylthiomethyl-$\Delta^3$-O-2-isocephem-4-carboxylate Benzyl (6S,7S)-7-azido-3-acetoxymethyl-$\Delta^3$-O-2-isocephem-4-carboxylate (15 g, 40.32 mmol) was dissolved in methylene chloride (150 ml). The solution was cooled in an ice bath and trimethyliodosilane (12.62 ml, 88.71 mmol) was added dropwise thereto. After stirring for 1 hour at room temperature, the reaction mixture was cooled in a freezing mixture of ice and sodium chloride, and a solution of 4-mercaptopyridine (9.85 g, 88.71 mmol) and triethylamine (18.50 ml) in methylene chloride (150 ml) was added dropwise thereto at the same temperature. After stirring for 2 hours, the reaction mixture was concentrated. To the residue was added methanol (80 ml), and the mixture was stirred and concentrated. The resultant residue was washed with n-hexane (80 ml) and diethyl ether (80 ml) in turn to pulverize. The powder obtained above was dissolved in a mixture of methanol and tetrahydrofuran (1:1, 100 ml). To the solution was added diphenyldiazomethane (15.65 g, 80.65 mmol) and the mixture was stirred at room temperature overnight. The reaction mixture was concentrated to one-half of its original valume and cooled in a ice bath. The resultant precipitate was collected by filtration, washed with methanol and dried to give the title compound (10.55 g) as light yellow sharp-pointed needles.

mp: 197°–198° C.

Reference Example 5

Benzhydryl
(6S,7S)-7-[2-(2-t-butoxycarbonylaminothiazol-4-yl)-2-methoxyiminoacetamido]-3-(pyridin-4-ylthiomethyl)-$\Delta^3$-O-2-isocephem-4-carboxylate (syn-isomer)

Benzhydryl (6S,7S)-7-azido-3-(pyridin-4-ylthiomethyl)-$\Delta^3$-O-2-isocephem-4-carboxylate (13.60 g) was dissolved in methylene chloride (150 ml). Under ice-cooling, triethylamine (5.67 ml) was added to the solution and hydrogen sulfide gas was introduced into the mixture for 10 minutes at the same temperature. The mixture was stirred at room temperature for 40 minutes. The reaction mixture was washed with a saturated aqueous solution of sodium hydrogen carbonate and a saturated aqueous solution of sodium chloride in turn, dried over anhydrous magnesium sulfate and filtered to give a solution (referred to as solution A).

On the other hand, to a suspension of 2-(2-t-butoxycarbonylaminothiazol-4-yl)-2-methoxyiminoacetic acid (syn-isomer) (9 g) in methylene chloride (150 ml) was added dicyclohexylcarbodiimide (DCC) (6.16 g) under ice-cooling and the mixture was stirred at the same temperature for 10 minutes. To this mixture was added the above-mentioned solution A, and the mixture was stirred for 1 hour under ice-cooling and at room temperature for 15 hours. After completion of the reaction, the reaction mixture was filtered and the filtrate was concentrated. The residue was subjected to silica gel column chromatography [eluent: chloroform-n-hexane (9:1)] for separation and purification to give the title compound (15.02 g) as pale yellow plate crystals.

mp: 140°–142° C.

Reference Example 6

3,4-cis-3-Phthalimido-1-(2,2-ethyleneketal-1-ethoxycarbonylpropyl)-4-styrylazetidin-2-one In methylene chloride (200 ml) was dissolved ethyl 1-(3-phenylallylidene)amino-2,2-ethyleneketalbutyrate (30.3 g, 0.1 mol), and after addition of triethylamine (21 ml, 0.15 mol), the solution was cooled to −30° C. Then, a solution of 2-phthalimidoacetyl chloride (24.6 g, 0.11 mol) in methylene chloride (200 ml) was added dropwise and the mixture was stirred for 1 hour. After completion of the reaction, the reaction mixture was washed with a 10-fold dilution of concentrated hydrochloric acid (200 ml). The organic layer was washed twice with water (200 ml), dried over anhydrous magnesium sulfate, and filtered. The filtrate was concentrated and the residue was separated and purified by silica gel column chromatography [eluent: methylene chloride-ethyl acetate(10:1)] to give the title compound (36.8 g).

mp: 143°–144° C.

| Elemental analysis | C | H | N |
|---|---|---|---|
| Calcd. | 66.11 | 5.34 | 5.71 |
| Found | 65.92 | 5.51 | 5.74 |

Reference Example 7

3,4-cis-3-Phenylacetamido-1-(2,2-ethyleneketal-1-ethoxycarbonylpropyl)-4-styrylazetidin-2-one In ethanol (300 ml) was suspended 3,4-cis-3-phthalimido-1-(2,2-ethyleneketal-1-ethoxycarbonylpropyl)-4-styrylazetidin-2-one (49 g, 0.1 mol), followed by addition of 1M hydrazine hydrate in ethanol (100 ml). The mixture was refluxed for 2 hours, at the end of which time the precipitate was filtered off and the filtrate was concentrated under reduced pressure. To the residue was added methylene chloride (300 ml) and the resulting crystals were filtered off. To the filtrate was added triethylamine (16.7 ml, 0.12 mol), and under cooling at 0° C., phenylacetyl chloride (15.4 g. 0.1 mol) was added dropwise. After completion of the dropwise addition, the reaction was continued at the same temperature for 2 hours. The reaction mixture was washed by addition of a 10-fold dilution of concentrated hydrochloric acid (200 ml). The organic layer was washed with a saturated aqueous solution of sodium chloride and dried over anhydrous magnesium sulfate. It was then filtered and the filtrate was concentrated and recrystallized from benzene to give the title compound (40.5 g).

mp: 111°–112° C.

| Elemental analysis | C | H | N |
|---|---|---|---|
| Calcd. | 67.77 | 6.32 | 5.85 |
| Found | 67.92 | 6.18 | 5.79 |

Reference Example 8

3,4-cis-3-Phenylacetamido-1-(2-2-ethyleneketal-1-carboxypropyl)-4-styrylazetidin-2-one In tetrahydrofuran (150 ml) was dissolved 3,4-cis-3-phenylacetamido-1-(2,2-ethyleneketal-1-ethoxycarbonylpropyl)-4-styrylazetidin-2-one (47.9 g, 0.1 mol), followed by addition of water (100 ml). Then, 1N aqueous sodium hydroxide (110 ml) was added dropwise at room temperature and the reaction was conducted at the same temperature for 3 hours. After completion of the reaction, the reaction mixture was adjusted to pH 2 with concentrated hydrochloric acid and extracted twice with ethyl acetate (250 ml). The extract was washed with a saturated aqueous solution of sodium chloride, dried over anhydrous sodium sulfate, and filtered. The filtrate was concentrated and the residue was recrystallized from ethyl acetate to give the title compound (38.5 g)
mp: 165°-167° C.

| Elemental analysis | C | H | N |
|---|---|---|---|
| Calcd. | 66.66 | 5.82 | 6.22 |
| Found | 66.48 | 5.92 | 6.35 |

Reference Example 9

(3S,4R)-3-Amino-1-(2,2-ethyleneketal-1-carboxypropyl)-4-styrylazetidin-2-one and (3R,4S)-3-phenylacetamido-1-(2,2-ethyleneketal-1-carboxypropyl)-4-styrylazetidin-2-one In water (740 ml) was suspended 3,4-cis-3-phenylacetamido-1-(2,2-ethyleneketal-1-carboxypropyl)-4-styrylazetidin-2-one (66.4 g, 0.147 mol), followed by addition of 1N aqueous sodium hydroxide (147 ml). After the mixture was adjusted to pH 8 or less, penicillin G amidase (13.3 g) was added. The mixture was stirred at room temperature for 4 hours while it was adjusted to pH 8 with a saturated aqueous solution of sodium hydrogen carbonate. After completion of the reaction, the penicillin G amidase was filtered off and the filtrate was adjusted to pH 2. The filtrate was then washed twice with a mixed solvent of ethyl acetate and tetrahydrofuran (1:1) and the organic layer was extracted three times with 0.1N hydrochloric acid. The water layers were pooled, adjusted to pH 7 and concentrated to about 300 ml. Then, the solution was adjusted to pH 3 with a 10-fold dilution of concentrated hydrochloric acid. The resulting white crystals were recovered by filtration, washed 3 times with ice-water, and dried to give (3S,4R)-3-amino-1-(2,2-ethyleneketal-1-carboxypropyl)-4-styrylazetidin-2-one (8.9 g) as white crystals.
mp: 129°-131° C.
$[\alpha]_D^{23} = -102.8°$ (C=0.924, in ethanol)

| Elemental analysis | C | H | N |
|---|---|---|---|
| Calcd. | 61.44 | 6.07 | 8.42 |
| Found | 61.59 | 5.92 | 8.56 |

Further, the remaining ethyl acetate-tetrahydrofuran washings were evaporated in vacuo and the residue was separated and purified by silica gel column chromatography to give (3R,4S)-3-phenylacetamido-1-(2,2-ethyleneketal-1-carboxypropyl)-4-styrylazetidin-2-one as white sharp-pointed needles.
mp: 166°-167° C.
$[\alpha]_D^{23} = -2.9°$ (C=1.05 in chloroform-dimethylformamide)

Reference Example 10

(3S,4R)-3-Phthalimido-1-(2,2-ethyleneketal-1-benzyloxycarbonylpropyl)-4-styrylazetidin-2-one In a mixture of water (100 ml) and acetone (100 ml) was dissolved (3S,4R)-3-amino-1-(2,2-ethyleneketal-1-carboxypropyl)-4-styrylazetidin-2-one (16.6 g, 0.05 mol). After addition of 1N aqueous modium hydroxide (55 ml), the solution was cooled to −20° C. To this was added dropwise a solution of o-methoxycarbonylbenzoyl chloride (11 g, 0.055 mol) in acetone (30 ml). After completion of the dropwise addition, the mixture was stirred at the same temperature for 1 hour, at the end of which time it was adjusted to pH 1 with a 10-fold dilution of concentrated hydrochloric acid. The mixture was extracted with ethyl acetate (200 ml) and the extract was washed with a saturated aqueous solution of sodium chloride, dried over anhydrous magnesium sulfate, and filtered. The filtrate was concentrated under reduced pressure. To the residue were added dimethylformamide (50 ml) and cesium carbonate (19 g, 0.06 mol), followed by addition of benzyl bromide (10.3 g, 0.06 mol). The reaction was conducted at room temperature for 3 hours. Thereafter, water (300 ml) was added thereto and the mixture was extracted twice with ethyl acetate (200 ml). The extract was washed with a saturated aqueous solution of sodium chloride, dried over anhydrous sodium sulfate, and filtered. The filtrate was concentrated and the residue was separated and purified by silica gel column chromatography [eluent:n-hexane-ethyl acetate(3:2)] to give the title compound (17.7 g) as white powder.
mp: 57°-61° C.
$[\alpha]_D^{23} = -50.0°$ (C=1.02, in chloroform)

| Elemental analysis | C | H | N |
|---|---|---|---|
| Calcd. | 69.56 | 5.11 | 5.07 |
| Found | 69.77 | 5.39 | 5.21 |

Reference Example 11

(3S,4S)-3-Phthalimido-1-(2,2-ethyleneketal-1-benzyloxycarbonylpropyl)-4-formylazetidin-2-one In methylene chloride (150 ml) was dissolved (3S,4R)-3-phthalimido-1-(2,2-ethyleneketal-1-benzyloxycarbonylpropyl)-4-styrylazetidin-2-one (26.56 g, 48.1 mmol). After cooling to −50° C., ozone was bubbled into the solution. When the reaction mixture turned light blue, the introduction of ozone was discontinued and nitrogen gas was introduced instead until nitrogen purging was completed. Then, after addition of dimethyl sulfide (7.3 ml), the temperature was gradually returned to room temperature over 2.5 hours. Thereafter, the reaction mixture was washed with a 5% aqueous solution of sodium hydrogen carbonate (150 ml) and washed twice with water (150 ml). The solution was dried over anhydrous sodium sulfate and filtered and the filtrate was concentrated. The residue was washed twice with n-hexane and re-washed with a mixture of diethyl ether (50 ml) and n-hexane (50 ml). The residue was sufficiently dried under reduced pressure to give the title compound (23.28 g) as white powder.

$[\alpha]_D^{23}$ −60.2° (C=1.245, in chloroform)

| Elemental analysis | C | H | N |
|---|---|---|---|
| Calcd. | 55.91 | 4.69 | 5.02 |
| Found | 55.72 | 4.73 | 5.29 |

Reference Example 12

(3S,4S)-1-(1-Benzyloxycarbonyl-2,2-ethyleneketalpropyl)-3-phthalimido-4-hydroxymethylazetidin-2-one In a mixture of tetrahydrofuran (40 ml) and water (10 ml) was dissolved (3S,4S)-1-(1-benzyloxycarbonyl-2,2-ethyleneketalpropyl)-3-phthalimido-4-formuylazetidin-2-one (8.65 g, 18 mmol) and while the solution was stirred at room temperature, sodium cyanoborohydride was added. The reaction was conducted for 3 hours, with the mixture being adjusted to the range of pH 3 to pH 4 with a 10-fold dilution of concentrated hydrochloric acid. After addition of a saturated aqueous solution of sodium chloride (40 ml), the reaction mixture was extracted twice with ethyl acetate (40 ml). The ethyl acetate layers were pooled and washed twice with a saturated aqueous solution of sodium chloride (80 ml). The solution was dried by addition of anhydrous sodium sulfate and filtered, and the filtrate was concentrated under reduced pressure to give the title compound (7.80 g) as light yellow powder.

mp: 37°-44° C.

$[\alpha]_D^{23}$ = +10.3° (C=1.07, in chloroform)

| Elemental analysis | C | H | N |
|---|---|---|---|
| Calcd. | 62.50 | 5.03 | 5.83 |
| Found | 62.38 | 5.24 | 6.02 |

Reference Example 13

(3S,4S)-1-(1-Benzyloxycarbonyl-2,2-ethylene-ketalpropyl)-3-phthalimido-4-mesyloxymethylazetidin-2-one In methylene chloride (90 ml) was dissolved (3S,4S)-1-(1-benzyloxycarbonyl-2,2-ethyleneketalpropyl)-3-phthalimido-4-hydroxymethylazetidin-2-one (8.65 g, 18 mmol) and after the solution was cooled to 3° C., triethylamine (3.0 ml) and mesyl chloride (1.5 ml) were added. The mixture was stirred for 1 hour. The reaction mixture was washed with a 20-fold dilution of concentrated hydrochloric acid (90 ml) and, then, washed 3 times with water (90 ml). The solution was dried over anhydrous sodium sulfate and filtered, and the filtrate was concentrated under reduced pressure to give the title compound (9.80 g) as pale yellow powder.

mp: 43°-47° C.

$[\alpha]_D^{23}$ = −18.6° (C=1.02, in chloroform)

| Elemental analysis | C | H | N |
|---|---|---|---|
| Calcd. | 62.76 | 4.63 | 5.85 |
| Found | 63.03 | 4.75 | 6.09 |

Reference Example 14

(3S,4S)-1-(1-Benzyloxycarbonyl-2-hydroxy-1-propenyl)-3-phthalimido-4-mesyloxymethylazetidin-2-one (3S,S)-1-(1-Benzyloxycarbonyl-2,2-ethyleneketalpropyl)-3-phthalimido-4-mesyloxymethylazetidin-2-one (8.94 g, 16 mmol) was dissolved by addition of 5% trifluoroacetic acid (32 ml). After stirring for 30 minutes, the solution was concentrated under reduced pressure. To the residue was added water (100 ml) and the mixture was extracted twice with methylene chloride (50 ml). The methylene chloride layers were pooled, washed 4 times with water (100 ml), dried over anhydrous sodium sulfate, and filtered. The filtrate was concentrated under reduced pressure and the residue was separated and purified by silica gel column chromatography [eluent: methylene chloride-ethyl acetate(20:1)] to give the title compound (6.41 g) as white powder.

mp: 61°-65° C.

$[\alpha]_D^{23}$ = −34.10° (C=0.85, in chloroform)

| Elemental analysis | C | H | N |
|---|---|---|---|
| Calcd. | 56.03 | 4.31 | 5.44 |
| Found | 56.12 | 4.37 | 5.17 |

Reference Example 15

(3S,4S)-1-(1-Benzyloxycarbonyl-2-trifluoromethanesulfonyloxy-1-propenyl)-3-phthalimido-4-mesyloxymethylazetidin-2-one In methylene chloride (40 ml) was dissolved (3S,4S)-1-(1-benzyloxycarbonyl-2-hydroxyl-1-propenyl)-3-phthalimido-4-mesyloxymethylazetidin-2-one (5.15 g, 10 mmol). The solution was cooled to −30° C. and, then, trifluoromethanesulfonic anhydride was added. Thereafter, a solution of triethylamine (1.9 ml) in methylene chloride (20 ml) was added dropwise thereto over 10 minutes. After completion of the dropwise addition, the mixture was stirred for 50 minutes. Then, it was made weakly acidic with a 10-fold dilution of concentrated hydrochloric acid and the temperature was returned to room temperature. The reaction mixture was washed 3 times with water (100 ml), dried by addition of anhydrous sodium sulfate, and filtered. The filtrate was concentrated in vacuo to give the title compound (6.21 g) as white powder.

mp: 51°-55° C.

$[\alpha]_D^{23}$ +40.8° (C=1.03, in chloroform)

| Elemental analysis | C | H | N |
|---|---|---|---|
| Calcd. | 46.44 | 3.27 | 4.33 |
| Found | 46.70 | 3.09 | 4.61 |

Reference Example 16

Benzyl (6S,7S)-7-phthalimido-3-acetoxymethyl-$\Delta^3$-O-2-isocephem-4-carboxylate In methylene chloride (15 ml) was dissolved (3S,4S)-1-(1-benzyloxycarbonyl-2-trifluoromethanesulfonyloxy-1-propenyl)-3-phthalimido-4-mesyloxymethylazetidin-2-one (1.94 g, 3 mmol). Then, triethylamine (0.42 ml) was added under ice-cooling and the mixture was stirred at room temperature for 35 minutes. To this was added dropwise a solution of bromine (0.15 ml) in methylene chloride (15 ml) over a period of 5 minutes, after which the mixture was stirred for 15 minutes. The reaction mixture was washed 3 times with water (30 ml), dried by addition of anhydrous sodium sulfate, and filtered. The filtrate was concentrated under reduced pressure. The residue was dissolved by addition of dimethylformamide (15 ml), followed by addition of potassium acetate (1.18 g) and water (0.15 ml). The mixture was stirred for 5 hours. Thereafter, water (150 ml) was added and the mixture was extracted 3 times with ethyl acetate (50 ml). The ethyl acetate layers were pooled, washed 3 times with water (100 l) and washed once with a saturated aqueous solution of sodium chloride (100 ml). The solution was dried by addition of anhydrous sodium sulfate and filtered, and the filtrate was concentrated under reduced pressure. Finally, the residue was separated and purified by silica gel column chromatography [eluent: n-hexaneethyl acetate (7:4)] to give the title compound (0.92 g) as pale yellow powder.

mp: 80°-83° C.

$[\alpha]_D^{23} = +11.4°$ (C=2.016, in chloroform)

| Elemental analysis | C | H | N |
|---|---|---|---|
| Calcd. | 63.02 | 4.23 | 5.88 |
| Found | 63.21 | 4.34 | 5.71 |

Reference Example 17

2-(4-Nitrophthalimido)acetic acid

To a mixture of concentrated sulfuric acid (350 ml) and fuming nitric acid (d=1.52)(60 ml) was added 2-phthalimidoacetic acid (70 g) with stirring and under ice-cooling. The mixture was stirred for 1 hour under ice-cooling and for 2 hours at room temperature, and poured into ice-water (2 l). The resultant precipitate was collected by filtration and recrystallized from a mixture of water (2 l) and ethanol (1 l) to give the title compound (60 g) as light yellow sharp-pointed needles.

mp: 196°-197° C.

NMR (DMSO-d6) δ: 4.42 (2H, s), 8.23 (1H, d, J=8 Hz), 8.52-8.8 (2H, m)

Reference Example 18

2-(4-Nitrophthalimido)acetyl chloride

To a suspension of 2-(4-nitrophthalimido)acetic acid (58.6 g) in toluene (250 ml) was added phosphorus pentachloride (48.8 g) and the mixture was refluxed for 3 hours. After completion of the reaction, the solvent was removed under reduced pressure. By addition of hexane to the residue, the title compound (62.3 g) was obtained as light yellow sharp-pointed needles.

mp: 129°-130° C.

NMR (CDCl₃) δ: 4.92 (2H, s), 8.18 (1H, dd, J=8 Hz, 1 Hz), 8.6-8.8 (2H, m)

Reference Example 19

1-[1-R-(4-Nitrobenzyl)oxycarbonyl-2-S-hydroxypropyl]-3-S-(4-nitrophthalimido)-4-R-styrylazetidin-2-one To a suspension of D-threonine (1.2 g, 10 mmol) in methylene chloride (20 ml) was added N,O-bis(trimethylsilyl)acetamide (4.94 ml, 20 mmol), and the mixture was refluxed for 15 hours to make a homogeneous solution. Subsequently, cinnamaldehyde (1.51 ml, 10 mmol) was added to the solution and the mixture was refluxed for hours to give a solution (referred to as solution A).

On the other hand, 2-(4-nitrophthalimido)acetyl chloride (2.24 g, 10 mmol) was dissolved in methylene chloride (50 ml) and cooled below −50° C. To the solution was added triethylamine (1.54 ml, 11 mmol) and the mixture was stirred at the same temperature for 10 minutes to give a solution (referred to as solution B).

Subsequently, to the above-mentioned solution B was added the solution A at −40° C. to −50° C., and the reaction was conducted for 30 minutes at the same temperature and the temperature was gradually returned to room temperature. After completion of the reaction, to the reaction mixture were added methanol (5 ml) and concentrated hydrochloric acid (1 ml) and the mixture was washed 3 times with water (100 ml). The organic layer was dried over anhydrous sodium sulfate and filtered. The filtrate was concentrated under reduced pressure to give the title compound (4.17 g) as amorphous solid.

The amorphous substance obtained above was dissolved in dimethylformamide (10 ml). To the solution were added potassium carbonate (1.66 g, 12 mmol), potassium iodide (1.66 g, 10 mmol) and 4-nitrobenzyl bromide (2.16 g, 10 mmol) at room temperature and the mixture was stirred for 1 hour. Thereafter, a mixed solution (100 ml) of ethyl acetate and tetrahydrofuran (1:1) was added to the reaction mixture and the mixture was washed with water (100 ml) and a saturated aqueous solution of sodium chloride (100 ml) in turn. The organic layer was dried over anhydrous sodium sulfate, filtered and concentrated under reduced pressure. The residue was dissolved in ethyl acetate, and diethyl ether was added thereto. The resultant precipitate was collected by filtration to give the title compound (3.18 g) as white sharp-pointed needles.

mp: 213°-214° C.

NMR (CDCl₃) δ: 1.40 (3H, d, J=6.2 Hz) 4.35 (1H, d, J=4.6 Hz), 4.36-4.63 (1H, m), 4.93 (1H, dd, J=5.5 Hz, 9.0 Hz), 5.34 (2H, s), 5.68 (1H, d, J=5.5 Hz), 6.25 (1H, dd, J=9.0 Hz, 15.8 Hz), 6.66 (1H, d, J=15.8 Hz), 7.21 (5H, s), 7.53 (2H, d, J=9.0 Hz), 8.05 (1H, dd, J=1.1 Hz, 7.6 Hz), 8.16 (2H, d, J=9 Hz), 8.60 (1H, dd, J=2.0 Hz, 7.6 Hz), 8.65 (1H, s).

Further, the remaining filtrate was concentrated and the residue was subjected to silica gel column chromatography [eluent:ethyl acetate-n-hexane (2:1)] for separation and purification to give 1-[1-R-(4-nitrobenzyl)oxycarbonyl-2-S-hydroxypropyl]-3-R-(4-nitrophthalimido)-4-S-styrylazetidin-2-one (300 mg) as pale yellow amorphous solid.

mp: 66°-74° C.

In a manner analogous to Reference Example 19, the compounds of Reference Examples 20 to 24 were obtained using appropriate starting compounds.

Reference Example 20

1-(1-R-Benzyloxycarbonyl-2-S-hydroxypropyl)-3-S-phthalimido-4-R-styrylazetidin-2-one White amorphous solid
mp: 52°–57° C.

Reference Example 21

1(1-R-Benzyhydryloxycarbonyl-2-S-hydroxypropyl)-3-S-phthalimido-4-R-styrylazetidin-2-one White sharp-pointed needles
mp: 109°–115° C.

Reference Example 22

1-(1-R-Benzhydryloxycarbonyl-2-S-hydroxypropyl)-3-S-(4-nitrophthalimido)-4-R-styrylazetidin-2-one White sharp-pointed needles
mp: 222°–223° C.

Reference Example 23

1-(1-R-Benzyloxycarbonyl-2-S-hydroxypropyl)-3-S-(4-nitrophthalimido)-4-R-styrylazetidin-2-one Pale yellow amorphous solid
mp: 78°–80° C.

Reference Example 24

1-[1-R-(4-Methoxybenzyl)oxycarbonyl-2-S-hydroxypropyl]-3-S-(4-nitrophthalimido)-4-R-styrylazetidin-2-one Light yellow sharp-pointed needles
mp: 122°–123° C.

Reference Example 25

1-[1-S-(4-Nitrobenzyl)oxycarbonyl-2-R-hydroxypropyl]-3-R-(4-nitrophthalimido)-4-S-styrylazetidin-2-one.

The title compound (3.21 g) was obtained in the substantially same manner and amount of reagents used as those of Reference Example 19 using L-threonine instead of D-threonine.

Pale yellow amorphous solid
mp: 66°–74° C.

Further, 1-[1-S-(4-nitrobenzyl)oxycarbonyl-2-R-hydroxypropyl]-3-S-(4-nitrophthalimido)-4-R-styrylazetidin-2-one (290 mg) was obtained from the mother liquor.

In a manner analogous to Reference Example 25, the compounds of Reference Examples 26 to 30 were obtained using appropriate starting compounds.

Reference Example 26

1-(1-S-Benzhydryloxycarbonyl-2-R-hydroxypropyl)-3-R-phthalimido-4-S-styrylazetidin-2-one White amorphous solids
mp: 62°–76° C.

Reference Example 27

1-(1-S-Benzyloxycarbonyl-2-R-hydroxypropyl)-3-R-(4-nitrophthalimido)-4-S-styrylazetidin-2-one Pale yellowish orange amorphous solid
mp: 77°–83° C.

Reference Example 28

1-(1-S-Benzhydryloxycarbonyl-2-R-hydroxypropyl)-3-R-(4-nitrophthalimido)-4-S-styrylazetidin-2-one Pale yellowish brown amorphous solid
mp: 59°–68° C.

Reference Example 29

1-(1-S-Benzyloxycarbonyl-2-R-hydroxypropyl)-3-R-phthalimido-4-S-styrylazetidin-2-one Light yellow sharp-pointed needles
mp: 103°–108° C.

Reference Example 30

1-[1-S-(4-Methoxybenzyl)oxycarbonyl-2-R-hydroxypropyl]-3-R-(4-nitrophthalimido)-4-S-styrylazetidin-2-one Pale yellow amorphous solid
mp: 86°–97° C.

Reference Example 31

1-[1-R-Benzyloxycarbonyl-2-S-(t-butyldimethylsilyl)oxypropyl]-3-S-phthalimido-4-S-(4-chlorobenzoyl)oxymethylazetidin-2-one A mixture of 4-chlorobenzoyloxyacetaldehyde (0.6 g, 3 mmol) and 0-t-butyldimethylsilyl-D-threonine benzyl ester (0.94 g, 3 mmol) in methylene chloride (10 ml) was stirred for 30 minutes and anhydrous magnesium sulfate (3.6 g, 30 mmol) was added thereto. The mixture was stirred for 2 hours at room temperature and cooled to −40° C., and triethylamine (0.83 ml, 6 mmol) was added thereto. To the mixture was added dropwise a solution of 2-phthalimidoacetyl chloride (1.26 g, 6 mmol) in methylene chloride (10 ml) while holding the temperature at −30° C. to −25° C. After completion of the dropwise addition, the mixture was stirred for 1 hour at the same temperature. To the reaction mixture was added ethyl acetate (80 ml) and the mixture was stirred for 10 minutes. Insoluble matters were filtered off and washed with ethyl acetate (50 ml). The filtrate and washings were combined and evaporated under reduced pressure. To the residue was added ethyl acetate (40 ml) again, and insoluble matters were filtered off. The filtrate was evaporated under reduced pressure. To the residue was added methanol (10 ml) and the solution was allowed to stand for 1 hour at room temperature. The resultant precipitate was collected by filtration, washed with methanol, and dried under reduced pressure to give the title compound (0.7 g) as white needles.

mp: 153° C.
$[\alpha]_D^{22} = -167°$ (C=1.128, in chloroform)
NM (CDCl$_3$) δ: 0.05 (3H, s), 0.11 (3H, s), 0.84 (9H, s), 1.43 (3H, d), 4.3–5.5 (7H, m), 5.58 (1H, d), 7.30 (2H, dd), 7.37 (5H, s), 7.6–7.9 (6H, m)

Reference Example 32

1-[1-R-Methoxycarbonyl-2-S-(t-butyldimethylsilyl)oxypropyl]3-S-phthalimido-4-S-(4-chlorobenzoyl)oxymethylazetidin-2-one In a manner analogous to Reference Example 31 using O-t-butyldimethylsilyl-D-threonine methyl ester instead of O-t-butyldimethylsilyl-D-threonine benzyl ester, the title compound was obtained.

NMR (CDCl$_3$) δ: 0.11 (3H, s), 0.14 (3H, s), 0.85 (9H, s), 1.44 (3H, d), 3.93 (3H, s), 4.4–5.2 (5H, m), 5.76 (1H, d), 7.42 (2H, dd), 7.6–8.0 (6H, m)

Reference Example 33

1-[1-R-Benzyloxycarbonyl-2-S-(t-butyldimethylsilyl)oxypropyl]-3-S-phthalimido-4-S-hydroxymethylazetidin-2one To a solution of 1-[1-R-benzyloxycarbonyl-2-S-(t-butyldimethylsilyl)oxypropyl]-3-S-phthalimido-4-S-(4-chlorobenzoyl)oxymethylazetidin-2-one (6.65 g, 10 mmol) in a mixed solvent of tetrahydrofuran (20 ml) and methanol (20 ml) was added dropwise 1N sodium hydroxide (10 ml) under ice-cooling. The mixture was stirred for 1 hour at the same temperature and the organic solvent was removed under reduced pressure. To the residue was added water (10 ml), and the mixture was adjusted to pH 2 with a 10-fold dilution of concentrated hydrochloric acid and extracted with ethyl acetate (100 ml). The extract was dried over anhydrous magnesium sulfate, filtered and evaporated under reduced pressure. The residue was subjected to silica gel column chromatography [eluent: ethyl acetate-n-hexane (1:2)] for separation and purification to give the title compound (0.92 g).

NMR (CDCl$_3$) δ: 0.05 (3H, s), 0.15 (3H, s), 0.85 (9H, s), 1.45 (3H, d), 4.2–5.6 (7H, m), 5.62 (1H, d), 7.4–7.9 (9H, m)

Reference Example 34

1-[1-S-Benzyloxycarbonyl-2-R-(t-butyldimethylsilyl)oxypropyl]-3-R-phthalimido-4-R-(4-chlorobenzoyl)oxymethylazetidin-2-one A mixture of 4-chlorobenzoyloxyacetaldehyde (0.6 g, 3 mmol) and O-t-butyldimethylsilyl-L-threonine benzyl ester (0.94 g, 3 mmol) in methylene chloride (10 ml) was stirred for 30 minutes and anhydrous magnesium sulfate (3.6 g, 30 mmol) was added thereto. The mixture was stirred for 2 hours at room temperature and cooled to −40° C., and triethylamine (0.83 ml, 6 mmol) was added thereto. To the mixture was added dropwise a solution of 2-phthalimidoacetyl chloride (1.26 g, 6 mmol) in methylene chloride (10 ml) while holding the temperature at −30° C. to −25° C. After completion of the dropwise addition, the mixture was stirred for 1 hour at the same temperature. To the reaction mixture was added ethyl acetate (80 ml) and the mixture was stirred for 10 minutes. Insoluble matters were filtered off and washed with ethyl acetate (50 ml). The filtrate and washings were combined and evaporated under reduced pressure. To the residue was added ethyl acetate (40 ml) again, and insoluble matters were filtered off. The filtrated was evaporated under reduced pressure. To the residue was added methanol (10 ml) and the solution was allowed to stand for 1 hour at room temperature. The resultant precipitate was collected by filtration, washed with methanol, and dreid under reduced pressure to give the title compound (0.7 g) as white needles.

mp: 153° C.

[α]$_D^{22}$ = +163° (C=0.648, in chloroform)

NMR (CDCl$_3$) δ: 0.05 (3H, s), 0.11 (3H, s), 0.84 (9H, s), 1.43 (3H, d), 4.3–5.5 (7H, m), 5.58 (1H, d), 7.30 (2H, dd), 7.37 (5H, s), 7.6–7.9 (6H, m)

Reference Example 35

1-1-R-(4-Nitrobenzyl)oxycarbonyl-2-S-hydroxypropyl]-3-S-(4-nitrophthalimido)-4-S-formylazetidin-2-one A suspension of 1-[1-R-(4-nitrobenzyl)oxycarbonyl-2-S-hydroxypropyl]-3-S-(4-nitrophthalimido)-4-R-styrylazetidin-2-one (30 g) in a mixed solvent of methylene chloride (400 ml) and methanol (200 ml) was cooled in a dry ice-acetone bath and ozone was introduced thereinto. After confirming the disappearance of the spot of the starting compound by thin-layer chromatography, dimethyl sulfide (7.5 ml) was added to the reaction mixture and the temperature of the mixture was returned to room temperature. Methylene chloride (200 ml) and a saturated aqueous solution of sodium chloride (300 ml) were added to the reaction mixture. Thereafter, the methylene chloride layer was separated, dried over anhydrous sodium sulfate, filtered and evaporated under reduced pressure. The residue was washed with diethyl ether to give the title compound (24.9 g) as pale yellow sharp-pointed needles.

mp: 85°–87° C.

NMR (CDCl$_3$) δ: 1.61 (3H, d, J=6.2 Hz), 4.32–4.95 (3H, m), 5.35 (2H, s), 5.70 (1H, d, J=5.5 Hz), 7.56 (2H, d, J=9 Hz), 8.02–8.38 (3H, m), 8.60–8.75 (2H, m)

Reference Example 36

1-[1-R-(4-Nitrobenzyl)oxycarbonyl-2-S-hydroxypropyl]-3-S-(4-nitrophthalimido)-4-S-hydroxymethylazetidin-2-one In tetrahydrofuran (150 ml) was dissolved 1-[1-R-(4-nitrobenzyl)oxycarbonyl-2-S-hydroxypropyl]-3-S-(4-nitrophthalimido)-4-S-formylazetidin-2-one (23 g) and the solution was cooled to −20° C. (referred to as solution A).

On the other hand, in tetrahydrofuran (50 ml) was suspended sodium borohydride (2 g) under ice-cooling, followed by addition of anhydrous zinc chloride (8.6 g), and then the mixture was stirred at the same temperature for 10 minutes and at room temperature for 30 minutes (referred to as solution B).

Subsequently, to the aforementioned solution A was added dropwise the solution B under ice-cooling. After completion of the dropwise addition, the mixture was stirred for 2 hours at the same temperature. To the reaction mixture was added a saturated aqueous solution of sodium chloride and the mixture was extracted twice with ethyl acetate (200 ml). The extract was washed with water, dried over anhydrous magnesium sulfate, filtered, and evaporated under reduced pressure. The residue was recrystallized from acetone-water to give the title compound (11.2 g) as light yellow sharp-pointed needles.

mp: 152°–154° C.

NMR (DMSO-d6-CDCl$_3$) δ: 1.39 (3H, d, J=6.2 Hz), 3.88–4.15 (2H, m), 4.37–4.71 (3H, m), 5.39 (2H, s), 5.52 (1H, d, J=5.5 Hz), 7.68 (2H, d, J=9 Hz), 8.20 (3H, m), 8.72 (2H, m)

In a manner analogous to Reference Example 36, the compounds of Reference Examples 37 to 41 were obtained using appropriate starting compounds.

Reference Example 37

1-(1-R-Benzyloxycarbonyl-2-S-hydroxypropyl)-3-S-phthalimido-4-S-hydroxymethylazetidin-2-one Colorless amorphous solid
mp: 62-°65° C.

Reference Example 38

1-(1-R-Benzhydryloxycarbonyl-2-S-hydroxypropyl)-3-S-phthalimido-4-S-hydroxymethylazetidin-2-one White sharp-pointed needles
mp: 78°-82° C.

Reference Example 39

1-(1-R-Benzhydryloxycarbonyl-2-S-hydroxypropyl)-3-S-(4-nitrophthalimido)-4-S-hydroxymethylazetidin-2-one Light yellow amorphous solid
mp: 68°-72° C.

Reference Example 40

1-(1-R-Benzyloxycarbonyl-2-S-hydroxypropyl)-3-S-(4-nitrophthalimido)-4-S-hydroxymethylazetidin-2-one Colorless amorphous solid
mp: 70°-76° C.

Reference Example 41

1-[1-R-(4-Methoxybenzyl)oxycarbonyl-2-S-hydroxypropyl]-3-S-(4-nitrophthalimido)-4-S-hydroxymethylazetidin-2-one Pale yellow amorphous solid
mp: 82°-87° C.

Reference Example 42

1-[1-R-(4-Nitrobenzyl)oxycarbonyl-2-S-hydroxypropyl]-3-S-(4-nitrophthalimido)-4-S-methanesulfonyloxymethylazetidin-2-one In a mixed solvent of methylene chloride (40 ml) and dimethylformamide (10 ml) was dissolved 1-[1-R-(4-nitrobenzyl)oxycarbonyl-2-S-hydroxypropyl]-3-S-(4-nitrophthalimido)-4-S-hydroxymethylazetidin-2-one (4 g). To the mixture were added mesyl chloride (3.3 g) and triethylamine (5.1 ml) at room temperature and the mixture was stirred for 4 hours at the same temperature. After completion of the reaction, to the mixture were added a 10-fold dilution of concentrated hydrochloric acid (20 ml) and water (100 ml) and the methylene chloride layers was separated. The organic layer was dried over anhydrous magnesium sulfate, filtered and evaporated. The residue was recrystallized from acetone-water to give the title compound (3.4 g) as white sharp-pointed needles.
mp: 162°-163° C.
NMR (CDCl₃) δ: 1.38 (3H, d, J=6.2 Hz), 2.89 (3H, s), 4.35-5.08 (5H, m), 5.35 (2H, s), 7.59 (2H, d, J=9.0 Hz),
8.24 (2H, d, J=9 Hz), 8.04-8.30 (1H, m), 8.66 (2H, m)

Reference Example 43

(3S,4S)-1-[2-Hydroxy-1-(4-nitrobenzyl)oxycarbonyl-1-propenyl]-3-(4-nitrophthalimido)-4-methanesulfonyloxymethylazetidin-2-one In acetone (10 ml) was dissolved 1-[1-R-(4-nitrobenzyl)oxycarbonyl-2-S-hydroxypropyl]-3-S-(4-nitrophthalimido)-4-S-methanesulfonyloxymethylazetidin-2-one (2 g, 3.3 mmol) at 40° C. and the temperature of the solution was returned to room temperature. To the solution was added Jone's reagent (1.5 ml, 4 mmol) and the mixture was stirred for 2 hours at room temperature. To the reaction mixture was added isopropyl alcohol (5 ml) and the mixture was evaporated. To the residue were added methylene chloride (80 ml) and water (40 ml) and the methylene chloride layer was separated. The aqueous layer was extracted twice with methylene chloride (35 ml). The extracts and the methylene chloride solution obtained above were combined, washed twice with a saturated aqueous solution of sodium chloride (50 ml), dried over anhydrous magnesium sulfate and evaporated under reduced pressure to remove methylene chloride. The residue was washed diethyl ether and recrystallized from acetone-water to give the title compound (910 mg) as white sharp-pointed needles.
mp: 198°-199° C.
NMR (CDCl₃-DMSO-d6) δ: 2.35 (3H, s), 2.93 (3H, s), 4.30-4.75 (3H, m), 5.44 (2H, s), 5.62 (1H, d, J TM 3.5 Hz), 7.63 (2H, d, J=9 Hz), 8.33 (2H, d, J=9 Hz), 8.6-8.85 (2H, m), 12.45 (1H, br)

In a manner analogous to Reference Example 43, the compounds of Reference Examples 44 to 46 were obtained using appropriate starting compounds.

Reference Example 44

(3S,4S)-1-(1-Benzhydryloxycarbonyl-2-hydroxy-1-propenyl)-3-phthalimido-4-methanesulfonyloxymethylazetidin-2-one White amorphous solid
mp: 94°-98° C.

Reference Example 45

(3S,4S)-1-(1-Benzyloxycarbonyl-2-hydroxy-1-propenyl)-3-(4-nitrophthalimido)-4-methanesulfonyloxymethylazetidin-2-one White amorphous solid
mp: 73°-77° C.

Reference Example 46

(3S,4S)-1-(1-Benzyhydryloxycarbonyl-2-hydroxy-1-propenyl)-3-(4-nitrophthalimido)-4-methanesulfonyloxymethylazetidin-2-one Light yellow amorphous solid
mp: 97-104° C.

Example 1

(6S,7S)-7-[2-(2-Aminothiazol-4-yl)-2-methoxyiminoacetamido]-3-[[1-(1-pyrrolidinylcarbonylmethyl)-4-pyridinio]thiomethyl]-Δ³-O-2-isocephem-4-carboxylate (syn-isomer)

To benzhydryl (6S,7S)-7-[2-(2-t-butoxycarbonylaminothiazol-4-yl)-2-methoxyiminoacetamido]-3-(pyridin-4-ylthiomethyl)-Δ³-O-2-isocephem-4-carboxylate (syn-isomer) (8 g) were added dimethylformamide (20 ml) and N-(2-bromoacetyl)pyrrolidine (9.6 g) and the reaction was conducted for 16 hours at room temperature. After completion of the reaction, to the reaction mixture was added a mixture of diethyl ether (150 ml) and n-hexane (50 ml). The resultant oily product was separated by decantation and treated with diethyl ether to pulverize. The resultant powder was collected by filtration and dissolved in a mixture of methylene chloride (300 ml) and nitromethane (30 ml). To the solution was added dropwise a solution of anhydrous aluminum chloride (13.3 g) in nitromethane under ice-cooling and the reaction was conducted for 1.5 hours at room temperature. The reaction mixture was poured into ice-water (1 l) and insoluble matters were filtered off. The filtrate was separated into organic layer and aqueous layer. The aqueous layer was adjusted to pH 4 with a saturated aqueous solution of sodium hydrogencarbonate and nonionic adsorbent resin Diaion HP-20 (200 g) was added thereto. The resin was collected by filtration and washed with water (1 l), followed by elution with 0 to 30% aqueous solution of isopropanol. The eluate containing the desired compound was subjected to lyophilization to give the title compound (2.82 g).

mp: 163° C. (discoloration)

In a manner analogous to Example 1, the compounds of Examples 2 to 23 mentioned below were obtained using appropriate starting compounds.

Example 2

(6S,7S)-7-[2-(2-Aminothiazol-4-yl)-2-methoxyiminoacetamido-]3-[(1-benzoylmethyl-4-pyridinio)thiomethyl]-$\Delta^3$-O-2-isocephem-4-carboxylate (syn-isomer)

NMR (DMSO-d6) δ: 3.84 (3H, s), 3.8–4.1 (2H, m), 4.3–4.8 (3H, m), 5.1 (2H, Br.), 5.2–6.77 (1H, s), 7.0–7.8 (5H, m), 7.9–8.15 (2H, dd), 8.4–8.65 (2H, dd), 9.0–9.16 (1H, d)

Example 3

(6S,7S)-7-[2-(2-Aminothiazol-4-yl)-2-methoxyiminoacetamido]-3-[(1-acetonyl-4-pyridinio)thiomethyl]-$\Delta^3$-O-2-isocephem-4-carboxylate (syn-isomer)

NMR (DMSO-d6) δ: 2.28 (3H, s), 3.83 (3H, s), 3.85–4.05 (2H, m), 4.40–4.70 (3H, m), 5.04 (2H, s), 5.45–5.65 (1H, m), 6.76 (1H, s), 8.2–8.35 (2H, dd), 8.37–8.52 (2H, dd), 9.0–9.15 (1H, d)

Example 4

(6S,7S)-7-[2-(2-Aminothiazol-4-yl)-2-cyclopentyloxyiminoacetamido]-3-[[1-(1-pyrrolidinylcarbonylmethyl)-4-pyridinio]thiomethyl]-$\Delta^3$-O-2-isocephem-4-carboxylic acid sulfate (syn-isomer)

mp: 138° C. (discoloration)

Example 5

(6S,7S)-7-[2-(2-Aminothiazol-4-yl)-2-cyclopentyloxyiminoacetamido]-3-[(1-N,N-dimethylcarbamoylmethyl-4-pyridinio)thiomethyl]-$\Delta^3$-O-2-isocephem-4-carboxylic acid sulfate (syn-isomer)

mp: 154° C. (discoloration)

Example 6

(6S,7S)-7-[2-(2-Aminothiazol-4-yl)-2-carbamoylmethoxyiminoacetamido]-3-[(1-methyl-4-pyridinio)thiomethyl]-$\Delta^3$-O-2-isocephem-4-carboxylate (syn-isomer)

mp: 165° C. (discoloration)

Example 7

(6S,7S)-7-[2-(2-Aminothiazol-4-yl)-2-methoxyiminoacetamido]-3-[(1-N,N-dimethylcarbamoylmethyl-4-pyridinio)thiomethyl]-$\Delta^3$-O-2-isocephem-4-carboxylic acid sulfate (syn-isomer)

mp: 121° C. (discoloration)

Example 8

(6S,7S)-7-[2-(2-Aminothiazol-4-yl)-2-cyclopentyloxyiminoacetamido]-3-[(1-propanoylmethyl-4-pyridinio)thiomethyl]-$\Delta^3$-O-2-isocephem-4-carboxylic acid sulfate (syn-isomer)

NMR (DMSO-d6) δ: 1.02 (3H, t), 1.36–2.0 (8H, br.), 3.8–4.1 (2H, m), 4.35–5.0 (6H, m), 5.45–5.83 (3H, m), 6.85 (1H, s), 8.0–8.18 (2H, dd), 8.4–8.58 (2H, dd), 9.05–9.25 (1H, d)

Example 9

(6S,7S)-7-[2-(2-Aminothiazol-4-yl)-2-cyclopentyloxyiminoacetamido]-3-[[1-(1-piperazinylcarbonylmethyl)-4-pyridinio]thiomethyl]-$\Delta^3$-O-2-isocephem-4-carboxylate (syn-isomer)

mp: 148° C. (discolored to a brown color)

Example 10

(6S,7S)-7-[2-(2-Aminothiazol-4-yl)-2-cyclopentyloxyiminoacetamido]-3-[(1-hydroxyaminocarbonylmethyl-4-pyridinio)thiomethyl]$\Delta^3$-O-2-isocephem-4-carboxylate (syn-isomer)

mp: 156° C. (discolored to a brown color)

Example 11

(6S,7S)-7-[2-(2-Aminothiazol-4-yl)-2-methoxyiminoacetamido]-3-[(1-morpholinocarbonylmethyl-4-pyridinio)thiomethyl]-$\Delta^3$-O-2-isocephem-4-carboxylate (syn-isomer)

mp: 153° C. (discolored to a brown color)

Example 12

(6S,7S)-7-[2-(2-Aminothiazol-4-yl)-2-cyclopentyloxyiminoacetamido]-3-[(1-chloromethyl-4-pyridinio)thiomethyl]-$\Delta^3$-O-2-isocephem-4-carboxylate (syn-isomer)

NMR (DMSO-d6) δ: 1.4–2.0 (8H, m), 3.6–3.9 (2H, m), 4.2–5.2 (6H, m), 5.47 (1H, dd), 6.72 (1H, s), 7.16 (2H, bs), 7.95 (2H, d), 8.31 (2H, d), 9.07 (1H, d)
Pale yellow powder
mp: 134° C. (discolored gradually)

Example 13

Benzhydryl
S)-7-[2-(2-tritylaminothiazol-4-yl)-2-cyclopentyloxyiminoacetamido]-3-[(1-chloromethyl-4-pyridinio)thiomethyl]-$\Delta^3$-O-2-isocephem-4-carboxylate iodide (syn-isomer)

Reddish brown powder
mp: 172°–175° C. (decomposition)

Example 14

Benzhydryl
(6S,7S)-7-[2-(2-tritylaminothiazol-4-yl)-2-cyclopentyloxyiminoacetamido]-3-[(1-cyclopropylmethyl-4-pyridinio)thiomethyl]-$\Delta^3$-O-2-isocephem-4-carboxylate bromide (syn-isomer)

Pale yellow powder
mp: 161°–164° C.

Example 15

(6S,7S)-7-[2-(2-Aminothiazol-4-yl)-2-cyclopentyloxyiminoacetamido]-3-[(1-cyclopropylmethyl-4-pyridinio)thiomethyl]-Δ³-O-2-isocephem-4-carboxylic acid ditrifluoroacetate (syn-isomer)

NMR (DMSO-d6) δ: 0.56–0.65 (4H, m), 1.3–1.9 (9H, m), 3.8–4.8 (12H, m), 5.68 (1H, dd), 6.80 (1H, s), 8.08 (1H, d), 8.85 (2H, d), 9.16 (1H, d)

Pale yellow powder
mp: 145° C. (discolored gradually), 162° C. (discolored to a brown color)

Example 16

Benzhydryl (6S,7S)-7-[2-(2-tritylaminothiazol-4-yl)-2-cyclopentyloxyiminoacetamido]-3-[[1-(2-fluoroethyl)-4-pyridinio]thiomethyl]-Δ³-O-2-isocephem-4-carboxylate methanesulfonate (syn-isomer)

Yellow powder
mp: 117°–119° C.

Example 17

(6S,7S)-7-[2-(2-Aminothiazol-4-yl)-2-cyclopentyloxyiminoacetamido]-3-[[1-(2-fluoroethyl)-4-pyridinio]thiomethyl]-Δ³-O-2-isocephem-4-carboxylate (syn-isomer)

NMR (DMSO-d6) δ: 1.4–2.0 (8H, m), 3.3–5.2 (10H, m), 5.52 (1H, dd), 6.72 (1H, s), 7.16 (2H, bs), 8.30 (2H, bs), 8.75 (2H, bs), 9.06 (1H, d)

Pale yellow powder
mp: 164° C. (discolored gradually), 176° C. (discolored to a brown color)

Example 18

(6S,7S)-7-[2-(2-Aminothiazol-4-yl)-2-cyclopentyloxyiminoacetamido]-3-[[1-(2-fluoroethyl)-4-pyridino]thiomethyl]-Δ³-O-2-isocephem-4-carboxylic acid sulfate (syn-isomer)

Pale yellow powder
mp: 161° C. (discolored gradually), 174° C. (discolored to a brown color)

Example 19

Benzhydryl (6S,7S)-7-[2-(2-tritylaminothiazol-4-yl)-2-methoxyiminoacetamido]-3-[[1-(2-fluoroethyl)-4-pyridinio]thiomethyl]-Δ³-O-2-isocephem-4-carboxylate methanesulfonate (syn-isomer)

Pale yellow powder
mp: 126°–129° C.

Example 20

(6S,7S)-7-[2-(2-Aminothiazol-4-yl)-2-methoxyiminoacetamido]-3-[[1-(2-fluoroethyl)-4-pyridinio]thiomethyl]-Δ³-O-2-isocephem-4-carboxylate (syn-isomer)

NMR (DMSO-d6) δ: 3.2–5.2 (12H, m), 5.60 (1H, dd), 6.77 (1H, s), 7.16 (2H, bs), 8.34 (2H, d), 8.72 (2H, d), 9.14 (1H, d)

Pale red powder
mp: 128° C. (discolored gradually), 174° C. (discolored to a brown color rapidly)

Example 21

(6S,7S)-7-[2-(2-Aminothiazol-4-yl)-2-cyclopentyloxyiminoacetamido]-3-[(1-acetonyl-4-pyridinio)thiomethyl]-Δ³-O-2-isocephem-4-carboxylate (syn-isomer)

Pale yellow powder
mp: 152° C. (discoloration)

NMR (DMSO-d6) δ: 1.3–1.9 (8H, m), 2.28 (3H, s), 3.7–4.0 (2H, m), 4.3–4.75 (3H, m), 5.08 (1H, m), 5.38–5.76 (3H, m), 6.72 (1H, s), 7.16 (2H, bs), 8.36 (2H, d), 8.56 (2H, d), 9.08 (1H, d)

Example 22

(6S,7S)-7-[2-(2-Aminothiazol-4-yl)-2-cyclopentyloxyiminoacetamido]-3-[(1-acetonyl-4-pyridinio)thiomethyl]-Δ³-O-2-isocephem-4-carboxylic acid sulfate (syn-isomer)

pale yellow sharp-pointed needles
mp: 154° C. (discoloration)

Example 23

(6S,7S)-7-[2-(2-Aminothiazol-4-yl)-2-cyclopentyloxyiminoacetamido]3-[(1-acetonyl-4-pyridinio)thiomethyl]-Δ³-O-2-isocephem-4-carboxylic acid chloride (syn-isomer)

Pale yellow sharp-pointed needles
mp: 161° C. (discoloration)
$[\alpha]_D^{20} = -70.3°$ (C=1.55, in water)

Example 24

Benzhydryl (6S,7S)-7-[2-(2-aminothiazol-4-yl)-2carbamoylmethoxyiminoacetamido]-3-[(pyridin-4-yl)thiomethyl]-Δ³-O-2-isocephem-4-carboxylate (syn-isomer)

In a mixture of acetic acid (6 ml) and water (1 ml) was dissolved benzhydryl (6S,7S)-7-[2-(2-tritylaminothiazol-4-yl)-2-carbamoylmethoxyiminoacetamido]-3-[(pyridin-4-yl)thiomethyl]-Δ³-O-2-isocephem-4-carboxylate (syn-isomer) (0.21 g, 0.22 mmol) and the mixture was heated at 40° C. After 2 hours, the reaction mixture was evaporated to dryness and the residue was dissolved in ethyl acetate. The solution was washed with a 5% aqueous solution of sodium hydrogencarbonate and a saturated aqueous solution of sodium chloride in turn, dried over anhydrous sodium sulfate, filtered and evaporated to give the title compound (0.09 g).

mp: 147° C. (discoloration)

In a manner analogous to Reference Example 5, the compounds of Examples 25 to 28 below were obtained using appropriate starting compounds.

Example 25

Benzhydryl (6S,7S)-7-[2-(2-tritylaminothiazol-4-yl)-2-carbamoylmethoxyiminoacetamido]-3-[(pyridin-4-yl)thiomethyl]-Δ³-O-2-isocephem-4-carboxylate (syn-isomer)

NMR (CDCl₃) δ: 3.7–4.0 (2H, m), 4.28 (2H, dd, J=13.5 Hz), 4.4–4.7 (3H, m), 5.60 (1H, dd, J=4.5 Hz), 6.67 (1H, s), 6.91 (1H, s), 7.05–7.50 (30H, m), 8.23 (2H, d, J=6 Hz), 8.55 (1H, bs)

Example 26

Benzhydryl (6S,7S)-7-[2-(2-t-butoxycarbonylaminothiazol-4-yl)-2-methoxyiminoacetamido]-3-[[1-(1-pyrrolidinylcarbonylmethyl)-4-pyridinio]thiomethyl]-$\Delta^3$-O-2-isocephem-4-carboxylate bromide (syn-isomer)

mp: 143° C. (discoloration)

Example 27

Benzhydryl (6S,7S)-7-[2-(2-benzyloxycarbonylaminothiazol-4-yl)-2-methoxyiminoacetamido]-3-[[1-(1-pyrrolidinylcarbonylmethyl)-4-pyridinio]thiomethyl]-$\Delta^3$-O-2-isocephem-4-carboxylate bromide (syn-isomer)

mp: 156° C. (discoloration)

Example 28

Benzhydryl (6S,7S)-7-[2-(2-formamidothiazol-4-yl)-2-methoxyiminoacetamido]-3-[[1-(1-pyrrolidinylcarbonylmethy)-4-pyridinio]thiomethyl]-$\Delta^3$-O-2-isocephem-4-carboxylate bromide (syn-isomer)

mp: 151° C. (discoloration)

Example 29

(6S,7S)-7-[2-(2-Aminothiazol-4-yl)-2-cyanomethoxyiminoacetamido]-3-](1-acetonyl-4-pyridinio)thiomethyl]-$\Delta^3$-O-2-isocephem-4-carboxylate (syn-isomer)

In a manner analogous to Example 1, the title compound was obtained using appropriate starting compounds.

mp: 115° C. (discoloration)

NMR (DMSO-d6)$\delta$: 2.28 (3H, s), 3.60–3.95 (2H, m), 4.2–4.75 (3H, m), 5.01 (2H, s), 5.30 (1H, dd), 5.78 (2H, s), 6.70 (1H, s), 7.18 (2H, bs), 8.56 (4H, dd), 9.08 (1H, d)

Pharmaceutical Example 1

| | |
|---|---|
| (6S,7S)-7-[2-(2-Aminothiazol-4-yl)-2-methoxyiminoacetamido]-3-[(1-acetonyl-4-pyridinio)thiomethyl]-$\Delta^3$-O-2-isocephem-4-carboxylate (syn-isomer) | 200 mg |
| Glucose | 250 mg |
| Distilled water for injection | q.s. |
| Total | 5 ml |

In distilled water for injection were dissolved (6S,7S)-7-[2-(2-aminothiazol-4-yl)-2-methoxyiminoacetamido]-3-[(1-acetonyl-4-pyridinio)thiomethyl]-$\Delta^3$-O-2-isocephem-4-carboxylate (syn-isomer) and glucose and the solution was filled into a 5 ml ampule. After nitrogen purging, sterilization was carried out by autoclaving at 121° C. for 15 minutes to give a parenteral product of the above composition.

Pharmaceutical Example 2

| | |
|---|---|
| Benzhydryl (6S,7S)-7-[2-(2-trityl-aminothiazol-4-yl)-2-cyclopentyloxyimino-acetamido]-3-[(1-chloromethyl-4-pyridinio)-thiomethyl]-$\Delta^3$-O-2-isocephem-4-carboxylate iodide (syn-isomer) | 100 g |
| Avicel (trademark of Asahi Chemical Industry) | 40 g |
| Corn starch | 30 g |
| Magnesium stearate | 2 g |
| TC-5 (trademark of Shinetsu Chemical: hydroxypropylmethyl-cellulose) | 10 g |
| Polyethylene glycol 6000 | 3 g |
| Castor oil | 40 g |
| Ethanol | 40 g |

Benzhydryl (6S,7S)-7-[2-(2-tritylaminothiazol-4-yl)-2-cyclopentyloxyiminoacetamido]-3-[(1-chloromethyl-4-pyridino)thiomethyl]-$\Delta^3$-O-2-isocephem-4-carboxylate iodide (syn-isomer), Avicel, corn starch and magnesium stearate were milled together and tableted by means of and R 10 mm punch (for sugar-coated tablets). The resulting tablets were coated with a film coating composition consisting of TC-5, polyethylene glycol 6000, castor oil and ethanol to give film-coated tablets of the above composition.

Pharmaceutical Example 3

| | |
|---|---|
| (6S,7S)-7-[2-(2-Aminothiazol-4-yl)-2-cyclopentyloxyiminoacetamido]-3-[(1-chloromethyl-4-pyridinio)thiomethyl]-$\Delta^3$-O-2-isocephem-4-carboxylate (syn-isomer) | 2 g |
| Purified lanolin | 5 g |
| White beeswax | 5 g |
| White petrolatum | 88 g |
| Total | 100 g |

White beeswax was melted by warming and, then, (6S,7S)-7-[2-(2-aminothiazol-4-yl)-2-cyclopentyloxyiminoacetamido]-3-[(1-chloromethyl-4-pyridinio)thiomethyl]-$\Delta^3$-O-2-isocephem-4-carboxylate (syn-isomer), purified lanolin and white petrolatum were added. The mixture was warmed until it formed a liquid and, then, stirred until it was solidified to give an ointment of the above composition.

Antimicrobial Activity Test

In order to investigate the in vitro activity of the under-mentioned compounds against various bacteria, the minimal inhibitory concentration (MIC) values were determined by the agar plate dilution method [see Chemotherapy, 22, 1126–1128 (1974)].

The results are shown in Table 1.

Each test inoculum was adjusted to $1 \times 10^6$ cells/ml (O.D., 600 m$\mu$: 0.07–0.16).

Test Compounds

No.1  (6S,7S)-7-[2-(2-Aminothiazol-4-yl)-2-methoxyiminoacetamido]-3-[(1-benzoylmethyl-4-pyridinio)-thiomethyl]-$\Delta^3$-O-2-isocephem-4-carboxylate (syn-isomer)

No.2  (6S,7S)-7-[2-(2-Aminothiazol-4-yl-2-methoxyiminoacetamido]-3-[[1-(1-pyrrolidinylcarbonylmethyl)-4-pyridinio]thiomethyl]-$\Delta^3$-0-2-isocephem-4-carboxylate (syn-isomer)

No.3  (6S,7S)-7-[2-(2-Aminothiazol-4-yl)-2-cyclopentyloxyiminoacetamido]-3-[[1-(1-pyrrolidinylcarbonylmethyl)-4-pyridinio]thiomethyl]-$\Delta^3$-O-2-isocephem-4-carboxylic acid sulfate (syn-isomer)

No.4  (6S,7S)-7-[2-(2-Aminothiazol-4-yl)-2-cyclopentyloxyiminoacetamido]-3-[(1-N,N-dimethylcarbamoylmethyl-4-pyridinio)thiomethyl]-$\Delta^3$-O-2-isocephem-4-carboxylic acid sulfate (syn-isomer)

No.5  (6S,7S)-7-[2-(2-Aminothiazol-4-yl)-2-carbamoylmethoxyiminoacetamido]-3-[(1-methyl-4-pyridinio)thiomethyl]-$\Delta^3$-O-2-isocephem-4-carboxylate (syn-isomer)

No.6  (6S,7S)-7-[2-(2-Aminothiazol-4-yl)-2-methoxyiminoacetamido]-3- [(1-N,N-dimethylcarbamoylmethyl-4-pyridinio)thiomethyl]-$\Delta^3$-O-2-isocephem-4-carboxylic acid sulfate (syn-isomer)

No.7  (6S,7S)-7-[2-(2-Aminothiazol-4-yl)-2-cyclopentyloxyiminoacetamido]-3-[(1-propanoylmethyl-4-pyridinio) thiomethyl]-$\Delta^3$-O-2-isocephem-4-carboxylic acid sulfate (syn-isomer)

No.8  (6S,7S)-7-[2-(2-Aminothiazol-4-yl)-2-cyclopentyloxyiminoacetamido]-3-[[1-(1-piperazinylcarbonylmethyl)-4-pyridinio]thiomethyl]-$\Delta^3$-O-2-isocephem-4-carboxylate (syn-isomer)

No.9  (6S,7S)-7-[2-(2-Aminothiazol-4-yl)-2-cyclopentyloxyiminoacetamido]-3-[(1-hydroxyaminocarbonylmethyl-4-pyridinio)thiomethyl]-$\Delta^3$-O-2-isocephem-4-carboxylate (syn-isomer)

No.10 (6S,7S)-7-[2-(2-Aminothiazol-4-yl)-2-methoxyiminoacetamido]-3-[(1-morpholinocarbonylmethyl-4-pyridinio)thiomethyl]-$\Delta^3$-O-2-isocephem-4-carboxylate (syn-isomer)

No.11 (6S,7S)-7-[2-(2-Aminothiazol-4-yl)-2-cyclopentyloxyiminoacetamido]-3-[(1-chloromethyl-4-pyridinio)thiomethyl]-$\Delta^3$-O-2-isocephem-4-carboxylate (syn-isomer)

No.12 (6S,7S)-7-[2-(2-Aminothiazol-4-yl)-2-cyclopentyloxyiminoacetamido]-3-[(1-cyclopropylmethyl-4-pyridinio)thiomethyl]-$\Delta^3$-O-2-isocephem-4-carboxylic acid ditrifluoroacetate (syn-isomer)

No.13 (6S,7S)-7-[2-(2-Aminothiazol-4-yl)-2-cyclopentyloxyiminoacetamido]-3-[[1-(2-fluoroethyl)-4-pyridinio]thiomethyl]-$\Delta^3$-O-2-isocephem-4-carboxylate (syn-isomer)

No.14 (6S,7S)-7-[2-(2-Aminothiazol-4-yl)-2-methoxyiminoacetamido]-3-[[1-(2-fluoroethyl)-4-pyridinio]thiomethyl]-$\Delta^3$-O-2-isocephem-4-carboxylate (syn-isomer)

TABLE 1

| Strain | MIC (μg/ml) Test Compound | | | | | | |
|---|---|---|---|---|---|---|---|
| | No. 1 | No. 2 | No. 3 | No. 4 | No. 5 | No. 6 | No. 7 |
| S. aureus FDA-209-p | 0.05 | 0.2 | 0.1 | 0.1 | 0.2 | 0.2 | 0.1 |
| E. coli NIHJ | 0.05 | ≦0.025 | 0.2 | 0.2 | ≦0.025 | ≦0.025 | 0.2 |
| E. coli No. 29 | ≦0.025 | ≦0.025 | 0.1 | 0.1 | ≦0.025 | ≦0.025 | 0.1 |
| K. pneumoniae NCTC-9632 | 0.05 | ≦0.025 | 0.39 | 0.39 | ≦0.025 | ≦0.025 | 0.39 |
| P. mirabilis 1287 | 0.05 | ≦0.025 | 0.2 | 0.2 | ≦0.025 | ≦0.025 | 0.1 |
| M. morganii ATCC-25830 | 0.05 | ≦0.025 | 0.05 | 0.05 | ≦0.025 | ≦0.025 | 0.05 |
| S. marcescens IFO-12648 | 0.1 | 0.1 | 0.78 | 1.56 | 0.1 | 0.2 | 0.78 |
| P. aeruginosa NCTC-10490 | 1.56 | 1.56 | 0.78 | 1.56 | 12.5 | 3.13 | 0.78 |

| Strain | MIC (μg/ml) Test Compound | | | | | | |
|---|---|---|---|---|---|---|---|
| | No. 8 | No. 9 | No. 10 | No. 11 | No. 12 | No. 13 | No. 14 |
| S. aureus FDA-209-p | 0.2 | 0.39 | 0.2 | 0.1 | 0.05 | 0.1 | 0.2 |
| E. coli NIHJ | 0.2 | 0.2 | ≦0.025 | 0.2 | 0.1 | 0.2 | ≦0.025 |
| E. coli No. 29 | 0.1 | 0.1 | ≦0.025 | 0.1 | 0.05 | 0.1 | ≦0.025 |
| K. pneumoniae NCTC-9632 | 0.2 | 0.39 | ≦0.025 | 0.39 | 0.2 | 0.39 | ≦0.025 |
| P. mirabilis 1287 | 0.39 | 0.2 | ≦0.025 | 0.2 | 0.1 | 0.2 | ≦0.025 |
| M. morganii ATCC-25830 | 0.1 | 0.05 | ≦0.025 | 0.05 | 0.05 | 0.05 | ≦0.025 |
| S. marcescens IFO-12648 | 0.78 | 1.56 | 0.1 | 0.78 | 0.78 | 1.56 | 0.1 |
| P. aeruginosa NCTC-10490 | 0.78 | 3.13 | 6.25 | 1.56 | 0.39 | 0.78 | 1.56 |

What is claimed is:

1. A 2-oxa-isocephem compound of the formula (1):

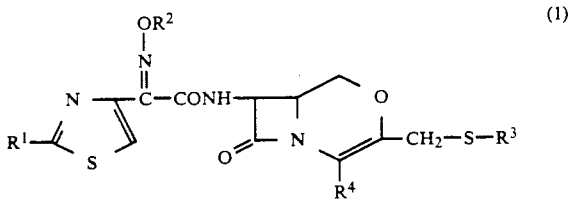

wherein $R^1$ is an amino group; $R^2$ is a $C_2$–$C_6$-alkyl group; $R^3$ is a pyridinio group which is substituted with a group of the formula:

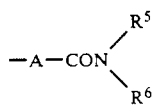

in which A is a $C_1$–$C_6$-alkylene group, $R^5$ is a hydrogen atom or a $C_1$–$C_6$-alkyl group and $R^6$ is a $C_1$–$C_6$-alkyl group or a hydroxy group; and $R^4$ is a carboxy group or a carboxylate group, or its pharmaceutically acceptable salt.

2. A 2-oxa-isocephem compound or its pharmaceutically acceptable salt as claimed in claim 1, wherein $R^2$ is methyl, ethyl, propyl, isopropyl, butyl, isobutyl, tert-butyl, pentyl or hexyl, and $R^3$ is a pyridinio group which is substituted with a group of the formula:

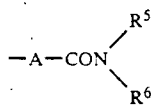

in which A is methylene, methylmethylene, ethylene, dimethylmethylene, trimethylene, 1-methyl-trimethylene, 2-methyl-trimethylene, 2,2-dimethyltrimethylene, tetramethylene, pentamethylene or hexamethylene, $R^5$ is hydrogen, methyl, ethyl, propyl, isopropyl, butyl, isobutyl, tert-butyl, pentyl or hexyl, and $R^6$ is methyl, ethyl, propyl, isopropyl, butyl, isobutyl, tert-butyl, pentyl, hexyl or hydroxy group.

3. A 2-oxa-isocephem compound or its pharmaceutically acceptable salt as claimed in claim 2, wherein $R^2$ is methyl, ethyl or isopropyl, and $R^3$ is a group of the formula:

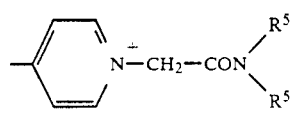

in which $R^5$ is hydrogen or methyl, $R^6$ is methyl or hydroxy.

4. A 2-oxa-isocephem compound of the formula (1):

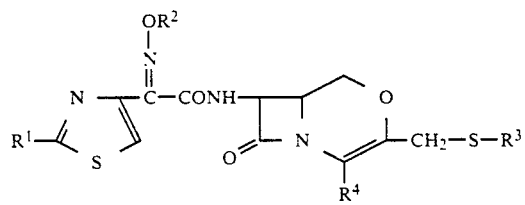

wherein $R^1$ is an amino group; $R^2$ is a $C_1$-$C_6$-alkyl group or a $C_3$-$C_8$-cycloalkyl group; $R^3$ is a pyridinio group which is substituted with a group of the formula:

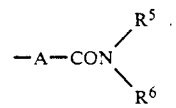

in which A is a $C_1$-$C_6$-alkylene group, $R^5$ is a hydrogen atom or a $C_1$-$C_6$-alkyl group and $R^6$ is a $C_1$-$C_6$-alkyl group or a hydroxy group; and $R^4$ is a carboxy group or a carboxylate group, or its pharmaceutically acceptable salt.

5. A 2oxa-isocephem compound or its pharmaceutically acceptable salt as claimed in claim 4, wherein $R^2$ is methyl, ethyl, propyl, isopropyl, butyl, isobutyl, tert-butyl, pentyl, hexyl, cyclopropyl, cyclobutyl, cyclopentyl, cyclohexyl, cycloheptyl or cyclooctyl, and $R^3$ is a pyridino group which is substituted with a group of the formula:

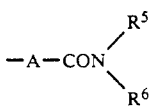

in which A is methylene, methylmethylene, ethylene, dimethylmethylene, trimethylene, 1-methyl-trimethylene, 2-methyl-trimethylene, 2,2-dimethyltrimethylene, tetramethylene, pentamethylene or hexamethylene, $R^5$ is hydrogen, methyl, ethyl, propyl, isopropyl, butyl, isobutyl, tert-butyl, pentyl or hexyl, and $R^6$ is methyl, ethyl, propyl, isopropyl, butyl, isobutyl, tert-butyl, pentyl, hexyl or hydroxyl.

6. A 2-oxa-isocephem compound or its pharmaceutically acceptable salt as claimed in claim 5, wherein $R^2$ is methyl, ethyl, isopropyl or cyclopentyl, and $R^3$ is a group of the formula:

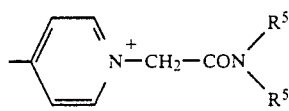

in which $R^5$ is hydrogen or methyl, $R^6$ is methyl or hydroxy.

7. A 2-oxa-isocephem compound or its pharmaceutically acceptable salt as claimed in claim 6, wherein $R^6$ is methyl.

8. A 2-oxa-isocephem compound or its pharmaceutically acceptable salt as claimed in claim 6, wherein $R^6$ is hydroxy.

9. A 2-oxa-isocephem compound or its pharmaceutically acceptable salt as claimed in claim 3, wherein $R^2$ is methyl or ethyl.

10. A 2-oxa-isocephem compound or its pharmaceutically acceptable salt as claimed in claim 3, wherein $R^2$ is methyl or isopropyl.

11. A 2-oxa-isocephem compound or its pharmaceutically acceptable salt as claimed in claim 8, wherein $R^2$ is ethyl or cyclopentyl.

12. A 2-oxa-isocephem compound or its pharmaceutically acceptable salt as claimed in claim 8, wherein $R^2$ is a isopropyl or cyclopentyl.

* * * * *